United States Patent
Cooper et al.

(10) Patent No.: US 11,811,428 B2
(45) Date of Patent: *Nov. 7, 2023

(54) SYSTEM AND METHOD FOR DATA COMPRESSION USING GENOMIC ENCRYPTION TECHNIQUES

(71) Applicant: AtomBeam Technologies Inc., Moraga, CA (US)

(72) Inventors: Joshua Cooper, Columbia, SC (US); Aliasghar Riahi, Orinda, CA (US); Mojgan Haddad, Orinda, CA (US); Ryan Kourosh Riahi, Orinda, CA (US); Razmin Riahi, Orinda, CA (US); Charles Yeomans, Orinda, CA (US)

(73) Assignee: ATOMBEAM TECHNOLOGIES INC., Moraga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,305

(22) Filed: Apr. 21, 2023

(65) Prior Publication Data

US 2023/0253981 A1 Aug. 10, 2023

Related U.S. Application Data

(63) Continuation-in-part of application No. 18/190,044, filed on Mar. 24, 2023, which is a continuation-in-part of application No. 17/875,201, filed on Jul. 27, 2022, and a continuation-in-part of application No. 17/727,913, filed on Apr. 25, 2022, now Pat. No. 11,620,051, said application No.
(Continued)

(51) Int. Cl.
H03M 7/00 (2006.01)
H03M 7/30 (2006.01)
G06N 20/00 (2019.01)

(52) U.S. Cl.
CPC .......... *H03M 7/3059* (2013.01); *G06N 20/00* (2019.01); *H03M 7/6005* (2013.01)

(58) Field of Classification Search
CPC .............. G06F 16/1752; G06F 16/9024; G06F 3/0608; G06F 3/0641; G06F 3/067; H03M 7/40; H03M 7/41; H03M 7/3059; H03M 7/6005; G06N 20/00
See application file for complete search history.

(56) References Cited

U.S. PATENT DOCUMENTS 9,524,392 B2 12/2016 Naehrig et al.
9,804,830 B2 * 10/2017 Raman .................. G06F 16/164
(Continued)

*Primary Examiner* — Jean B Jeanglaude
(74) *Attorney, Agent, or Firm* — Galvin Patent Law LLC; Brian R. Galvin

(57) ABSTRACT

A system and method for data compression with genomic encryption, which uses frequency analysis on data blocks within an input data stream to produce a prefix table, representing a first layer of transformation, and which applies a Burrow's-Wheeler transform (BWT) to the data inside the prefix table, representing a second layer of transformation, and which compresses the transformed data. In some implementations, the system and method may further include applying the BWT to a conditioned stream of genomic data, wherein the conditioned stream of genomic data is accompanied by an error stream comprising the differences between the original data and the encrypted data.

8 Claims, 54 Drawing Sheets

Related U.S. Application Data

17/875,201 is a continuation of application No. 17/514,913, filed on Oct. 29, 2021, now Pat. No. 11,424,760, and a continuation of application No. 17/458,747, filed on Aug. 27, 2021, now Pat. No. 11,422,978, application No. 17/727,913 is a continuation of application No. 17/404,699, filed on Aug. 17, 2021, now Pat. No. 11,385,794, said application No. 17/514,913 is a continuation-in-part of application No. 17/404,699, filed on Aug. 17, 2021, now Pat. No. 11,385,794, said application No. 17/458,747 is a continuation-in-part of application No. 16/923,039, filed on Jul. 7, 2020, now Pat. No. 11,232,076, which is a continuation-in-part of application No. 16/716,098, filed on Dec. 16, 2019, now Pat. No. 10,706,018, which is a continuation-in-part of application No. 16/455,655, filed on Jun. 27, 2019, now Pat. No. 10,509,771, said application No. 17/404,699 is a continuation-in-part of application No. 16/455,655, filed on Jun. 27, 2019, now Pat. No. 10,509,771, which is a continuation-in-part of application No. 16/200,466, filed on Nov. 26, 2018, now Pat. No. 10,476,519, which is a continuation-in-part of application No. 15/975,741, filed on May 9, 2018, now Pat. No. 10,303,391.

(60) Provisional application No. 63/485,518, filed on Feb. 16, 2023, provisional application No. 63/388,411, filed on Jul. 12, 2022, provisional application No. 63/027,166, filed on May 19, 2020, provisional application No. 62/926,723, filed on Oct. 28, 2019, provisional application No. 62/578,824, filed on Oct. 30, 2017.

(56) References Cited

U.S. PATENT DOCUMENTS

| | | | |
|---|---|---|---|
| 2016/0006453 A1* | 1/2016 | Jalali | H03M 5/22 341/87 |
| 2016/0179588 A1* | 6/2016 | Raman | G06F 9/466 719/318 |
| 2018/0196609 A1 | 7/2018 | Niesen | |
| 2019/0235919 A1* | 8/2019 | Barsness | G06F 16/2282 |
| 2020/0249990 A1* | 8/2020 | Barsness | G06F 16/2282 |
| 2020/0395955 A1 | 12/2020 | Choi et al. | |
| 2022/0043778 A1* | 2/2022 | Cooper | G06N 5/01 |

* cited by examiner

SYSTEM AND METHOD FOR DATA COMPRESSION USING GENOMIC ENCRYPTION TECHNIQUES

CROSS-REFERENCE TO RELATED APPLICATIONS

Priority is claimed in the application data sheet to the following patents or patent applications, each of which is expressly incorporated herein by reference in its entirety:
63/485,518
Ser. No. 18/190,044
63/388,411
Ser. No. 17/875,201
Ser. No. 17/458,747
63/027,166
Ser. No. 16/923,039
Ser. No. 16/716,098
Ser. No. 16/455,655
62/926,723
Ser. No. 17/514,913
Ser. No. 17/404,699
Ser. No. 16/455,655
Ser. No. 16/200,466
Ser. No. 15/975,741
62/578,824
Ser. No. 17/727,913

BACKGROUND OF THE INVENTION

Field of the Invention

The present invention is in the field of computer data encoding, and in particular the usage of encoding for enhanced compaction of genomic data.

Discussion of the State of the Art

As computers become an ever-greater part of our lives, and especially in the past few years, data storage has become a limiting factor worldwide. Prior to about 2010, the growth of data storage far exceeded the growth in storage demand. In fact, it was commonly considered at that time that storage was not an issue, and perhaps never would be, again. In 2010, however, with the growth of social media, cloud data centers, high tech and biotech industries, global digital data storage accelerated exponentially, and demand hit the zettabyte (1 trillion gigabytes) level. Current estimates are that data storage demand will reach 175 zettabytes by 2025. By contrast, digital storage device manufacturers produced roughly 1 zettabyte of physical storage capacity globally in 2016. We are producing data at a much faster rate than we are producing the capacity to store it. In short, we are running out of room to store data, and need a breakthrough in data storage technology to keep up with demand.

The primary solutions available at the moment are the addition of additional physical storage capacity and data compression. As noted above, the addition of physical storage will not solve the problem, as storage demand has already outstripped global manufacturing capacity. Data compression is also not a solution. A rough average compression ratio for mixed data types is 2:1, representing a doubling of storage capacity. However, as the mix of global data storage trends toward multi-media data (audio, video, and images), the space savings yielded by compression either decreases substantially, as is the case with lossless compression which allows for retention of all original data in the set, or results in degradation of data, as is the case with lossy compression which selectively discards data in order to increase compression. Even assuming a doubling of storage capacity, data compression cannot solve the global data storage problem. The method disclosed herein, on the other hand, works the same way with any type of data.

Transmission bandwidth is also increasingly becoming a bottleneck. Large data sets require tremendous bandwidth, and we are transmitting more and more data every year between large data centers. On the small end of the scale, we are adding billions of low bandwidth devices to the global network, and data transmission limitations impose constraints on the development of networked computing applications, such as the "Internet of Things".

What is needed is a system and method for highly efficient encoding of data that includes extended functionality such as asymmetric encoding/decoding and genomic encryption.

SUMMARY OF THE INVENTION

The inventor has developed a system and method for highly efficient encoding of data that includes extended functionality such as asymmetric encoding/decoding and distributed computing policy enforcement. In one embodiment, the system and method comprise a form of asymmetric encoding/decoding wherein original data is encoded by an encoder according to a codebook and sent to a decoder, but instead of just decoding the data according to the codebook to reconstruct the original data, data manipulation rules such as mapping, transformation, encryption, are applied at the decoding stage to transform the decoded data into a different data set from the original data. This provides a form of double security, in that the intended final data set is never transferred and can't be obtained even if the codebook is known. It can only be obtained if the codebook and the series of data manipulations after decoding are known. In another embodiment, encoding and decoding can be performed on a distributed computing network by incorporating a behavior appendix into the codebook, such that the encoder and/or decoder at each node of the network comply with network behavioral rules, limits, and policies.

A system and method for data compression with genomic encryption, which uses frequency analysis on data blocks within an input data stream to produce a prefix table, representing a first layer of transformation, and which applies a Burrow's-Wheeler transform (BWT) to the data inside the prefix table, representing a second layer of transformation, and which compresses the transformed data. In some implementations, the system and method may further include applying the BWT to a conditioned stream of genomic data, wherein the conditioned stream of genomic data is accompanied by an error stream comprising the differences between the original data and the encrypted data.

According to a preferred embodiment, a system for genomic data compression with encryption, comprising: a computing device comprising a processor and a memory; a stream analyzer comprising a first plurality of programming instructions stored in the memory which, when operating on the processor, causes the computing device to: receive an input data stream comprising genomic data; analyze the frequency distribution of a plurality of data blocks within the input data stream to determine whether the input data stream meets a configured threshold for data conditioning; if the input data stream meets or exceeds the configured threshold, send the input data stream to a stream conditioner; and the stream conditioner comprising a second plurality of programming instructions stored in the memory which, when operating on the processor, causes the computing device to: receive the input data stream from the stream analyzer; produce a conditioned data stream and an error stream by, for each of a plurality of data blocks within the data stream: analyzing the data block within the data stream to compare the data block's real frequency within the data stream against an ideal frequency; if the difference between the data block's real frequency and ideal frequency exceeds a configured conditioning threshold, applying a conditioning rule to the data block; applying a logical XOR operation to the data block; appending the output of the logical XOR operation to the error stream; send the conditioned data stream and the error stream as output.

According to another preferred embodiment, a method for genomic data compression with encryption, comprising the steps of: receiving an input data stream comprising genomic data; analyzing the frequency distribution of a plurality of data blocks within the input data stream to determine whether the input data stream meets a configured threshold for data conditioning; if the input data stream meets or exceeds the configured threshold, sending the input data stream to a stream conditioner; receiving the input data stream from the stream analyzer; producing a conditioned data stream and an error stream by, for each of a plurality of data blocks within the data stream: analyzing the data block within the data stream to compare the data block's real frequency within the data stream against an ideal frequency; if the difference between the data block's real frequency and ideal frequency exceeds a configured conditioning threshold, applying a conditioning rule to the data block; applying a logical XOR operation to the data block; appending the output of the logical XOR operation to the error stream; and sending the conditioned data stream and the error stream as output.

According to an aspect of an embodiment, the stream analyzer is further configured to:

analyze the frequency distribution of the plurality of data blocks within the input data stream to determine the most frequent bytes or strings of bytes that occur at the beginning of each of the plurality of data blocks; designate the most-frequent bytes or strings of bytes as prefixes; compile a prefix table based on the results of the frequency distribution, the prefix table comprising the designated prefixes and the block lengths; send the prefix table to a data transformer.

According to an aspect of an embodiment, the data transformer comprising a third plurality of programming instructions stored in the memory which, when operating on the processor, causes the computing device to: receive the prefix table; transform each of the plurality of prefixes within the prefix table by applying a Burrow's-Wheeler transform (BWT) and generating as output a plurality BWT-prefixes; and send the plurality of BWT-prefixes as output.

According to an aspect of an embodiment, wherein each of the plurality of data blocks are k-mers of the genomic data and the prefixes are one or more base pairs that occur at the beginning of each k-mer.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION OF THE DRAWING FIGURES

Figure 1:
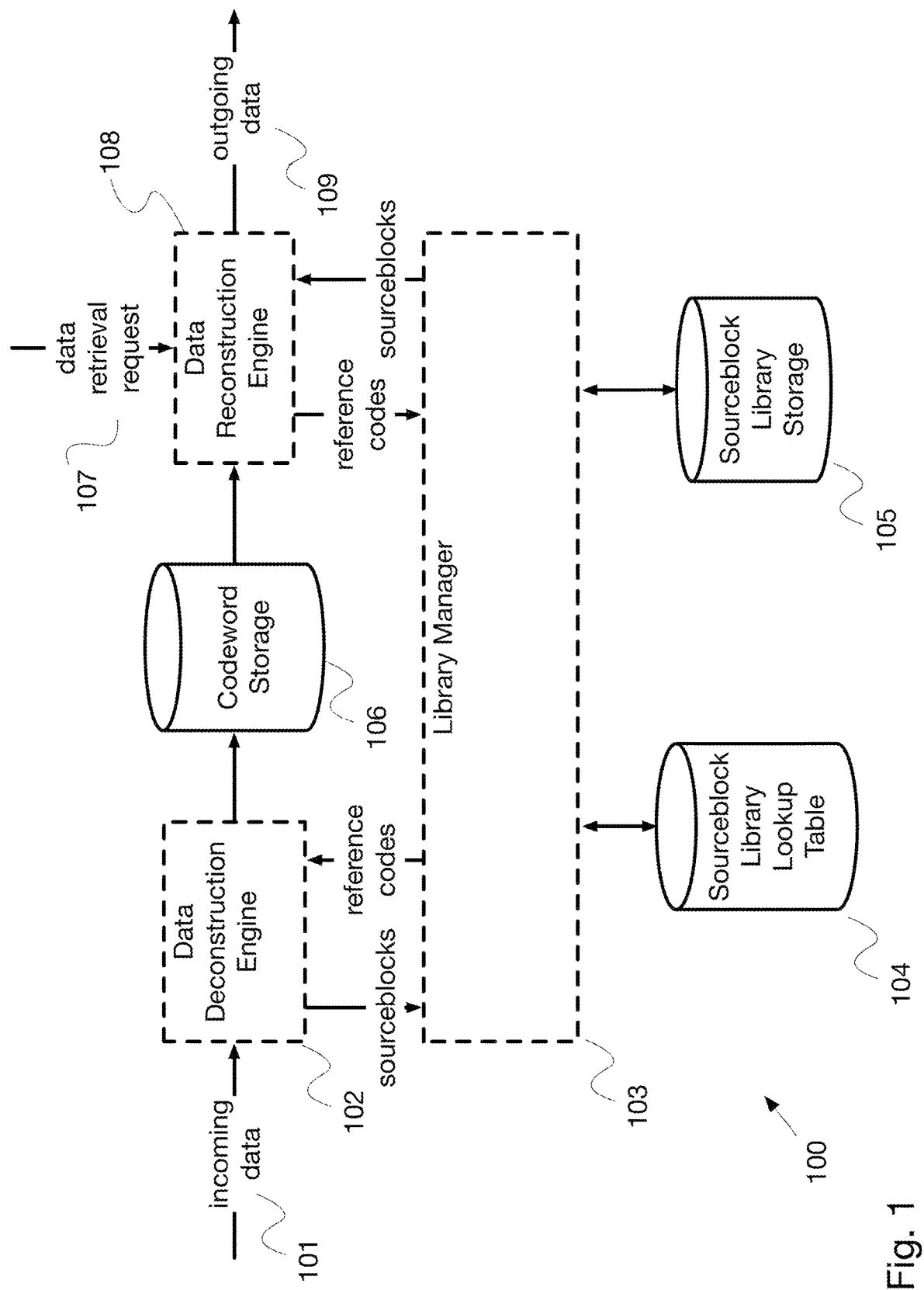
FIG. 1 is a diagram showing an embodiment of the system in which all components of the system are operated locally.

The inventor has conceived, and reduced to practice, a system and method for highly efficient encoding of data that includes extended functionality such as asymmetric encoding/decoding and distributed computing policy enforcement.

In one embodiment, the system and method comprise a form of asymmetric encoding/decoding wherein original data is encoded by an encoder according to a codebook and sent to a decoder, but instead of just decoding the data according to the codebook to reconstruct the original data, data manipulation rules such as mapping, transformation, encryption, are applied at the decoding stage to transform the decoded data into a different data set from the original data. This provides a form of double security, in that the intended final data set is never transferred and can't be obtained even if the codebook is known. It can only be obtained if the codebook and the series of data manipulations after decoding are known.

In another embodiment, encoding and decoding can be performed on a distributed computing network by incorporating a behavior appendix into the codebook, such that the encoder and/or decoder at each node of the network comply with network behavioral rules, limits, and policies. This embodiment is useful because it allows for independent, self-contained enforcement of network rules, limits, and policies at each node of the network within the encoding/decoding system itself, and not through the use of an enforcement mechanism external to the encoding/decoding system. This provides a higher level of security because the enforcement occurs before the data is encoded or decoded. For example, if rule appended to the codebook states that certain sourceblocks are associated with malware and are not to be encoded or decoded, the data cannot be encoded to be transmitted within the network or decoded to be utilized within the network, regardless of external enforcement mechanisms (e.g., anti-virus software, network software that enforces network policies, etc.).

In some embodiments, the data compaction system may be configured to encode and decode genomic data. There are many applications in biology and genomics in which large amounts of DNA or RNA sequencing data must be searched to identify the presence of a pattern of nucleic acid sequences, or oligonucleotides. These applications include, but are not limited to, searching for genetic disorders or abnormalities, drug design, vaccine design, and primer design for Polymerase Chain Reaction (PCR) tests or sequencing reactions.

These applications are relevant across all species, humans, animals, bacteria, and viruses. All of these applications operate within large datasets; the human genome for example, is very large (3.2 billion base pairs). These studies are typically done across many samples, such that proper confidence can be achieved on the results of these studies. So, the problem is both wide and deep, and requires modern technologies beyond the capabilities of traditional or standard compression techniques. Current methods of compressing data are useful for storage, but the compressed data cannot be searched until it is decompressed, which poses a big challenge for any research with respect to time and resources.

The compaction algorithms described herein not only compress data as well as, or better than, standard compression technologies, but more importantly, have major advantages that are key to much more efficient applications in genomics. First, some configurations of the systems and method described herein allow random access to compacted data without unpacking them first. The ability to access and search within compacted datasets is a major benefit and allows for utilization of data for searching and identifying sequence patterns without the time, expense, and computing resources required to unpack the data. Additionally, for some applications certain regions of the genomic data must be searched, and certain configurations of the systems and methods allow the search to be narrowed down even within compacted data. This provides an enormous opportunity for genomic researchers and makes mining genomics datasets much more practical and efficient.

In some embodiments, data compaction may be combined with data serialization to maximize compaction and data transfer with extremely low latency and no loss. For example, a wrapper or connector may be constructed using certain serialization protocols (e.g., BeBop, Google Protocol Buffers, MessagePack). The idea is to use known, deterministic file structure (schemes, grammars, etc.) to reduce data size first via token abbreviation and serialization, and then to use the data compaction methods described herein to take advantage of stochastic/statistical structure by training it on the output of serialization. The encoding process can be summarized as: serialization-encode→compact-encode, and the decoding process would be the reverse: compact-decode-→serialization-decode. The deterministic file structure could be automatically discovered or encoded by the user manually as a scheme/grammar. Another benefit of serialization in addition to those listed above is deeper obfuscation of data, further hardening the cryptographic benefits of encoding using codebooks.

In some embodiments, the data compaction systems and methods described herein may be used as a form of encryption. As a codebook created on a particular data set is unique (or effectively unique) to that data set, compaction of data using a particular codebook acts as a form of encryption as that particular codebook is required to unpack the data into the original data. As described previously, the compacted data contains none of the original data, just codeword references to the codebook with which it was compacted. This inherent encryption avoids entirely the multiple stages of encryption and decryption that occur in current computing systems, for example, data is encrypted using a first encryption algorithm (say, AES-256) when stored to disk at a source, decrypted using AES-256 when read from disk at the source, encrypted using TLS prior to transmission over a network, decrypted using TLS upon receipt at the destination, and re-encrypted using a possibly different algorithm (say, TwoFish) when stored to disk at the destination.

In some embodiments, an encoding/decoding system as described herein may be incorporated into computer monitors, televisions, and other displays, such that the information appearing on the display is encoded right up until the moment it is displayed on the screen. One application of this configuration is encoding/decoding of video data for computer gaming and other applications where low-latency video is required. This configuration would take advantage of the typically limited information used to describe scenery/imagery in low-latency video software applications, such an in gaming, AR/VR, avatar-based chat, etc. The encoding would benefit from there being a particularly small number of textures, emojis, AR/VR objects, orientations, etc., which can occur in the user interface (UI)—at any point along the rendering pipeline where this could be helpful.

In some embodiments, the data compaction systems and methods described herein may be used to manage high volumes of data produced in robotics and industrial automation. Many AI based industrial automation and robotics applications collect a large amount of data from each machine, particularly from cameras or other sensors. Based upon the data collected, decisions are made as to whether the process is under control or the parts that have been manufactured are in spec. The process is very high speed, so the decisions are usually made locally at the machine based on an AI inference engine that has been previously trained. The collected data is sent back to a data center to be archived and for the AI model to be refined.

In many of these applications, the amount of data that is being created is extremely large. The high production rate of these machines means that most factory networks cannot transmit this data back to the data center in anything approaching real time. In fact, if these machines are operating close to 24 hours a day, 7 days a week, then the factory networks can never catch up and the entirety of the data cannot be sent. Companies either do data selection or use some type of compression requiring expensive processing power at each machine to reduce the amount of data that needs to be sent. However, this either loads down the processors of the machine, or requires the loss of certain data in order to reduce the required throughput.

The data encoding/decoding systems and methods described herein can be used in some configurations to solve this problem, as they represent a lightweight, low-latency, and lossless solution that significantly reduces the amount of data to be transmitted. Certain configurations of the system could be placed on each machine and at the server/data center, taking up minimal memory and processing power and allowing for all data to be transmitted back to the data center. This would enable audits whenever deeper analysis needs to be performed as, for example, when there is a quality problem. It also ensures that the data centers, where the AI models are trained and retrained, have access to all of the up-to-date data from all the machines.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

The term "bit" refers to the smallest unit of information that can be stored or transmitted. It is in the form of a binary digit (either 0 or 1). In terms of hardware, the bit is represented as an electrical signal that is either off (representing 0) or on (representing 1).

The term "byte" refers to a series of bits exactly eight bits in length.

The term "codebook" refers to a database containing sourceblocks each with a pattern of bits and reference code unique within that library. The terms "library" and "encoding/decoding library" are synonymous with the term codebook.

The terms "compression" and "deflation" as used herein mean the representation of data in a more compact form than the original dataset. Compression and/or deflation may be either "lossless", in which the data can be reconstructed in its original form without any loss of the original data, or "lossy" in which the data can be reconstructed in its original form, but with some loss of the original data.

The terms "compression factor" and "deflation factor" as used herein mean the net reduction in size of the compressed data relative to the original data (e.g., if the new data is 70% of the size of the original, then the deflation/compression factor is 30% or 0.3.)

The terms "compression ratio" and "deflation ratio", and as used herein all mean the size of the original data relative to the size of the compressed data (e.g., if the new data is 70% of the size of the original, then the deflation/compression ratio is 70% or 0.7.)

The term "data" means information in any computer-readable form.

The term "data set" refers to a grouping of data for a particular purpose. One example of a data set might be a word processing file containing text and formatting information.

The term "effective compression" or "effective compression ratio" refers to the additional amount data that can be stored using the method herein described versus conventional data storage methods. Although the method herein described is not data compression, per se, expressing the additional capacity in terms of compression is a useful comparison.

The term "sourcepacket" as used herein means a packet of data received for encoding or decoding. A sourcepacket may be a portion of a data set.

The term "sourceblock" as used herein means a defined number of bits or bytes used as the block size for encoding or decoding. A sourcepacket may be divisible into a number of sourceblocks. As one non-limiting example, a 1 megabyte sourcepacket of data may be encoded using 512 byte sourceblocks. The number of bits in a sourceblock may be dynamically optimized by the system during operation. In one aspect, a sourceblock may be of the same length as the block size used by a particular file system, typically 512 bytes or 4,096 bytes.

The term "codeword" refers to the reference code form in which data is stored or transmitted in an aspect of the system. A codeword consists of a reference code to a sourceblock in the library plus an indication of that sourceblock's location in a particular data set.

Conceptual Architecture

Figure 51:
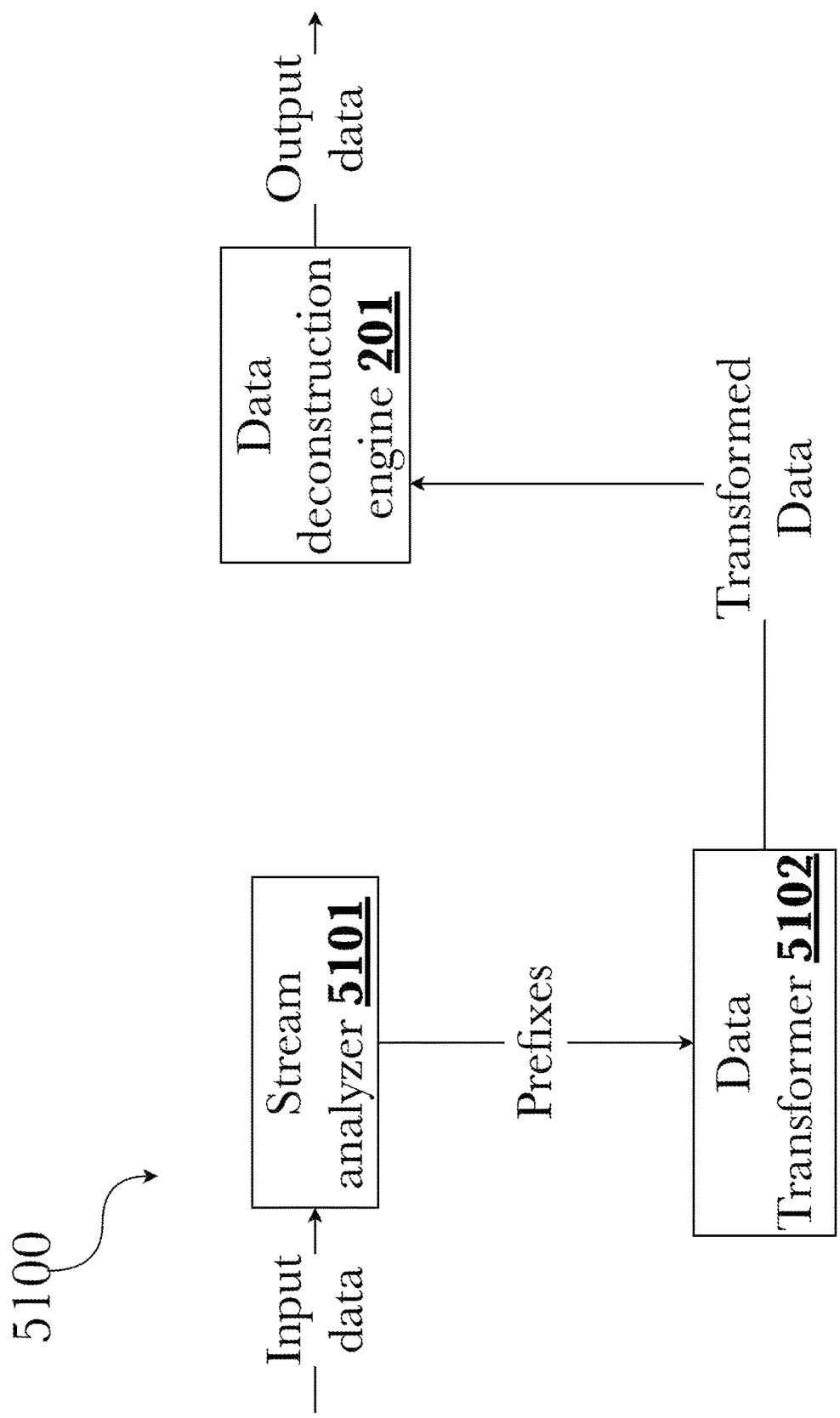
FIG. 51 is a block diagram illustrating an exemplary system architecture for combining data compression with genomic encryption techniques.

FIG. 51 is a block diagram illustrating an exemplary system 5100 architecture for combining data compression with genomic encryption techniques. According to the embodiment, an incoming data stream can be compressed and encrypted simultaneously through the use of prefix tables and the Burrows-Wheeler transform (BWT), wherein the data stream is broken into blocks (e.g., data strings) that are analyzed to identify all prefixes of the data block to determine their frequency distribution within the received data stream. BWT works provably well at transforming data into a more compressible format using a reversible and processing time efficient algorithm. A stream analyzer 5101 is present and configured to receive an input data stream and break the data stream into data blocks (e.g., sourceblocks, data strings). The data stream and resulting data blocks may be associated with a closed domain where only a limited set of data may be admitted into a data set. For example, text data where the only data admitted are text characters (e.g., American Standard Code for Information Interchange (ASCII) characters) represents a closed domain. In another example, a data domain for genetic information may be the closed set of adenine, thymine, guanin, and cytosine, commonly denoted as A, T, G, and C, wherein the four elements represent a closed domain.

According to the embodiment, stream analyzer 5101 is configured to perform frequency analysis on the input data stream by analyzing a plurality of data blocks which the input data stream comprises. Each data block is analyzed to identify and designate one or more possible prefixes that can be associated with that data block. In some aspects, a data cache is present which can temporarily store identified prefixes so that stream analyzer 5101 can quickly compare identified prefixes with those stored in the cache to determine if the prefix is unique or not. In some embodiments, the identified prefixes are bytes or strings of bytes that occur at the beginning of each of the plurality of data blocks associated with the input data stream. As each data block is analyzed, stream analyzer 5101 keep count of the total amount of times each prefix occurs and also the total prefix count for an input data stream. Using at least this information stream analyzer 5101 is able to generate a frequency distribution which can be used to identify the most-common to least-common prefixes. Once the data stream has been analyzed, the data blocks rotated, and all prefixes identified and designated, stream analyzer 5101 can compile a prefix table of results. The prefix table may comprise a list of all designated prefixes and their length (e.g., 8-bits, 16-bits, 10 genetic letters, etc.). In an example, the prefix table may order the information contained therein from most-common to least-common prefixes. In some implementations, the prefix table comprises the prefixes and block lengths, but not the full block contents.

Once a data block has been analyzed and one or more prefixes identified, the data remaining for each block that was not part of the identified prefix may be broken into one or more chunks with a pointer or offset which indicates which prefix each chunk is associated with. The chunks may be sent directly to data deconstruction engine 201 for deconstruction into codewords as described below in greater detail (with reference to FIG. 2). The identified prefix data (e.g., in the form of a prefix table) may be sent to a data transformer 5102.

The determined prefixes based on the determined frequency distribution may then be sent data transformer 5102 which is configured to transform the received prefixes from stream analyzer 5101 and to apply one or more data transformations to each prefix to encrypt it and/or put it into a format more readily compressible, according to the embodiment. According to an aspect, data transformer 5102 may apply a Burrow's-Wheeler transform to the received data. For example, data transformer 5102 may receive prefix data and pass it through a BWT algorithm which produces as output a BWT-prefix which can be easily reversed to produce the original prefix.

Each data block of the data stream may be passed through a modified BWT algorithm to prepare the data stream for data compaction. The Burrows-Wheeler transform is a reversible algorithm used to prepare data for use with data compression techniques. Technically, BWT is a lexicographical reversible permutation of the characters of a string. An important application of BWT is found in biological sciences where genomes (long strings written in A, C, T, G alphabets) do not have many runs but they do have many repeats. The idea of the BWT is to build an array whose rows are all cyclic shifts of the input string in dictionary order and return the last column of the array that tends to have long runs of identical characters. One benefit of this is that once the characters have been clustered together, they effectively have an ordering, which can make the string more compressible for other algorithms such as Huffman coding. The last column is selected because it has better symbol clustering than any other columns and because the last column is the only column from which the original string of characters can be recovered.

When a data string (e.g., data block, character string) is transformed by BWT, the transformation permutes the order of the characters. If the original data string had several substrings that occurred often, then the transformed string will have several places where a single character is repeated multiple times in a row. The output is easier to compress because it has many repeated characters. In different implementations, variations of the BWT may be applied such as, for example, prefix-based BWT. Generally, the transform is done by sorting all the circular shifts of a text in lexicographic order and by extracting the last column and the index of the original string in the set of sorted permutations. Among the benefits of implementing BWT with disclosed data compaction techniques is that the transform is completely reversible, allowing the original data stream to be re-generated from the last column of data.

When implementing the BWT, character rotation is applied to each data block. The BWT can iterate through all possible characters to identify all prefixes using each possible match. In some implementations, the data stream may comprise genomic information and the data blocks may represent k-mers, wherein k-mers are substrings of length k contained within a biological sequence. Usually, the term k-mer refers to all of a sequence's subsequences of length k, such that the sequence ATAG would have four monomers (A, T, A, and G), three 2-mers (AT, TA, and AG), two 3-mers (ATA and TAG) and one 4-mer (ATAG). More generally, a sequence of length L will have L−k+1 k-mers and $n^k$ total possible k-mers, where n is the number of possible monomers (e.g., four in the case of DNA). Prefixes in k-mers are genetic segments; base pairs that occur at the beginning of each k-mer. In the present invention, the identified prefixes are bytes or strings of bytes that occur at the beginning of data blocks (i.e., sourceblocks) and may be selected based on frequency distribution.

In some implementations, stream analyzer 5101 is configured to apply character rotations to each data block of the received input data stream and apply frequency analysis to the rotations of each data block of the data stream.

In some implementations, k-mers and reference strings (also referred to herein as reference stream) may be used to further improve compression efficiency and reduce the amount of computational resources required to encrypt/decrypt a received data stream. Generally, reference-based compression algorithms can obtain better compression ratio than general purpose and reference-free compression algorithms. Data blocks based on prefixes are analogous to genomic k-mers. However, for reference-based compression algorithms, the choice of the reference string will directly influence the performance and stability of the algorithm. A reference string may be an unencrypted data stream selected or generated by the system. In some aspects, the reference string may be a reference genome. In some implementations, the selection of the reference string may be conducted in a random or pseudorandom process, so as to avoid the risk of reverse-engineering the encrypted/compressed data based on similarity. In other implementations, the reference stream may be based on and may comprise one or more prefixes from the prefix table. As a simple illustrative example, the ten (or twenty, or one hundred, etc.) most-common prefixes may be aggregated together to form a reference stream. Further, a prefix table may be used to analyze reference strings and map blocks from the input stream. For example, a data block is received by stream analyzer 5101 and a prefix is determined for that data block, or a prefix table may be used to compare identified prefixes with prefixes that already exist in the prefix table. The prefix table and data block may be sent to data transformer 5102 which compares the data block and/or prefix with a reference stream (e.g., reference string, reference genome, etc.) in order to map the data blocks from the input data stream to the reference stream by identifying prefixes that exist within the reference stream. In some implementations, the system 5100 can locate occurrences of data blocks from the input stream within the reference stream and generate a list of location markers (i.e., location codes) for the blocks. System 5100 may be further configured to append the location markers to a delta stream. In this case, the prefix table and the delta stream are sufficient to reconstruct the data from the reference stream. This process has some advantages such as high compression, wherein only prefixes and location markers are sent (not full blocks). Likewise, the process is advantageous in that if provides high encryption, wherein the only bulk data in use is the randomly-generated reference stream which has no implicit correlation to the input stream.

The gene sequencing data compression system and methods disclosed herein are capable of effectively improving the compression ratio of the gene sequencing data, and has the advantages of low compression ratio, short compression time, and stable compression performance.

In some implementations, data stream analyzer 5101 may first analyze the data stream using split-beam processing as described in FIG. 47 below. In such an implementation, the stream analyzer 5101 and stream conditioner 4702 may prepare the input data stream such that the data blocks sourced from the input data stream are dyadic. The output of the stream conditioner 4702 may then be passed through data transformer 5102 which applies the BWT algorithm to the conditioned data stream, thereby increasing the compressibility of each conditioner block before being sent to data deconstruction engine 201 for compression and encryption.

Figure 52:
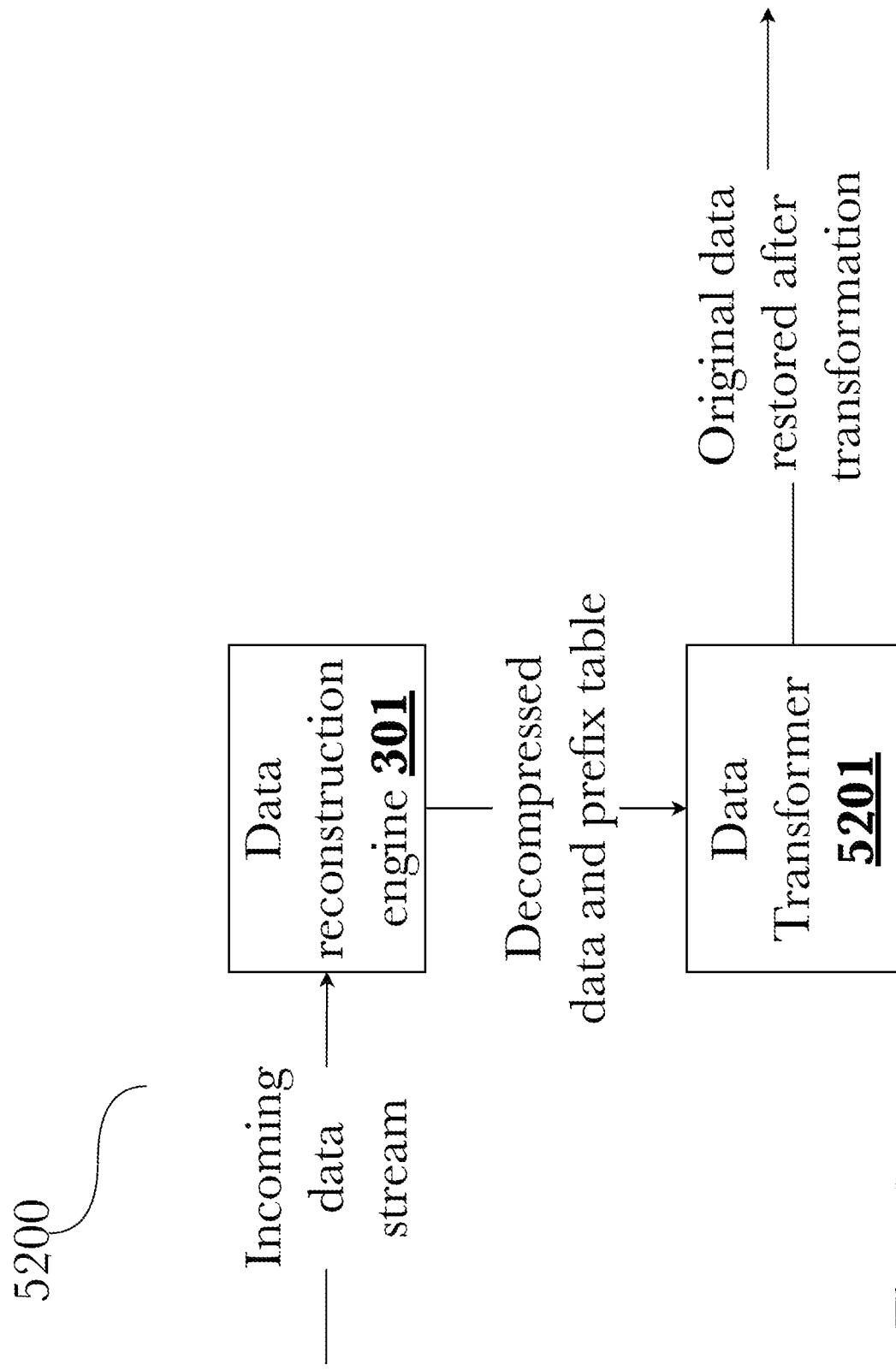
FIG. 52 is a block diagram illustrating an exemplary system architecture for decompressing and decrypting incoming data that was processed using prefix tables and BWT.

FIG. 52 is a block diagram illustrating an exemplary system architecture 5200 for decompressing and decrypting incoming data that was processed using prefix tables and BWT. To decompress and decrypt received data, a data reconstruction engine 301 may first be used to reverse the compression on a data stream as described below in FIG. 3, passing the decompressed (but still encrypted) data to a data transformer 5201. The corresponding prefix table may be separated from the data stream (for example, the two streams may have been combined during compression but during decompression they are separated) or it may be received independently as a second data stream. Data transformer 5201 uses the prefix lengths for each BWT-prefix and applies the reversible BWT algorithm to restore the prefix table to its original format and then uses the prefix table on the decompressed and decrypted data to restore the original data on a block-by-block basis.

Figure 53:
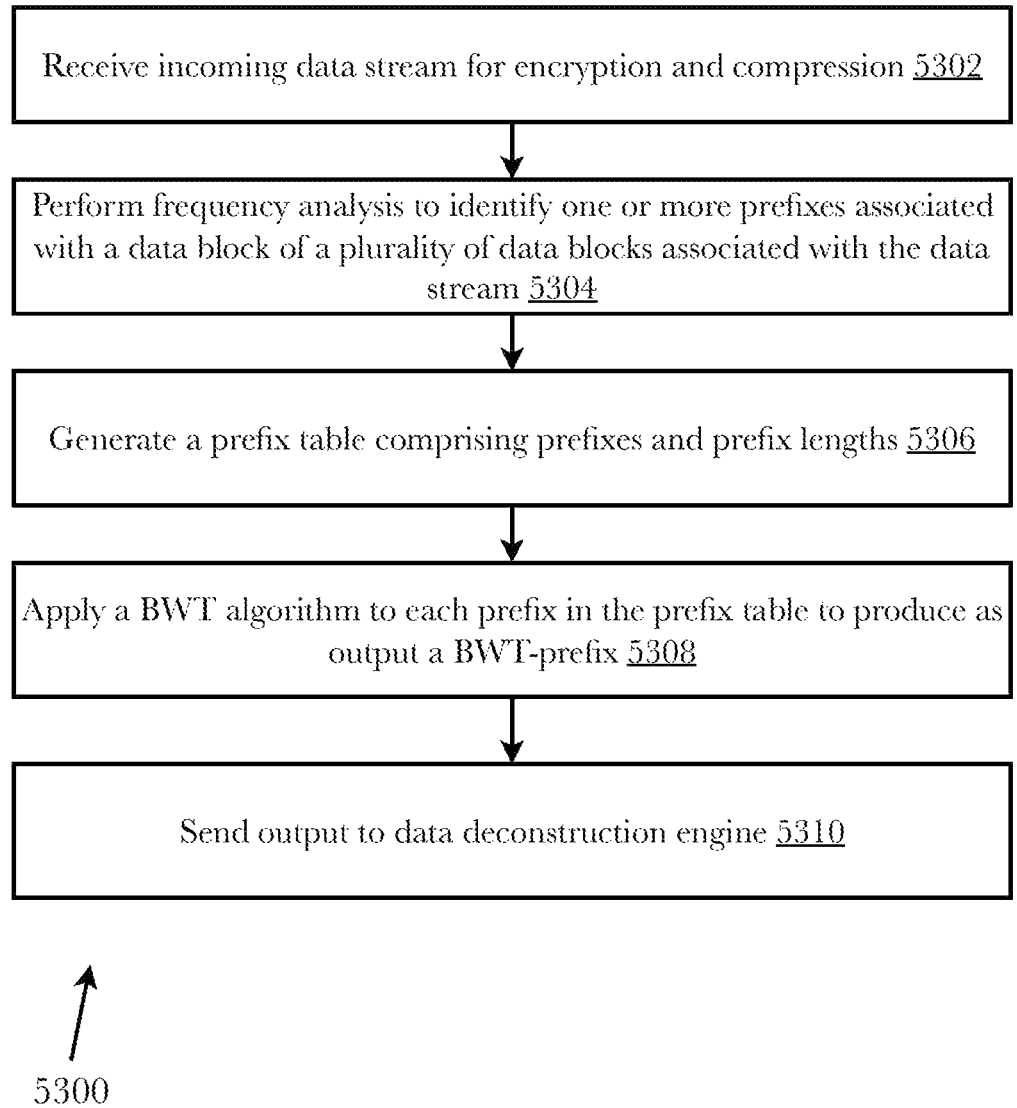
FIG. 53 is a flow diagram illustrating an exemplary method for compressing and encrypting data using prefix tables and BWT.

FIG. 53 is a flow diagram illustrating an exemplary method 5300 for compressing and encrypting data using prefix tables and BWT. In an initial step 5302, a data stream is received for compression and encryption. Each block in the data stream may be analyzed to identify one or more prefixes that are associated with the block and a frequency distribution of the prefixes is produced at step 5304. The most common bytes or strings of bytes that occur at the start of each block may be designated as prefixes and stream analyzer 5101 can generate a prefix table comprising prefixes and prefix lengths at step 5306. As a next step 5308, each prefix in the prefix table is then processed by a BWT algorithm to produce as output a BWT-prefix. A BWT-prefix is a highly more compressible format for a prefix, wherein the prefix is already acting a mechanism to improve the compressibility of the input data stream, which improves the efficiency of the compression and encryption mechanisms of the data deconstruction engine 201. As a last step 5310, data transformer 5102 may send the prefix table with BWT-prefixes and their lengths as output to the data deconstruction engine 201 for compression as described in further detail below, with reference to at least FIG. 10.

Figure 54:
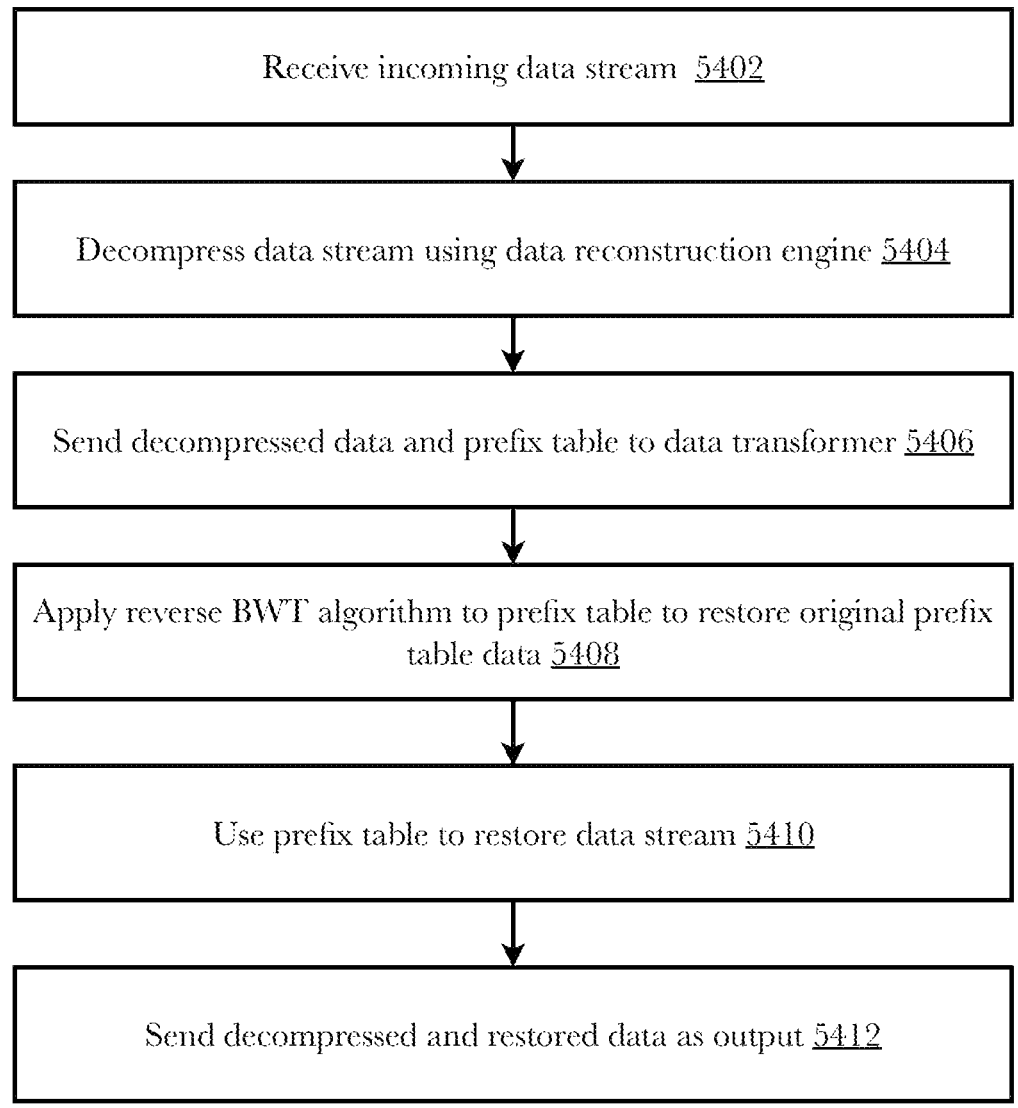
FIG. 54 is a flow diagram illustrating an exemplary method for decrypting and decompressing genomic data using prefix tables and BWT.

FIG. 54 is a flow diagram illustrating an exemplary method 5400 for decrypting and decompressing genomic data using prefix tables and BWT. In an initial step 5402, a data stream is received at a data reconstruction engine 301. The data stream is decompressed 5404 by reversing the encoding as described below with reference to FIG. 11, and the decompressed (but still encrypted) data and prefix table are passed 5406 to a data transformer 5201. The data transformer 5201 performs a reverse BWT algorithm which restores the BWT-prefixes to their original prefix table form at step 5408. Data transformer 5201 may then use the prefix table and decompressed data to restore the original data stream 5410 which may then be sent as output to an appropriate endpoint 5412.

Figure 47:
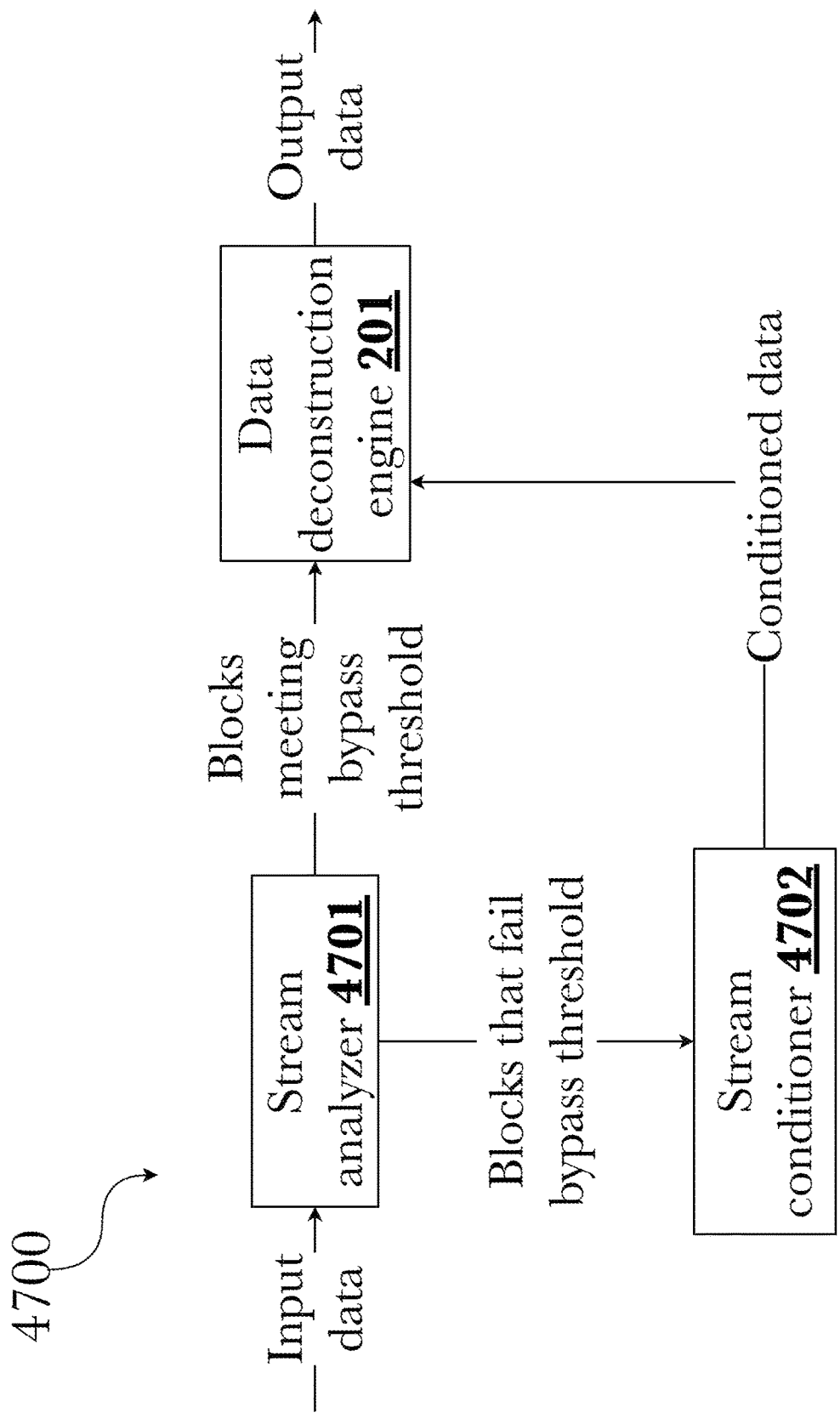
FIG. 47 is a block diagram illustrating an exemplary system architecture for combining data compression with encryption using split-stream processing.

FIG. 47 is a block diagram illustrating an exemplary system architecture 4700 for combining data compression with encryption using split-stream processing. According to the embodiment, an incoming data stream can be compressed and encrypted simultaneously through the use of split-stream processing, wherein the data stream is broken into blocks that are compared against the stream as a whole to determine their frequency (i.e., their probability distribution within the data stream). Huffman coding works provably ideally when the elements being encoded have dyadic probabilities, that is probabilities that are all of the form $1/(2^x)$; in actual practice, not all data blocks will have a dyadic probability, and thus the efficiency of Huffman coding decreases. To improve efficiency while also providing encryption of the data stream, those blocks that have non-dyadic probability may be identified and replaced with other blocks, effectively shuffling the data blocks until all blocks present in the output stream have dyadic probability by using some blocks more frequently and others less frequently to "adjust" their probability within the output stream. For purposes of reconstruction, a second error stream is produced that contains the modifications made, so that the recipient need only compare the error stream against the received data stream to reverse the process and restore the data.

A stream analyzer 4701 receives an input data stream and analyzes it to determine the frequency of each unique data block within the stream. A bypass threshold may be used to determine whether the data stream deviates sufficiently from an idealized value (for example, in a hypothetical data stream with all-dyadic data block probabilities), and if this threshold is met the data stream may be sent directly to a data deconstruction engine 201 for deconstruction into codewords as described below in greater detail (with reference to FIG. 2). If the bypass threshold is not met, the data stream is instead sent to a stream conditioner 4702 for conditioning.

Stream conditioner 4702 receives a data stream from stream analyzer 4701 when the bypass threshold is not met, and handles the encryption process of swapping data blocks to arrive at a more-ideal data stream with a higher occurrence of dyadic probabilities; this facilitates both encryption of the data and greater compression efficiency by improving the performance of the Huffman coding employed by data deconstruction engine 201. To achieve this, each data block in the data stream is checked against a conditioning threshold using the algorithm $|(P_1-P_2)|>T_C$, where $P_1$ is the actual probability of the data block, $P_2$ is the ideal probability of the block (generally, the nearest dyadic probability), and $T_C$ is the conditioning threshold value. If the threshold value is exceeded (that is, the data block's real probability is "too far" from the nearest ideal probability), a conditioning rule is applied to the data block. After conditioning, a logical XOR operation may be applied to the conditioned data block against the original data block, and the result (that is, the difference between the original and conditioned data) is appended to an error stream. The conditioned data stream (containing both conditioned and unconditioned blocks that did not meet the threshold) and the error stream are then sent to the data deconstruction engine 201 to be compressed, as described below in FIG. 2.

To condition a data block, a variety of approaches may be used according to a particular setup or desired encryption goal. One such exemplary technique may be to selectively replace or "shuffle" data blocks based on their real probability as compared to an idealized probability: if the block occurs less-frequently than desired or anticipated, it may be added to a list of "swap blocks" and left in place in the data stream; if a data block occurs more frequently than desired, it is replaced with a random block from the swap block list. This increases the frequency of blocks that were originally "too low", and decreases it for those that were originally "too high", bringing the data stream closer in line with the idealized probability and thereby improving compression efficiency while simultaneously obfuscating the data. Another approach may be to simply replace too-frequent data blocks with any random data block from the original data stream, eliminating the need for a separate list of swap blocks, and leaving any too-low data blocks unmodified. This approach does not necessarily increase the probability of blocks that were originally too-low (apart from any that may be randomly selected to replace a block that was too-high), but it may improve system performance due to the elimination of the swap block list and associated operations.

It should be appreciated that both the bypass and conditioning thresholds used may vary, for example, one or both may be a manually-configured value set by a system operator, a stored value retrieved from a database as part of an initial configuration, or a value that may be adjusted on-the-fly as the system adjusts to operating conditions and live data.

Figure 48:
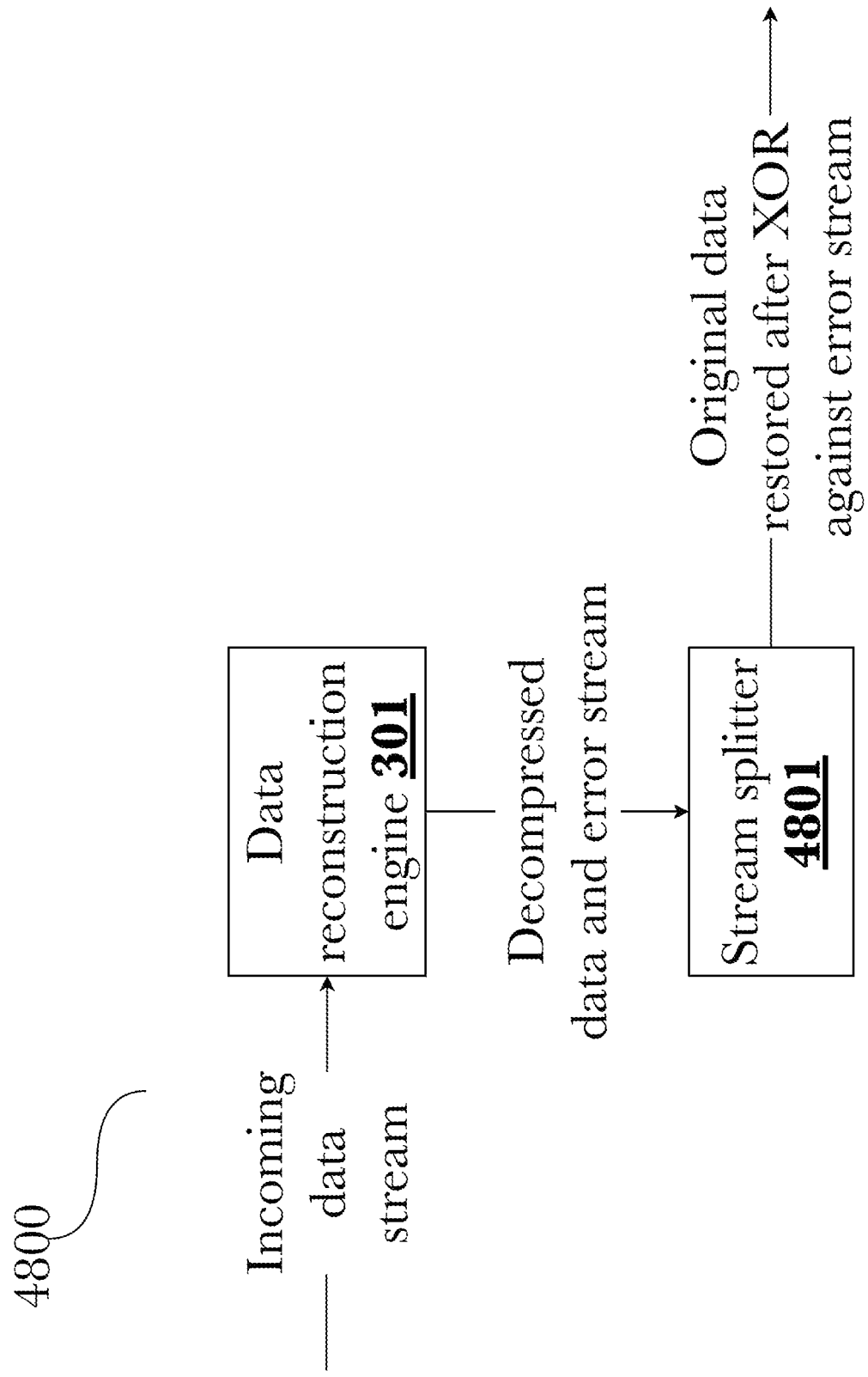
FIG. 48 is a block diagram illustrating an exemplary system architecture for decompressing and decrypting incoming data that was processed using split-stream processing.

FIG. 48 is a block diagram illustrating an exemplary system architecture 4800 for decompressing and decrypting incoming data that was processed using split-stream processing. To decompress and decrypt received data, a data reconstruction engine 301 may first be used to reverse the compression on a data stream as described below in FIG. 3, passing the decompressed (but still encrypted) data to a stream splitter 4801. The corresponding error stream may be separated from the data stream (for example, the two streams may have been combined during compression but during decompression they are separated) or it may be received independently as a second data stream. Stream splitter 4801 applies XOR logical operations to each data block according to the error stream, reversing the original block conditioning process and restoring the original data on a block-by-block basis.

Figure 49:
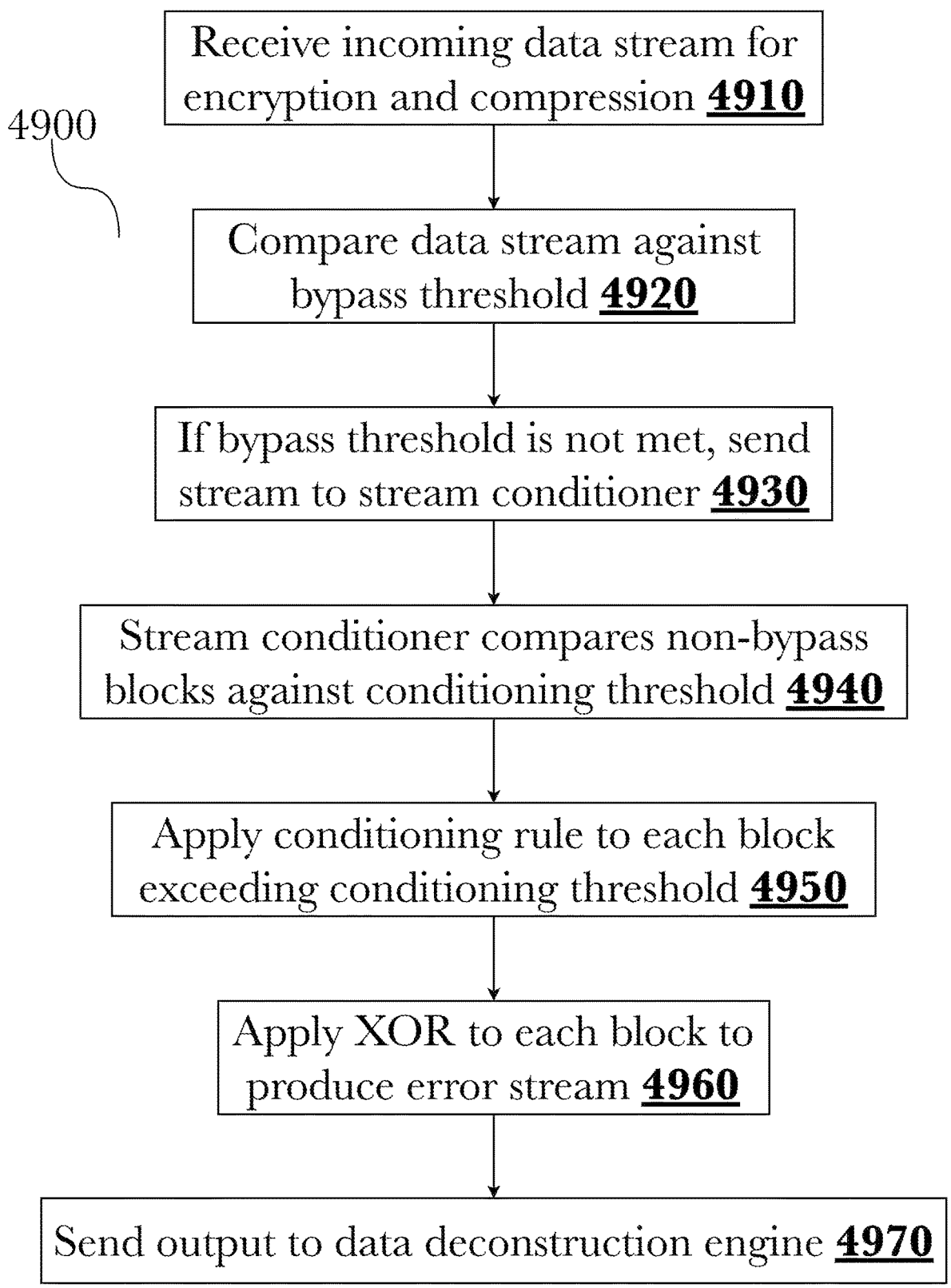
FIG. 49 is a flow diagram illustrating an exemplary method for compressing and encrypting data using split-stream processing.

FIG. 49 is a flow diagram illustrating an exemplary method 4900 for compressing and encrypting data using split-stream processing. In an initial step 4910, a data stream is received for compression and encryption. Each block in the data stream may be compared against a bypass threshold 4920 to determine whether the stream should be conditioned, and if so the stream is then passed 4930 to a stream conditioner 4702. The stream conditioner 4702 then compares each block 4940 against a conditioning threshold based on the block's actual vs. ideal frequency, and those blocks that exceed the threshold have a conditioning rule applied 4950. Each block may then be processed using an XOR logical operation 4960, and the output appended to an error stream that correspond to the difference between the original data and the conditioned data. The conditioned data and the error stream are then sent as output 4970 for compression as described in further detail below, with reference to at least FIG. 10.

Figure 50:
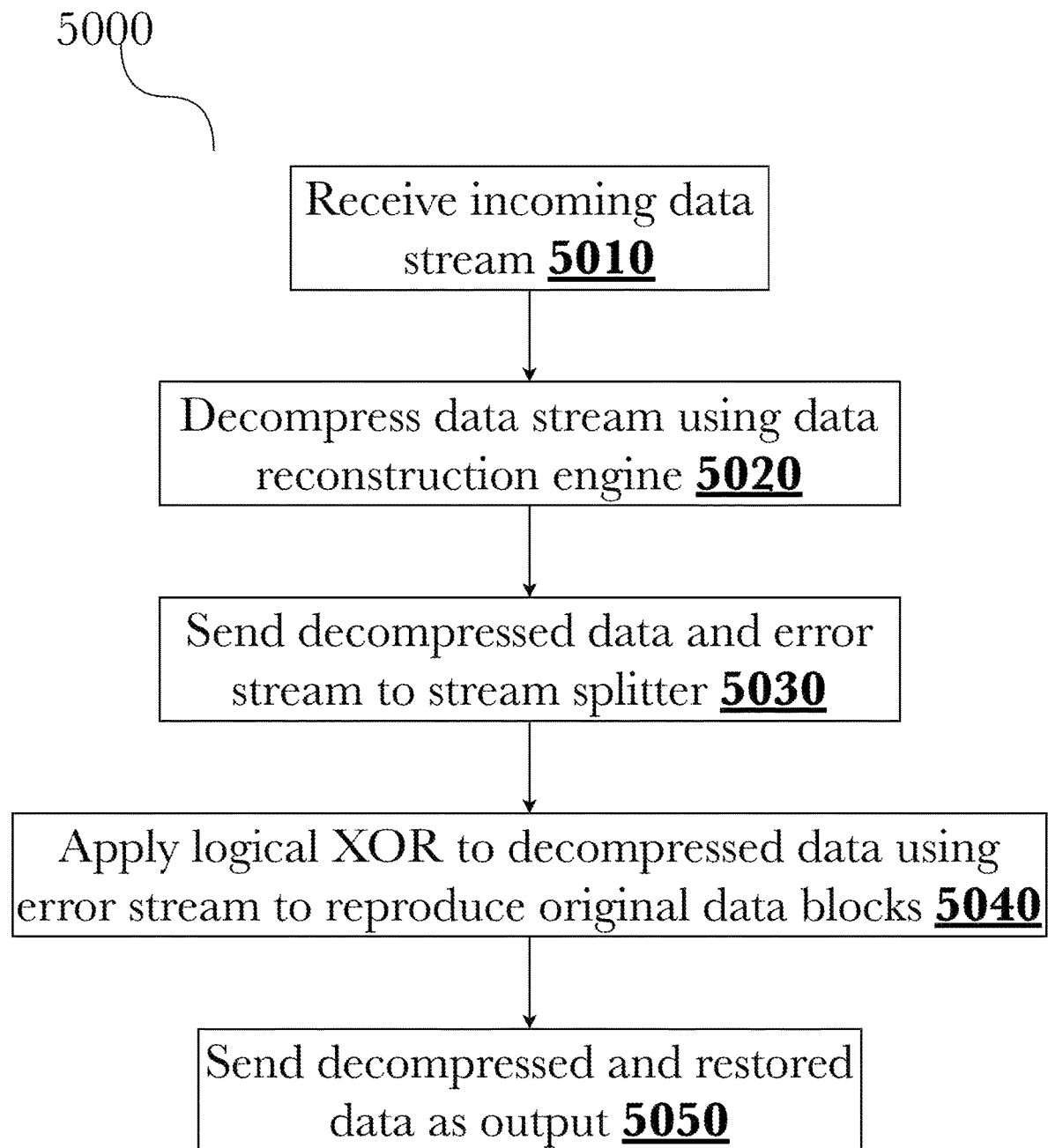
FIG. 50 is a flow diagram illustrating an exemplary method for decrypting and decompressing split-stream data.

FIG. 50 is a flow diagram illustrating an exemplary method 5000 for decrypting and decompressing split-stream data. In an initial step 5010, a data stream is received at a data decompression engine 301. The data stream is decompressed 5020 by reversing the encoding as described below with reference to FIG. 11, and the decompressed (but still encrypted) data and error stream are passed 5030 to a stream splitter 4801. The stream splitter performs logical XOR operations on each data block 5040 using the error stream, reversing any conditioning done to each data block, producing the original data as output 5050.

FIG. 1 is a diagram showing an embodiment 100 of the system in which all components of the system are operated locally. As incoming data 101 is received by data deconstruction engine 102. Data deconstruction engine 102 breaks the incoming data into sourceblocks, which are then sent to library manager 103. Using the information contained in sourceblock library lookup table 104 and sourceblock library storage 105, library manager 103 returns reference codes to data deconstruction engine 102 for processing into codewords, which are then stored in codeword storage 106. When a data retrieval request 107 is received, data reconstruction engine 108 obtains the codewords associated with the data from codeword storage 106, and sends them to library manager 103. Library manager 103 returns the appropriate sourceblocks to data reconstruction engine 108, which assembles them into the proper order and sends out the data in its original form 109.

Figure 2:
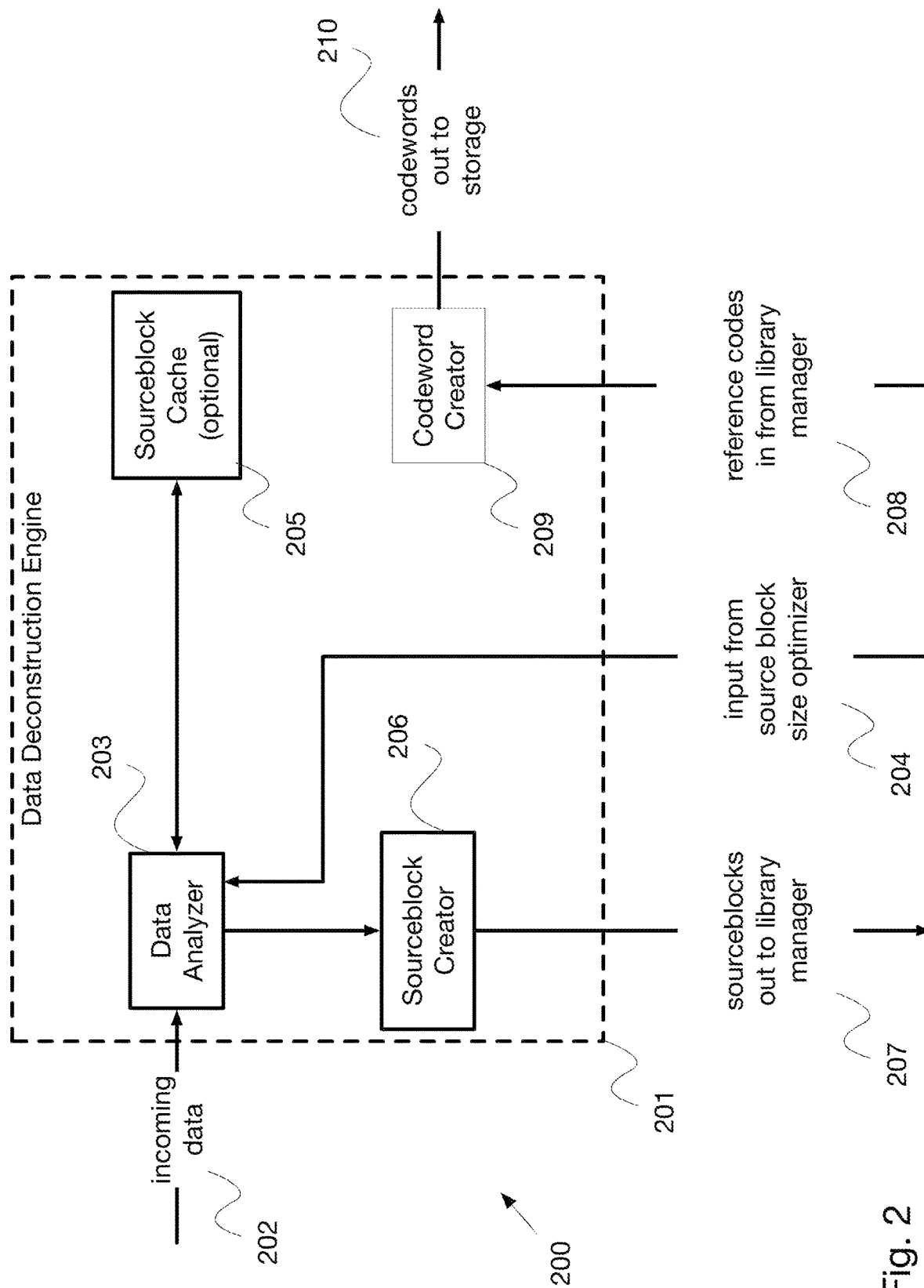
FIG. 2 is a diagram showing an embodiment of one aspect of the system, the data deconstruction engine.

FIG. 2 is a diagram showing an embodiment of one aspect 200 of the system, specifically data deconstruction engine 201. Incoming data 202 is received by data analyzer 203, which optimally analyzes the data based on machine learning algorithms and input 204 from a sourceblock size optimizer, which is disclosed below. Data analyzer may optionally have access to a sourceblock cache 205 of recently-processed sourceblocks, which can increase the speed of the system by avoiding processing in library manager 103. Based on information from data analyzer 203, the data is broken into sourceblocks by sourceblock creator 206, which sends sourceblocks 207 to library manager 203 for additional processing. Data deconstruction engine 201 receives reference codes 208 from library manager 103, corresponding to the sourceblocks in the library that match the sourceblocks sent by sourceblock creator 206, and codeword creator 209 processes the reference codes into codewords comprising a reference code to a sourceblock and a location of that sourceblock within the data set. The original data may be discarded, and the codewords representing the data are sent out to storage 210.

Figure 3:
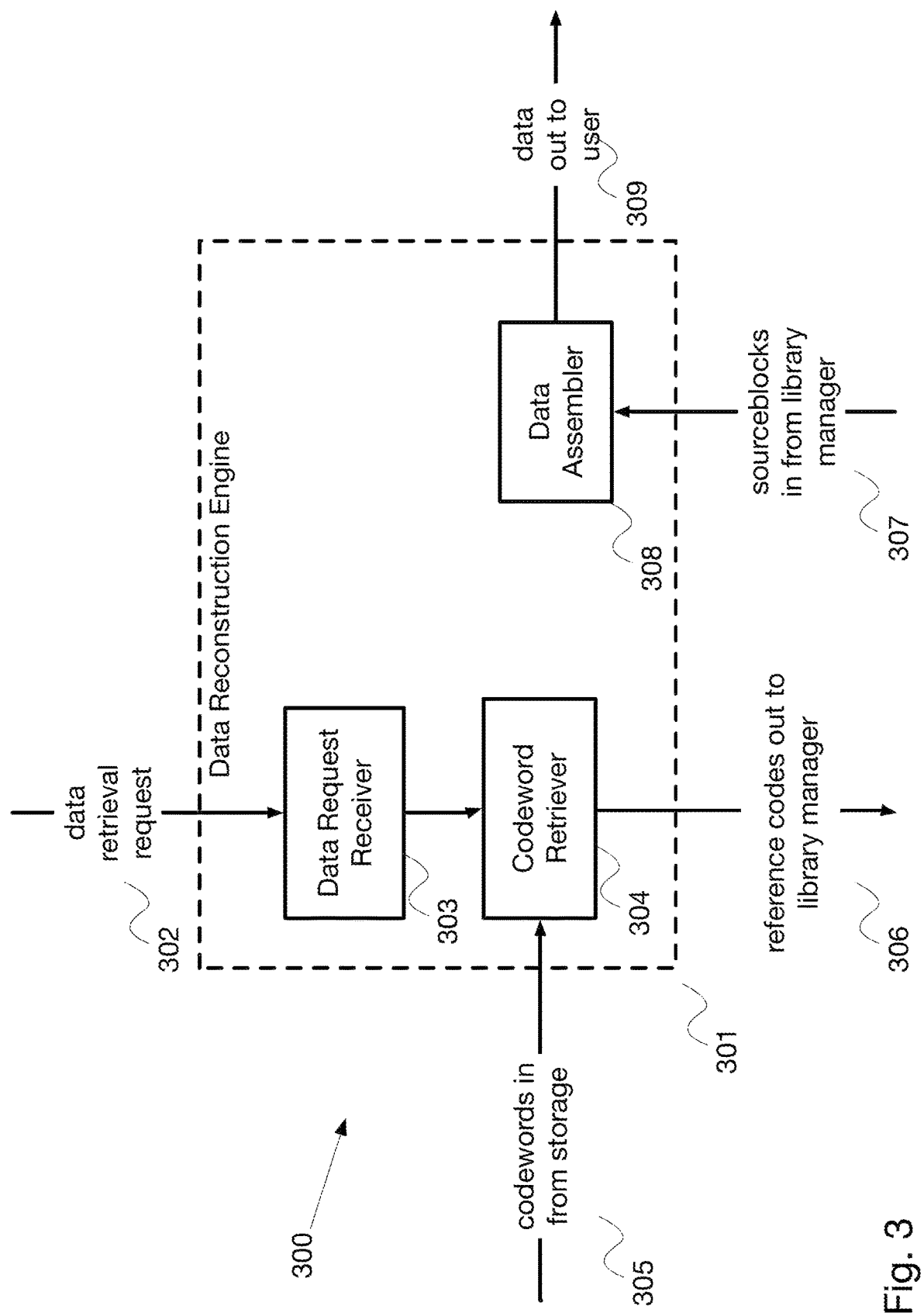
FIG. 3 is a diagram showing an embodiment of one aspect of the system, the data reconstruction engine.

FIG. 3 is a diagram showing an embodiment of another aspect of system 300, specifically data reconstruction engine 301. When a data retrieval request 302 is received by data request receiver 303 (in the form of a plurality of codewords corresponding to a desired final data set), it passes the information to data retriever 304, which obtains the requested data 305 from storage. Data retriever 304 sends, for each codeword received, a reference codes from the codeword 306 to library manager 103 for retrieval of the specific sourceblock associated with the reference code. Data assembler 308 receives the sourceblock 307 from library manager 103 and, after receiving a plurality of sourceblocks corresponding to a plurality of codewords, assembles them into the proper order based on the location information contained in each codeword (recall each codeword comprises a sourceblock reference code and a location identifier that specifies where in the resulting data set the specific sourceblock should be restored to. The requested data is then sent to user 309 in its original form.

Figure 4:
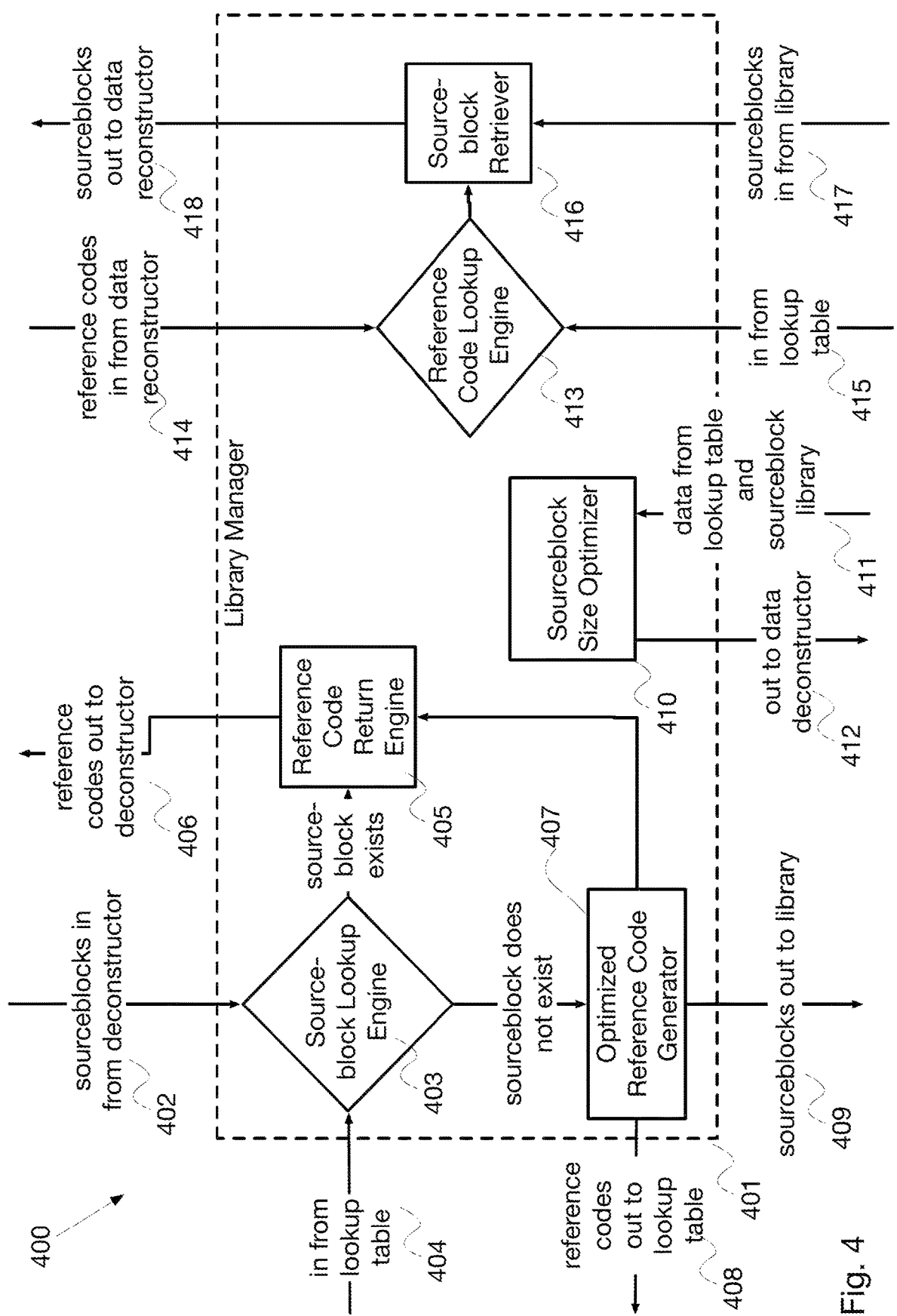
FIG. 4 is a diagram showing an embodiment of one aspect of the system, the library management module.

FIG. 4 is a diagram showing an embodiment of another aspect of the system 400, specifically library manager 401. One function of library manager 401 is to generate reference codes from sourceblocks received from data deconstruction engine 301. As sourceblocks are received 402 from data deconstruction engine 301, sourceblock lookup engine 403 checks sourceblock library lookup table 404 to determine whether those sourceblocks already exist in sourceblock library storage 105. If a particular sourceblock exists in sourceblock library storage 105, reference code return engine 405 sends the appropriate reference code 406 to data deconstruction engine 301. If the sourceblock does not exist in sourceblock library storage 105, optimized reference code generator 407 generates a new, optimized reference code based on machine learning algorithms. Optimized reference code generator 407 then saves the reference code 408 to sourceblock library lookup table 104; saves the associated sourceblock 409 to sourceblock library storage 105; and passes the reference code to reference code return engine 405 for sending 406 to data deconstruction engine 301. Another function of library manager 401 is to optimize the size of sourceblocks in the system. Based on information 411 contained in sourceblock library lookup table 104, sourceblock size optimizer 410 dynamically adjusts the size of sourceblocks in the system based on machine learning algorithms and outputs that information 412 to data analyzer 203. Another function of library manager 401 is to return sourceblocks associated with reference codes received from data reconstruction engine 301. As reference codes are received 414 from data reconstruction engine 301, reference code lookup engine 413 checks sourceblock library lookup table 415 to identify the associated sourceblocks; passes that information to sourceblock retriever 416, which obtains the sourceblocks 417 from sourceblock library storage 105; and passes them 418 to data reconstruction engine 301.

Figure 5:
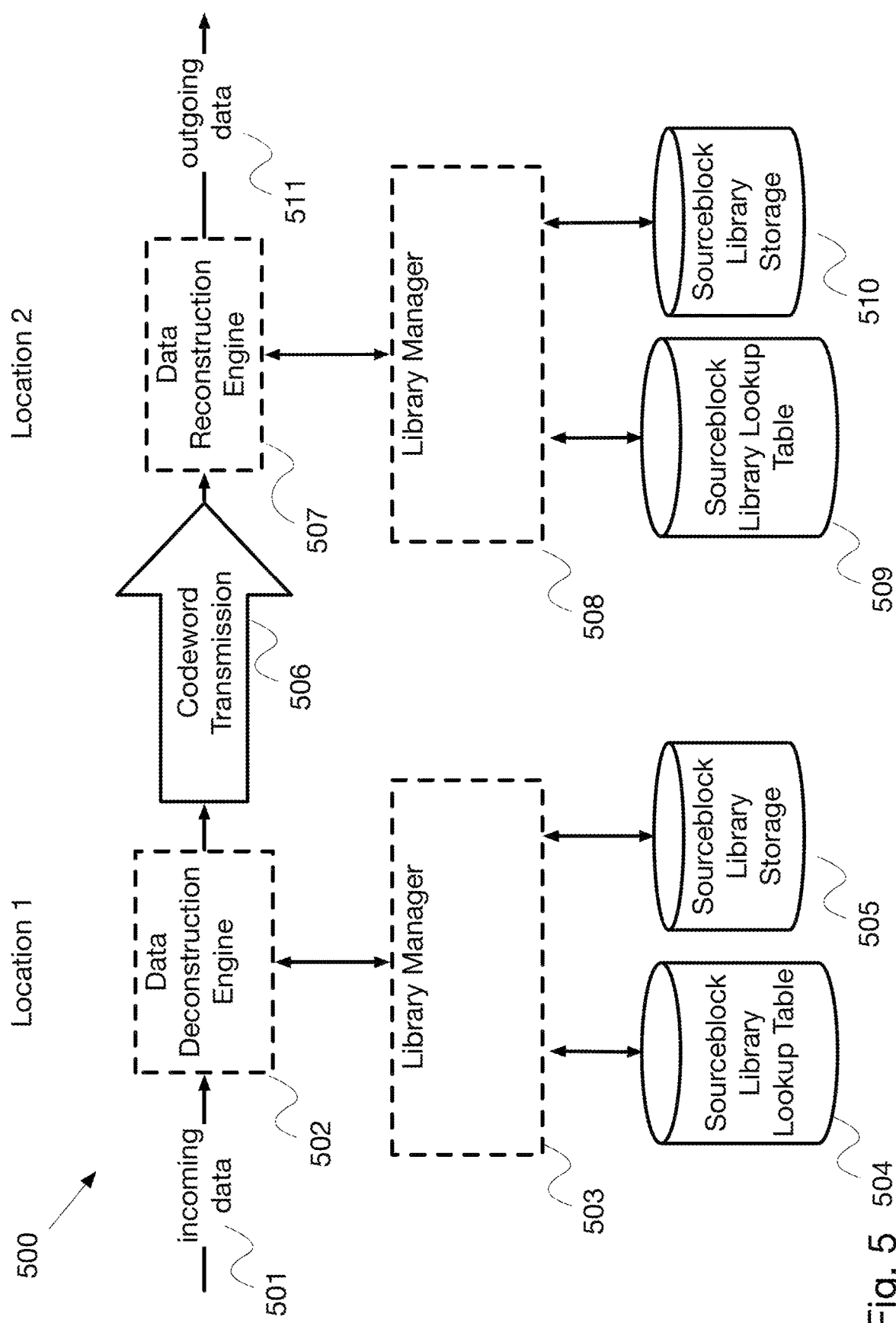
FIG. 5 is a diagram showing another embodiment of the system in which data is transferred between remote locations.

FIG. 5 is a diagram showing another embodiment of system 500, in which data is transferred between remote locations. As incoming data 501 is received by data deconstruction engine 502 at Location 1, data deconstruction engine 301 breaks the incoming data into sourceblocks, which are then sent to library manager 503 at Location 1. Using the information contained in sourceblock library lookup table 504 at Location 1 and sourceblock library storage 505 at Location 1, library manager 503 returns reference codes to data deconstruction engine 301 for processing into codewords, which are transmitted 506 to data reconstruction engine 507 at Location 2. In the case where the reference codes contained in a particular codeword have been newly generated by library manager 503 at Location 1, the codeword is transmitted along with a copy of the associated sourceblock. As data reconstruction engine 507 at Location 2 receives the codewords, it passes them to library manager module 508 at Location 2, which looks up the sourceblock in sourceblock library lookup table 509 at Location 2, and retrieves the associated from sourceblock library storage 510.

Where a sourceblock has been transmitted along with a codeword, the sourceblock is stored in sourceblock library storage 510 and sourceblock library lookup table 504 is updated. Library manager 503 returns the appropriate sourceblocks to data reconstruction engine 507, which assembles them into the proper order and sends the data in its original form 511.

Figure 6:
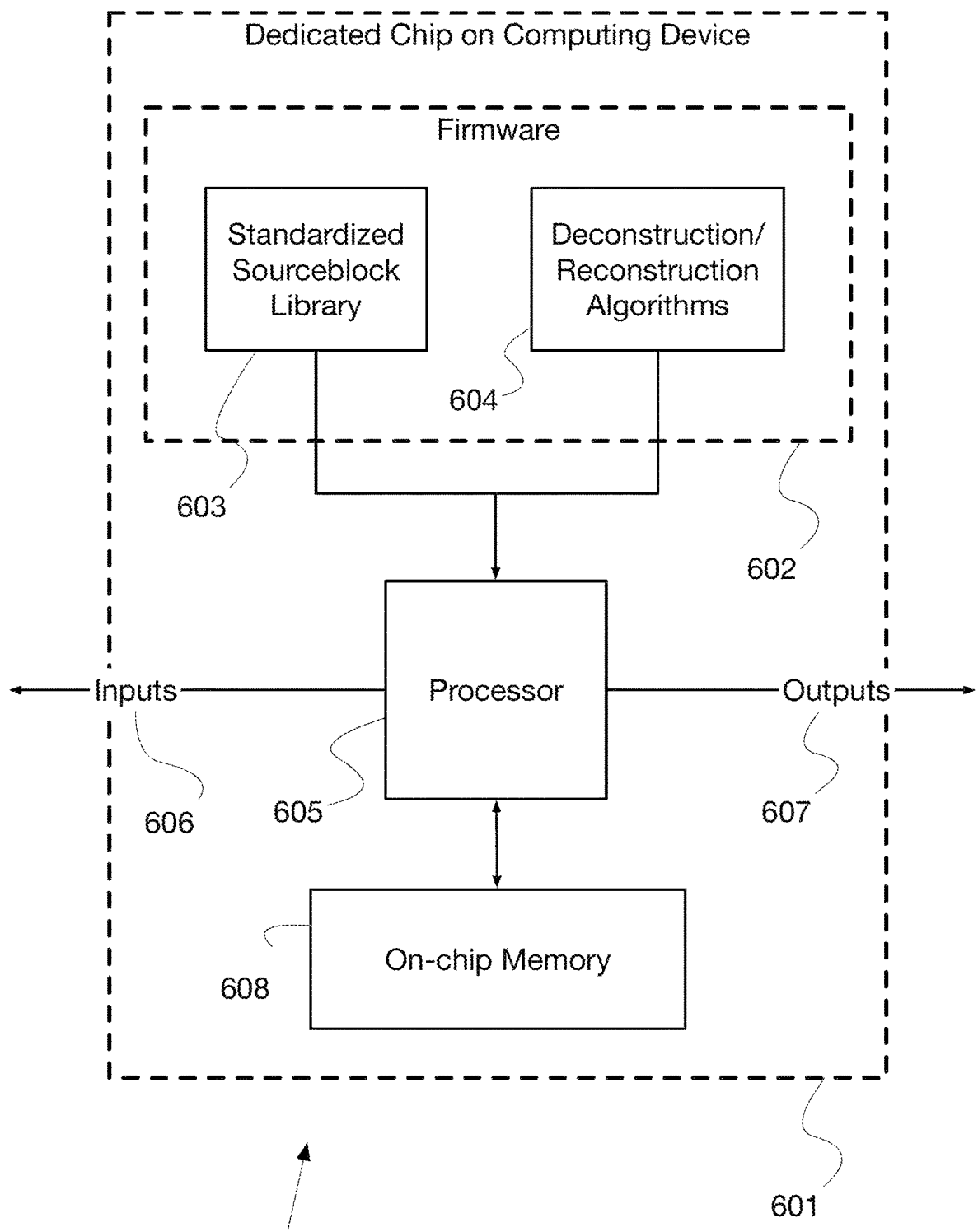
FIG. 6 is a diagram showing an embodiment in which a standardized version of the sourceblock library and associated algorithms would be encoded as firmware on a dedicated processing chip included as part of the hardware of a plurality of devices.

FIG. 6 is a diagram showing an embodiment 600 in which a standardized version of a sourceblock library 603 and associated algorithms 604 would be encoded as firmware 602 on a dedicated processing chip 601 included as part of the hardware of a plurality of devices 600. Contained on dedicated chip 601 would be a firmware area 602, on which would be stored a copy of a standardized sourceblock library 603 and deconstruction/reconstruction algorithms 604 for processing the data. Processor 605 would have both inputs 606 and outputs 607 to other hardware on the device 600. Processor 605 would store incoming data for processing on on-chip memory 608, process the data using standardized sourceblock library 603 and deconstruction/reconstruction algorithms 604, and send the processed data to other hardware on device 600. Using this embodiment, the encoding and decoding of data would be handled by dedicated chip 601, keeping the burden of data processing off device's 600 primary processors. Any device equipped with this embodiment would be able to store and transmit data in a highly optimized, bandwidth-efficient format with any other device equipped with this embodiment.

Figure 12:
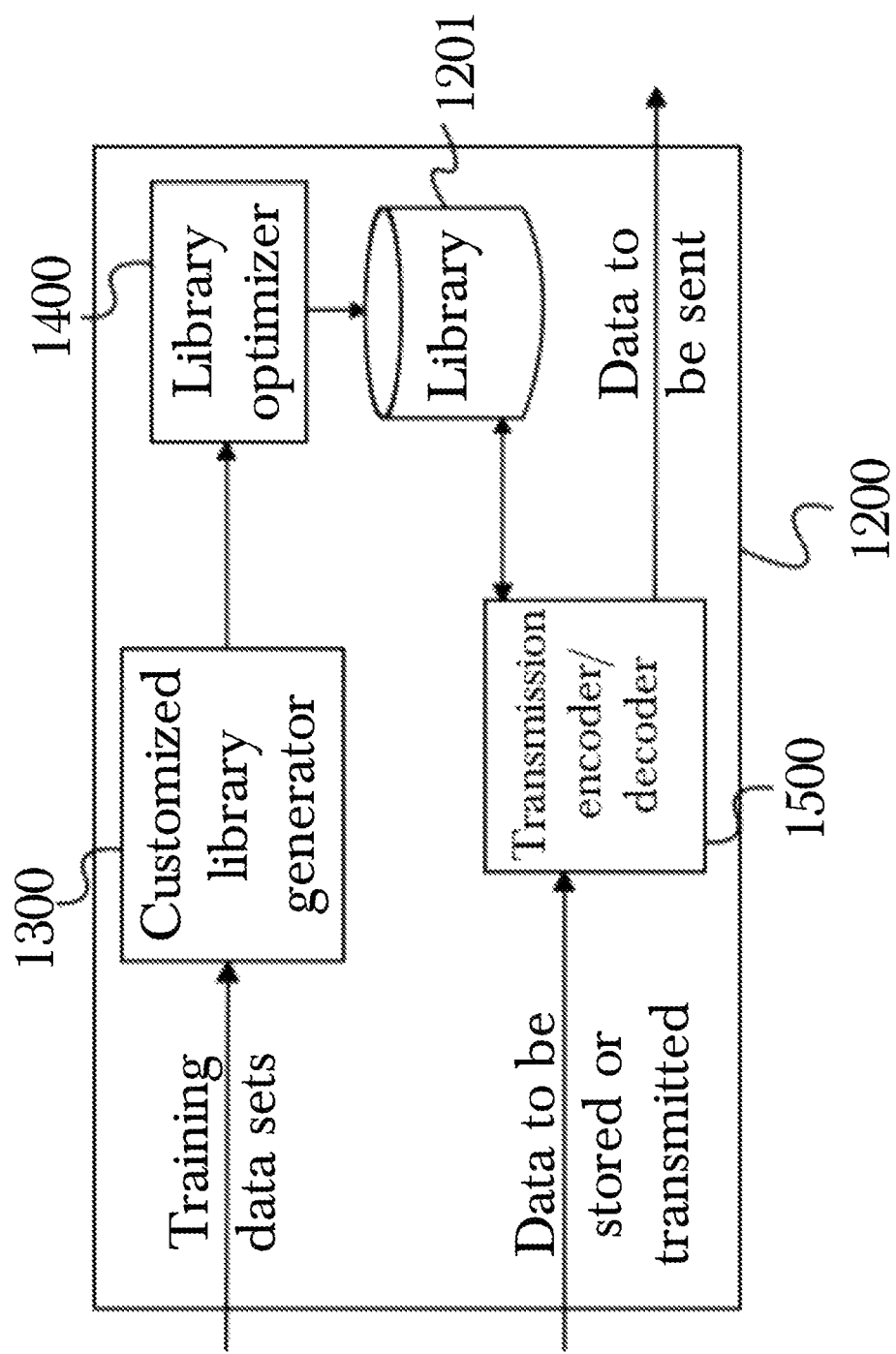
FIG. 12 is a diagram showing an exemplary system architecture, according to a preferred embodiment of the invention.

FIG. 12 is a diagram showing an exemplary system architecture 1200, according to a preferred embodiment of the invention. Incoming training data sets may be received at a customized library generator 1300 that processes training data to produce a customized word library 1201 comprising key-value pairs of data words (each comprising a string of bits) and their corresponding calculated binary Huffman codewords. The resultant word library 1201 may then be processed by a library optimizer 1400 to reduce size and improve efficiency, for example by pruning low-occurrence data entries or calculating approximate codewords that may be used to match more than one data word. A transmission encoder/decoder 1500 may be used to receive incoming data intended for storage or transmission, process the data using a word library 1201 to retrieve codewords for the words in the incoming data, and then append the codewords (rather than the original data) to an outbound data stream. Each of these components is described in greater detail below, illustrating the particulars of their respective processing and other functions, referring to FIGS. 2-4.

System 1200 provides near-instantaneous source coding that is dictionary-based and learned in advance from sample training data, so that encoding and decoding may happen concurrently with data transmission. This results in computational latency that is near zero but the data size reduction is comparable to classical compression. For example, if N bits are to be transmitted from sender to receiver, the compression ratio of classical compression is C, the ratio between the deflation factor of system 1200 and that of multi-pass source coding is p, the classical compression encoding rate is $R_C$ bit/s and the decoding rate is $R_D$ bit/s, and the transmission speed is S bit/s, the compress-send-decompress time will be $$T_{old} = \frac{N}{R_C} + \frac{N}{CS} + \frac{N}{CR_D}$$

while the transmit-while-coding time for system 1200 will be (assuming that encoding and decoding happen at least as quickly as network latency):

$$T_{new} = \frac{Np}{CS}$$

so that the total data transit time improvement factor is $$\frac{T_{old}}{T_{new}} = \frac{\frac{CS}{R_C} + 1 + \frac{S}{R_D}}{p}$$

which presents a savings whenever $$\frac{CS}{R_C} + \frac{S}{R_D} > p - 1.$$

This is a reasonable scenario given that typical values in real-world practice are $C = 0.32, R_C = 1.1 \cdot 10^{12}, R_D = 4.2 \cdot 10^{12},$ $$S = 10^{11}, \text{giving} \frac{CS}{R_C} + \frac{S}{R_D} = 0.053 \ldots,$$

such that system 1200 will outperform the total transit time of the best compression technology available as long as its deflation factor is no more than 5% worse than compression. Such customized dictionary-based encoding will also sometimes exceed the deflation ratio of classical compression, particularly when network speeds increase beyond 100 Gb/s.

The delay between data creation and its readiness for use at a receiving end will be equal to only the source word length t (typically 5-15 bytes), divided by the deflation factor C/p and the network speed S, i.e.

$$\text{delay}_{invention} = \frac{tp}{CS}$$

since encoding and decoding occur concurrently with data transmission. On the other hand, the latency associated with classical compression is $$\text{delay}_{priorart} = \frac{N}{R_C} + \frac{N}{CS} + \frac{N}{CR_D}$$

where N is the packet/file size. Even with the generous values chosen above as well as N=512K, t=10, and p=1.05, this results in $\text{delay}_{invention} \approx 3.3 \cdot 10^{-10}$ while $\text{delay}_{priorart} \approx 1.3 \cdot 10^{-7}$, a more than 400-fold reduction in latency.

A key factor in the efficiency of Huffman coding used by system 1200 is that key-value pairs be chosen carefully to minimize expected coding length, so that the average deflation/compression ratio is minimized. It is possible to achieve the best possible expected code length among all instantaneous codes using Huffman codes if one has access to the exact probability distribution of source words of a given desired length from the random variable generating them. In practice this is impossible, as data is received in a wide variety of formats and the random processes underlying the source data are a mixture of human input, unpredictable (though in principle, deterministic) physical events, and noise. System 1200 addresses this by restriction of data types and density estimation; training data is provided that is representative of the type of data anticipated in "real-world" use of system 1200, which is then used to model the distribution of binary strings in the data in order to build a Huffman code word library 1200.

Figure 13:
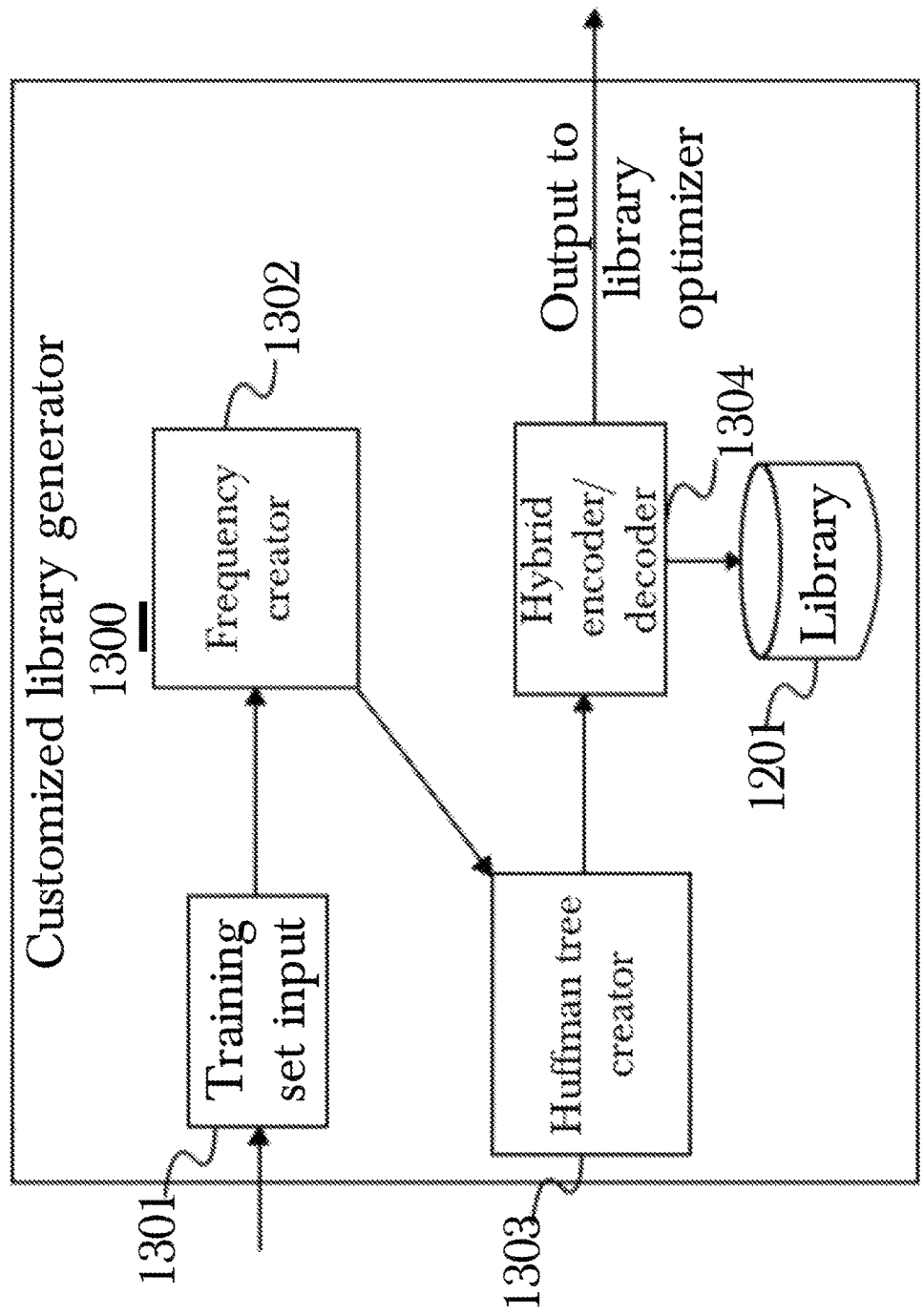
FIG. 13 is a diagram showing a more detailed architecture for a customized library generator.

FIG. 13 is a diagram showing a more detailed architecture for a customized library generator 1300. When an incoming training data set 1301 is received, it may be analyzed using a frequency creator 1302 to analyze for word frequency (that is, the frequency with which a given word occurs in the training data set). Word frequency may be analyzed by scanning all substrings of bits and directly calculating the frequency of each substring by iterating over the data set to produce an occurrence frequency, which may then be used to estimate the rate of word occurrence in non-training data. A first Huffman binary tree is created based on the frequency of occurrences of each word in the first dataset, and a Huffman codeword is assigned to each observed word in the first dataset according to the first Huffman binary tree. Machine learning may be utilized to improve results by processing a number of training data sets and using the results of each training set to refine the frequency estimations for non-training data, so that the estimation yield better results when used with real-world data (rather than, for example, being only based on a single training data set that may not be very similar to a received non-training data set). A second Huffman tree creator 1303 may be utilized to identify words that do not match any existing entries in a word library 1201 and pass them to a hybrid encoder/ decoder 1304, that then calculates a binary Huffman codeword for the mismatched word and adds the codeword and original data to the word library 1201 as a new key-value pair. In this manner, customized library generator 1300 may be used both to establish an initial word library 1201 from a first training set, as well as expand the word library 1201 using additional training data to improve operation.

Figure 14:
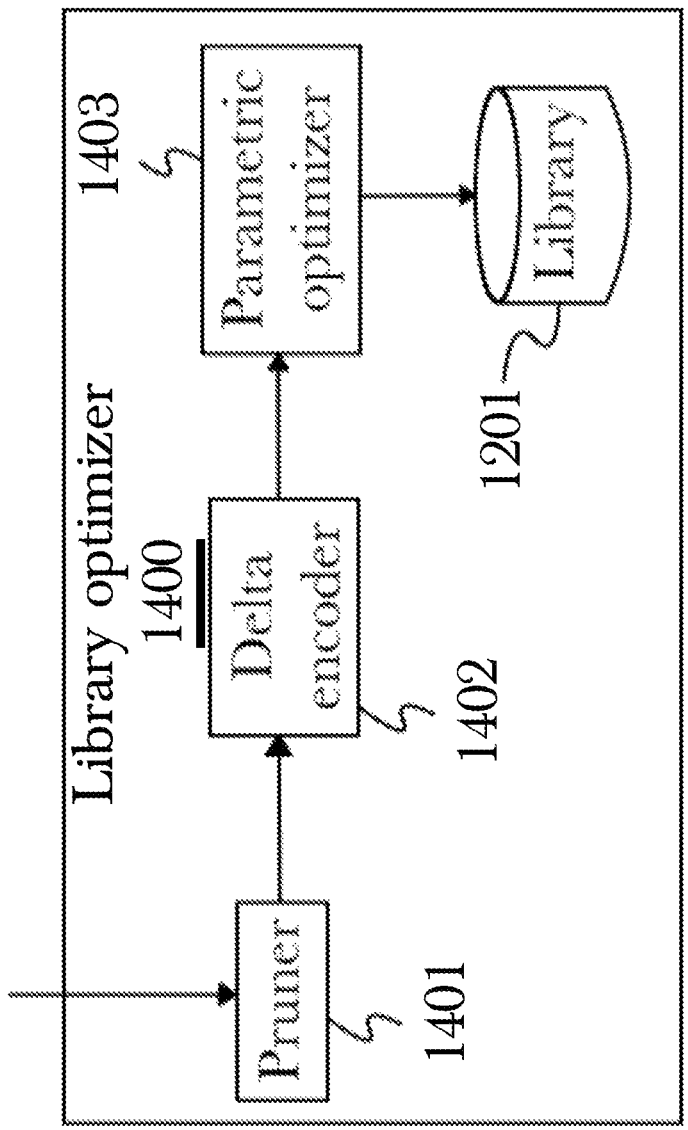
FIG. 14 is a diagram showing a more detailed architecture for a library optimizer.

FIG. 14 is a diagram showing a more detailed architecture for a library optimizer 1400. A pruner 1401 may be used to load a word library 1201 and reduce its size for efficient operation, for example by sorting the word library 1201 based on the known occurrence probability of each key-value pair and removing low-probability key-value pairs based on a loaded threshold parameter. This prunes low-value data from the word library to trim the size, eliminating large quantities of very-low-frequency key-value pairs such as single-occurrence words that are unlikely to be encountered again in a data set. Pruning eliminates the least-probable entries from word library 1201 up to a given threshold, which will have a negligible impact on the deflation factor since the removed entries are only the least-common ones, while the impact on word library size will be larger because samples drawn from asymptotically normal distributions (such as the log-probabilities of words generated by a probabilistic finite state machine, a model well-suited to a wide variety of real-world data) which occur in tails of the distribution are disproportionately large in counting measure. A delta encoder 1402 may be utilized to apply delta encoding to a plurality of words to store an approximate codeword as a value in the word library, for which each of the plurality of source words is a valid corresponding key. This may be used to reduce library size by replacing numerous key-value pairs with a single entry for the approximate codeword and then represent actual codewords using the approximate codeword plus a delta value representing the difference between the approximate codeword and the actual codeword. Approximate coding is optimized for low-weight sources such as Golomb coding, run-length coding, and similar techniques. The approximate source words may be chosen by locality-sensitive hashing, so as to approximate Hamming distance without incurring the intractability of nearest-neighbor-search in Hamming space. A parametric optimizer 1403 may load configuration parameters for operation to optimize the use of the word library 1201 during operation. Best-practice parameter/hyperparameter optimization strategies such as stochastic gradient descent, quasi-random grid search, and evolutionary search may be used to make optimal choices for all interdependent settings playing a role in the functionality of system 1200. In cases where lossless compression is not required, the delta value may be discarded at the expense of introducing some limited errors into any decoded (reconstructed) data.

Figure 15:
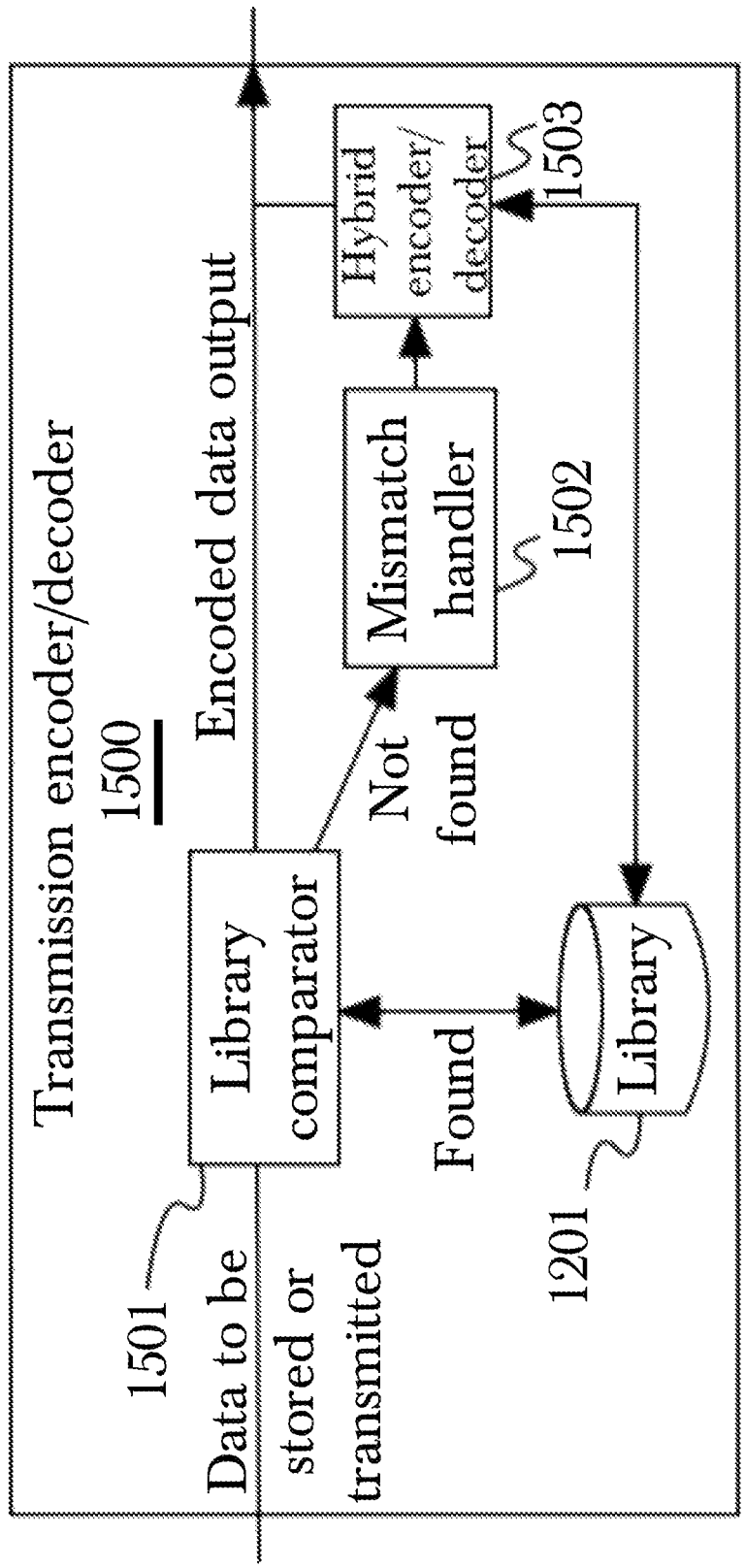
FIG. 15 is a diagram showing a more detailed architecture for a transmission and storage engine.

FIG. 15 is a diagram showing a more detailed architecture for a transmission encoder/decoder 1500. According to various arrangements, transmission encoder/decoder 1500 may be used to deconstruct data for storage or transmission, or to reconstruct data that has been received, using a word library 1201. A library comparator 1501 may be used to receive data comprising words or codewords, and compare against a word library 1201 by dividing the incoming stream into substrings of length t and using a fast hash to check word library 1201 for each substring. If a substring is found in word library 1201, the corresponding key/value (that is, the corresponding source word or codeword, according to whether the substring used in comparison was itself a word or codeword) is returned and appended to an output stream. If a given substring is not found in word library 1201, a mismatch handler 1502 and hybrid encoder/decoder 1503 may be used to handle the mismatch similarly to operation during the construction or expansion of word library 1201. A mismatch handler 1502 may be utilized to identify words that do not match any existing entries in a word library 1201 and pass them to a hybrid encoder/decoder 1503, that then calculates a binary Huffman codeword for the mismatched word and adds the codeword and original data to the word library 1201 as a new key-value pair. The newly-produced codeword may then be appended to the output stream. In arrangements where a mismatch indicator is included in a received data stream, this may be used to preemptively identify a substring that is not in word library 1201 (for example, if it was identified as a mismatch on the transmission end), and handled accordingly without the need for a library lookup.

Figure 19:
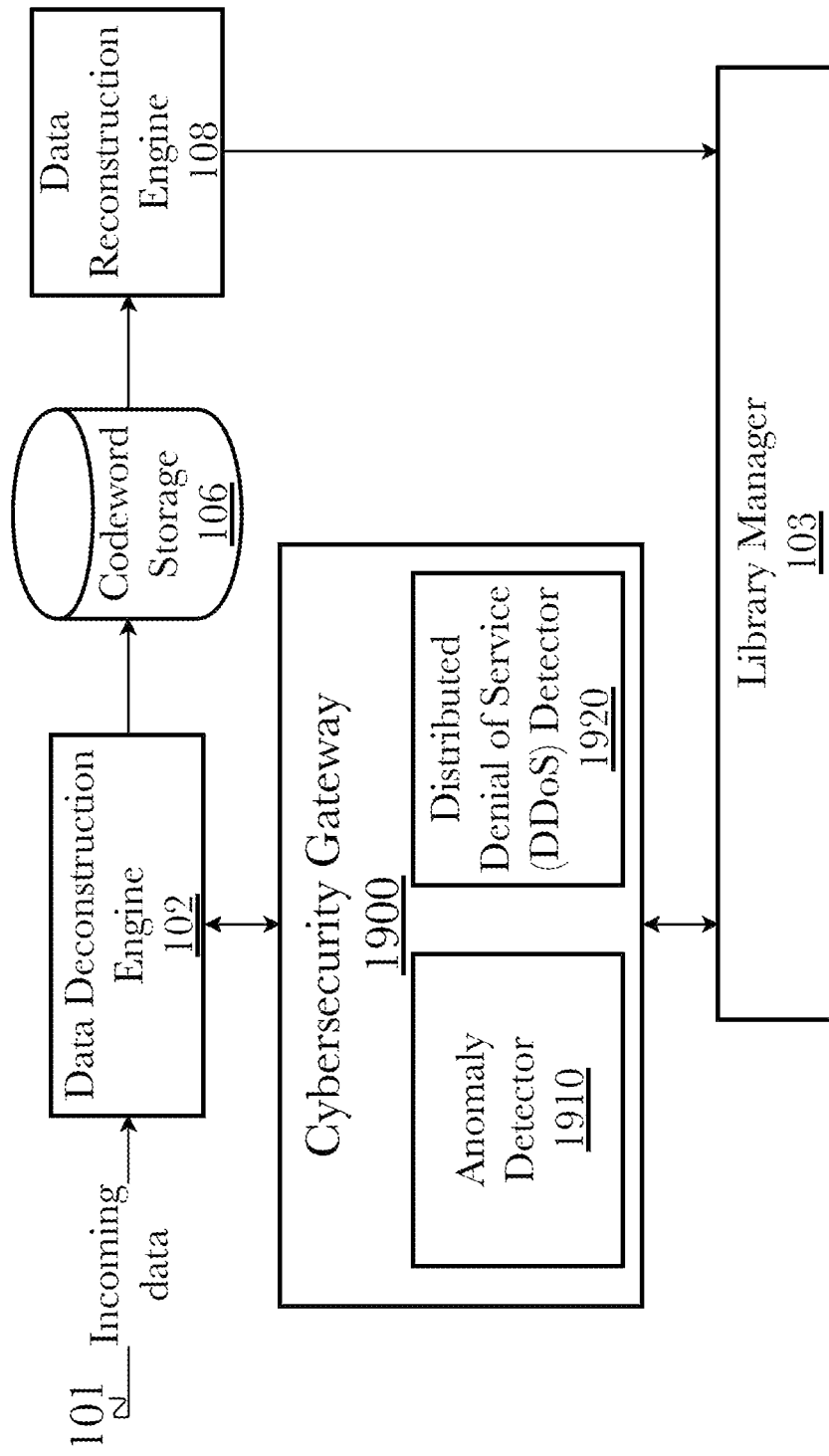
FIG. 19 is an exemplary system architecture of a data encoding system used for cyber security purposes.

FIG. 19 is an exemplary system architecture of a data encoding system used for cyber security purposes. Much like in FIG. 1, incoming data 101 to be deconstructed is sent to a data deconstruction engine 102, which may attempt to deconstruct the data and turn it into a collection of codewords using a library manager 103. Codeword storage 106 serves to store unique codewords from this process, and may be queried by a data reconstruction engine 108 which may reconstruct the original data from the codewords, using a library manager 103. However, a cybersecurity gateway 1900 is present, communicating in-between a library manager 103 and a deconstruction engine 102, and containing an anomaly detector 1910 and distributed denial of service (DDoS) detector 1920. The anomaly detector examines incoming data to determine whether there is a disproportionate number of incoming reference codes that do not match reference codes in the existing library. A disproportionate number of non-matching reference codes may indicate that data is being received from an unknown source, of an unknown type, or contains unexpected (possibly malicious) data. If the disproportionate number of non-matching reference codes exceeds an established threshold or persists for a certain length of time, the anomaly detector 1910 raises a warning to a system administrator. Likewise, the DDoS detector 1920 examines incoming data to determine whether there is a disproportionate amount of repetitive data. A disproportionate amount of repetitive data may indicate that a DDoS attack is in progress. If the disproportionate amount of repetitive data exceeds an established threshold or persists for a certain length of time, the DDoS detector 1910 raises a warning to a system administrator. In this way, a data encoding system may detect and warn users of, or help mitigate, common cyber-attacks that result from a flow of unexpected and potentially harmful data, or attacks that result from a flow of too much irrelevant data meant to slow down a network or system, as in the case of a DDoS attack.

Figure 22:
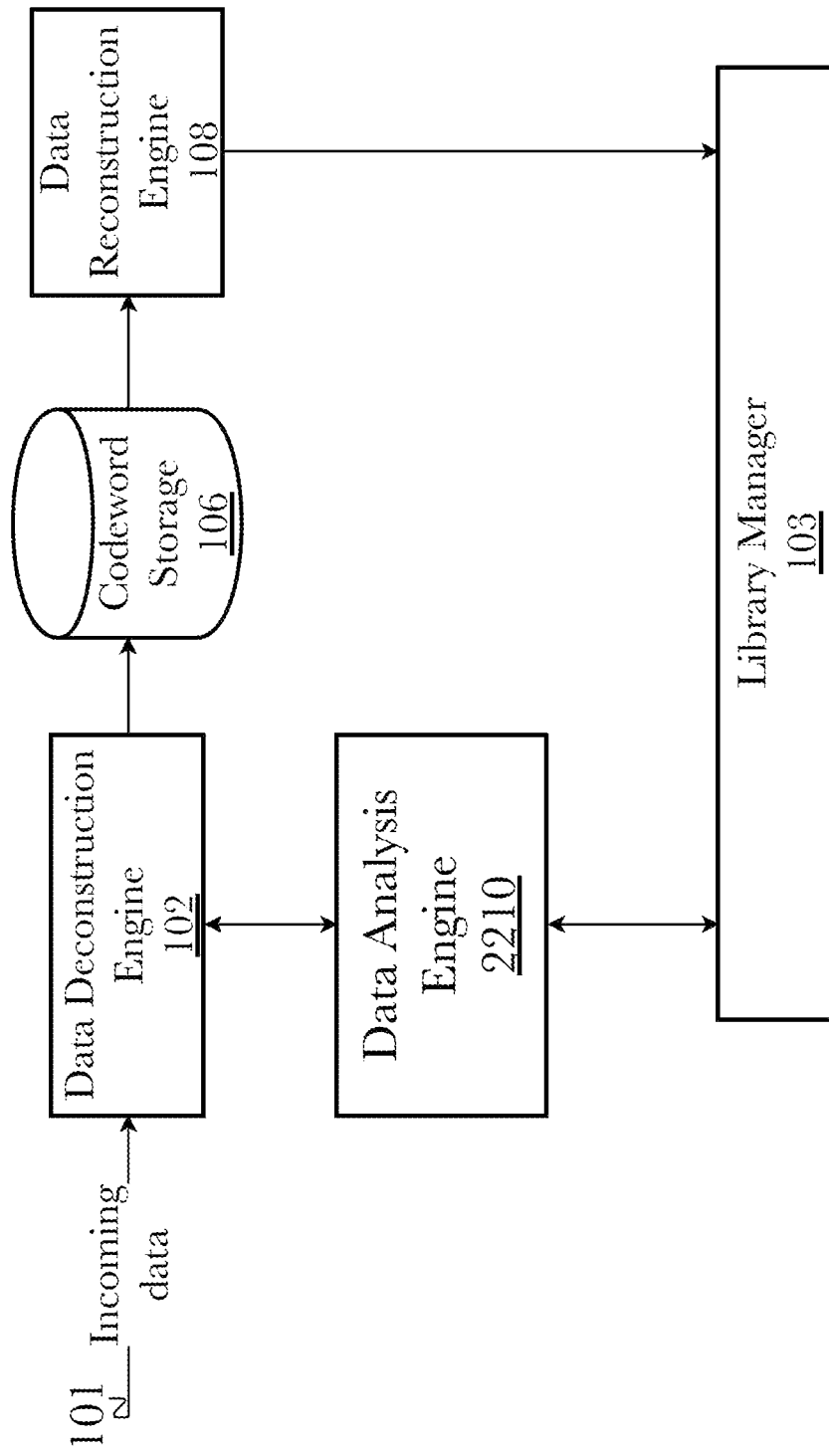
FIG. 22 is an exemplary system architecture of a data encoding system used for data mining and analysis purposes.

FIG. 22 is an exemplary system architecture of a data encoding system used for data mining and analysis purposes. Much like in FIG. 1, incoming data 101 to be deconstructed is sent to a data deconstruction engine 102, which may attempt to deconstruct the data and turn it into a collection of codewords using a library manager 103. Codeword storage 106 serves to store unique codewords from this process, and may be queried by a data reconstruction engine 108 which may reconstruct the original data from the codewords, using a library manager 103. A data analysis engine 2210, typically operating while the system is otherwise idle, sends requests for data to the data reconstruction engine 108, which retrieves the codewords representing the requested data from codeword storage 106, reconstructs them into the data represented by the codewords, and send the reconstructed data to the data analysis engine 2210 for analysis and extraction of useful data (i.e., data mining). Because the speed of reconstruction is significantly faster than decompression using traditional compression technologies (i.e., significantly less decompression latency), this approach makes data mining feasible. Very often, data stored using traditional compression is not mined precisely because decompression lag makes it unfeasible, especially during shorter periods of system idleness. Increasing the speed of data reconstruction broadens the circumstances under which data mining of stored data is feasible.

Figure 24:
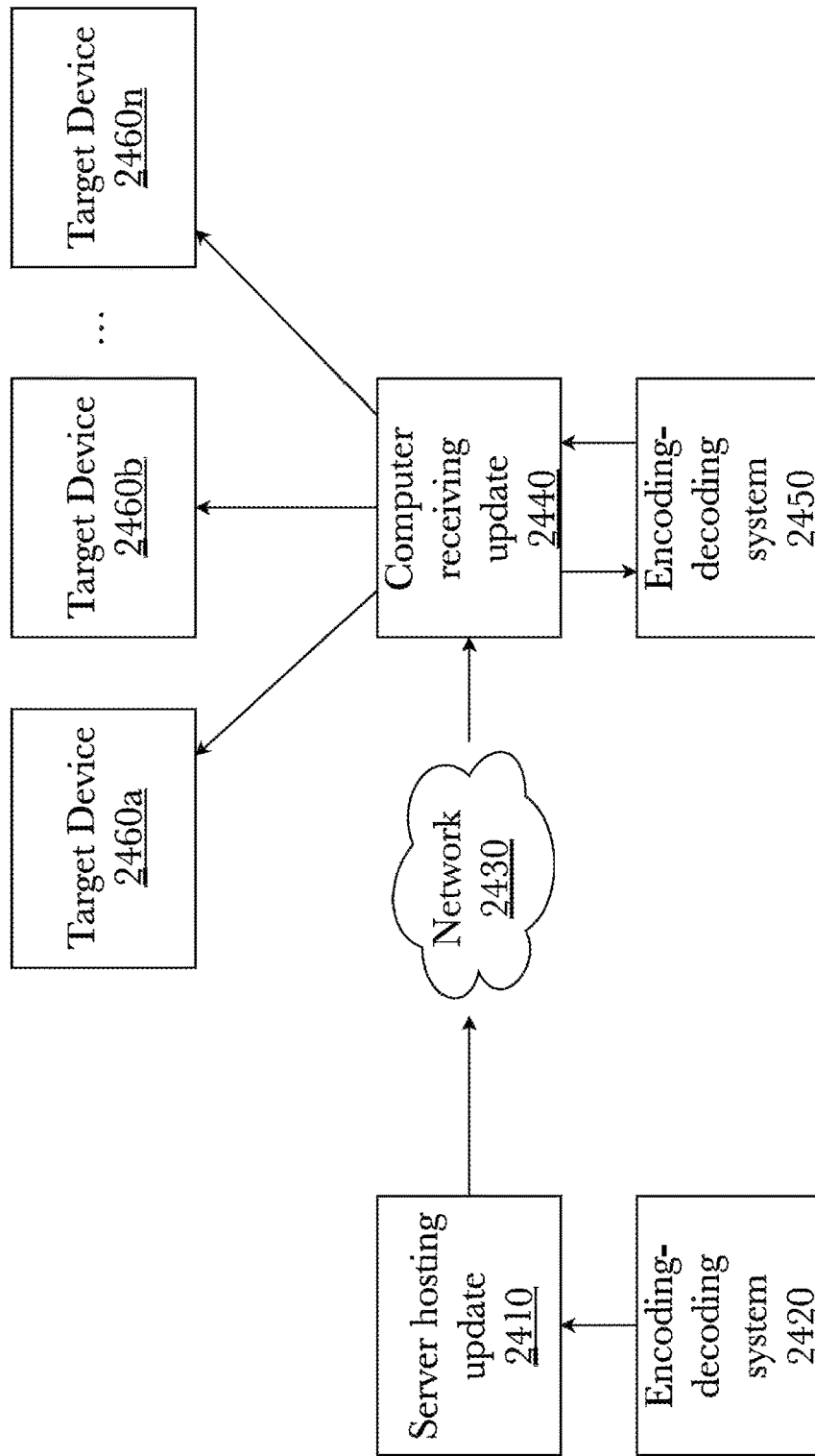
FIG. 24 is an exemplary system architecture of a data encoding system used for remote software and firmware updates.

FIG. 24 is an exemplary system architecture of a data encoding system used for remote software and firmware updates. Software and firmware updates typically require smaller, but more frequent, file transfers. A server which hosts a software or firmware update 2410 may host an encoding-decoding system 2420, allowing for data to be encoded into, and decoded from, sourceblocks or codewords, as disclosed in previous figures. Such a server may possess a software update, operating system update, firmware update, device driver update, or any other form of software update, which in some cases may be minor changes to a file, but nevertheless necessitate sending the new, completed file to the recipient. Such a server is connected over a network 2430, which is further connected to a recipient computer 2440, which may be connected to a server 2410 for receiving such an update to its system. In this instance, the recipient device 2440 also hosts the encoding and decoding system 2450, along with a codebook or library of reference codes that the hosting server 2410 also shares. The updates are retrieved from storage at the hosting server 2410 in the form of codewords, transferred over the network 2430 in the form of codewords, and reconstructed on the receiving computer 2440. In this way, a far smaller file size, and smaller total update size, may be sent over a network. The receiving computer 2440 may then install the updates on any number of target computing devices 2460*a-n*, using a local network or other high-bandwidth connection.

Figure 26:
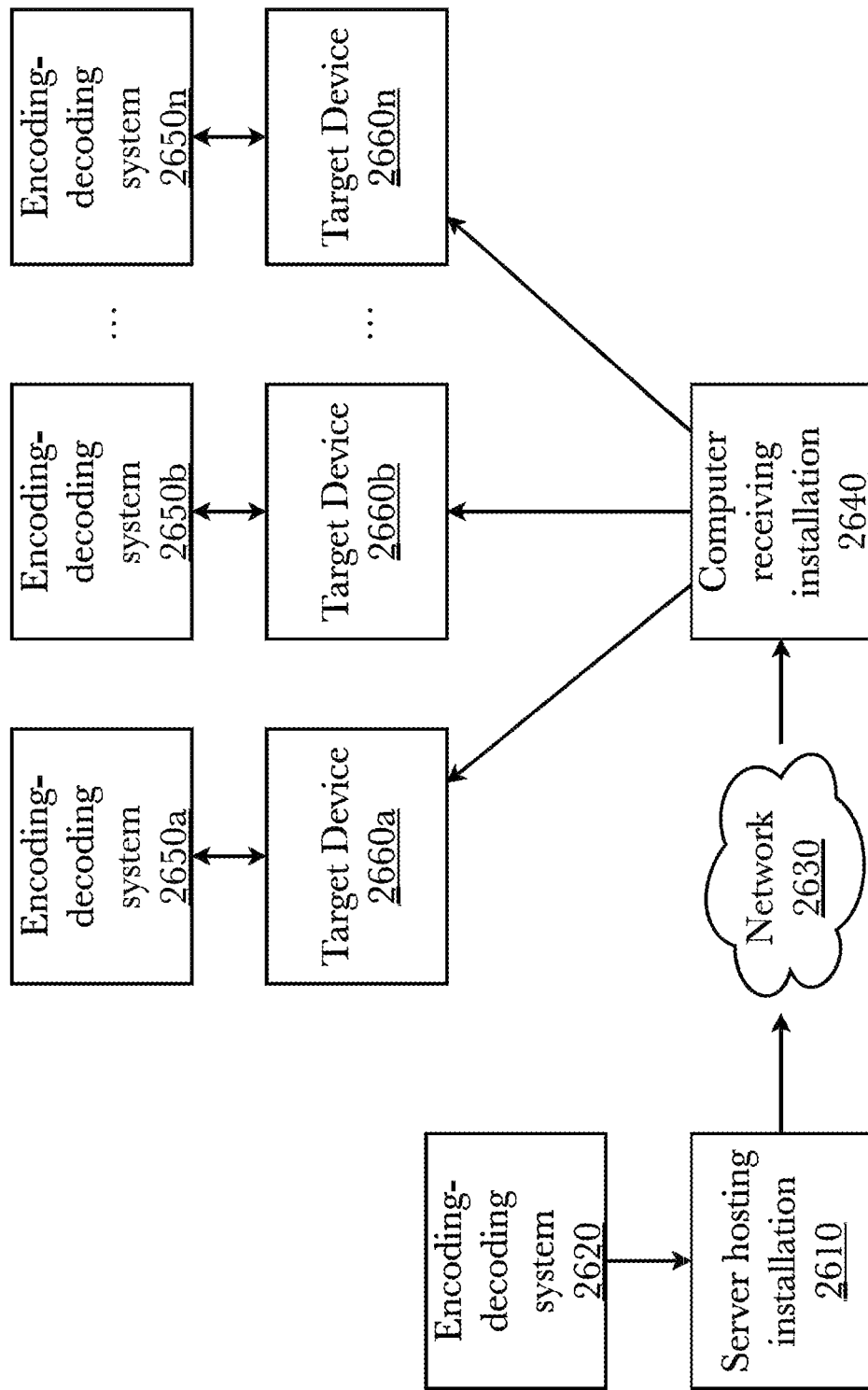
FIG. 26 is an exemplary system architecture of a data encoding system used for large-scale software installation such as operating systems.

FIG. 26 is an exemplary system architecture of a data encoding system used for large-scale software installation such as operating systems. Large-scale software installations typically require very large, but infrequent, file transfers. A server which hosts an installable software 2610 may host an encoding-decoding system 2620, allowing for data to be encoded into, and decoded from, sourceblocks or codewords, as disclosed in previous figures. The files for the large scale software installation are hosted on the server 2610, which is connected over a network 2630 to a recipient computer 2640. In this instance, the encoding and decoding system 2650*a-n* is stored on or connected to one or more target devices 2660*a-n*, along with a codebook or library of reference codes that the hosting server 2610 shares. The software is retrieved from storage at the hosting server 2610 in the form of codewords, and transferred over the network 2630 in the form of codewords to the receiving computer 2640. However, instead of being reconstructed at the receiving computer 2640, the codewords are transmitted to one or more target computing devices, and reconstructed and installed directly on the target devices 2660*a-n*. In this way, a far smaller file size, and smaller total update size, may be sent over a network or transferred between computing devices, even where the network 2630 between the receiving computer 2640 and target devices 2660*a-n* is low bandwidth, or where there are many target devices 2660*a-n*.

Figure 28:
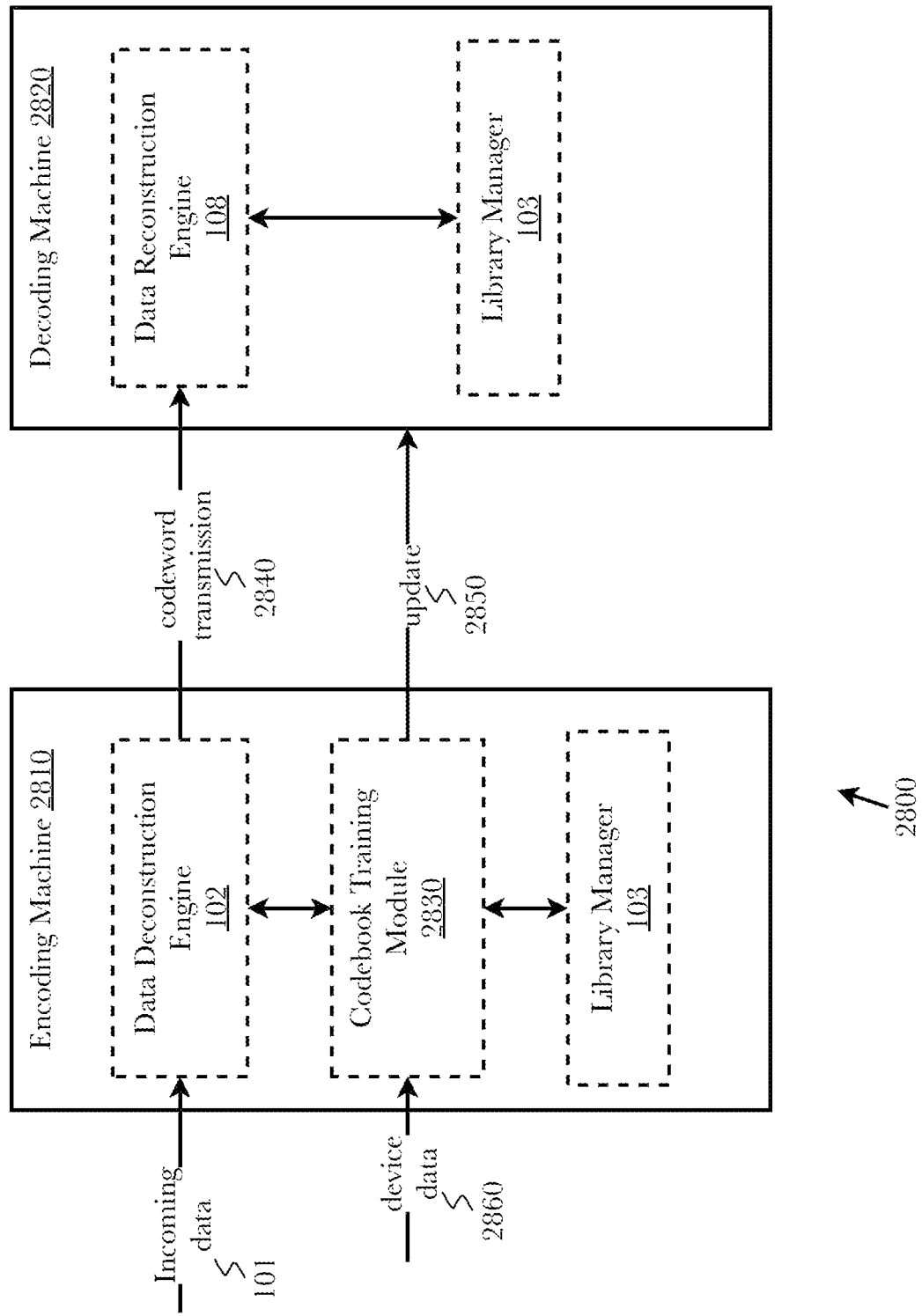
FIG. 28 is a block diagram of an exemplary system architecture of a codebook training system for a data encoding system, according to an embodiment.

FIG. 28 is a block diagram of an exemplary system architecture 2800 of a codebook training system for a data encoding system, according to an embodiment. According to this embodiment, two separate machines may be used for encoding 2810 and decoding 2820. Much like in FIG. 1, incoming data 101 to be deconstructed is sent to a data deconstruction engine 102 residing on encoding machine 2810, which may attempt to deconstruct the data and turn it into a collection of codewords using a library manager 103. Codewords may be transmitted 2840 to a data reconstruction engine 108 residing on decoding machine 2820, which may reconstruct the original data from the codewords, using a library manager 103. However, according to this embodiment, a codebook training module 2830 is present on the decoding machine 2810, communicating in-between a library manager 103 and a deconstruction engine 102. According to other embodiments, codebook training module 2830 may reside instead on decoding machine 2820 if the machine has enough computing resources available; which machine the module 2830 is located on may depend on the system user's architecture and network structure. Codebook training module 2830 may send requests for data to the data reconstruction engine 2810, which routes incoming data 101 to codebook training module 2830. Codebook training module 2830 may perform analyses on the requested data in order to gather information about the distribution of incoming data 101 as well as monitor the encoding/decoding model performance. Additionally, codebook training module 2830 may also request and receive device data 2860 to supervise network connected devices and their processes and, according to some embodiments, to allocate training resources when requested by devices running the encoding system. Devices may include, but are not limited to, encoding and decoding machines, training machines, sensors, mobile computing devices, and Internet-of-things ("IoT") devices. Based on the results of the analyses, the codebook training module 2830 may create a new training dataset from a subset of the requested data in order to counteract the effects of data drift on the encoding/decoding models, and then publish updated 2850 codebooks to both the encoding machine 2810 and decoding machine 2820.

Figure 29:
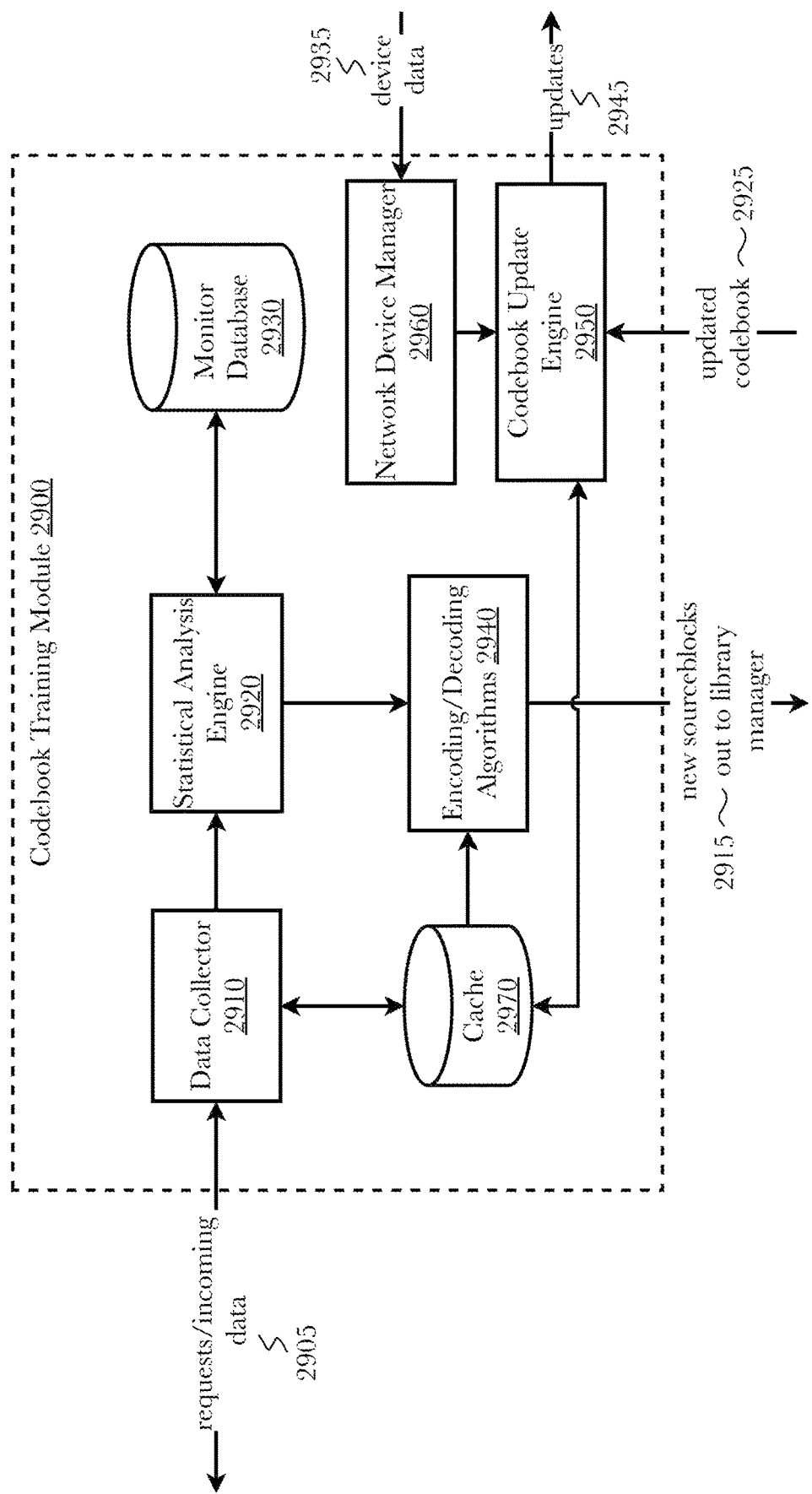
FIG. 29 is a block diagram of an exemplary architecture for a codebook training module, according to an embodiment.

FIG. 29 is a block diagram of an exemplary architecture for a codebook training module 2900, according to an embodiment. According to the embodiment, a data collector 2910 is present which may send requests for incoming data 2905 to a data deconstruction engine 102 which may receive the request and route incoming data to codebook training module 2900 where it may be received by data collector 2910. Data collector 2910 may be configured to request data periodically such as at schedule time intervals, or for example, it may be configured to request data after a certain amount of data has been processed through the encoding machine 2810 or decoding machine 2820. The received data may be a plurality of sourceblocks, which are a series of binary digits, originating from a source packet otherwise referred to as a datagram. The received data may compiled into a test dataset and temporarily stored in a cache 2970. Once stored, the test dataset may be forwarded to a statistical analysis engine 2920 which may utilize one or more algorithms to determine the probability distribution of the test dataset. Best-practice probability distribution algorithms such as Kullback-Leibler divergence, adaptive windowing, and Jensen-Shannon divergence may be used to compute the probability distribution of training and test datasets. A monitoring database 2930 may be used to store a variety of statistical data related to training datasets and model performance metrics in one place to facilitate quick and accurate system monitoring capabilities as well as assist in system debugging functions. For example, the original or current training dataset and the calculated probability distribution of this training dataset used to develop the current encoding and decoding algorithms may be stored in monitor database 2930.

Since data drifts involve statistical change in the data, the best approach to detect drift is by monitoring the incoming data's statistical properties, the model's predictions, and their correlation with other factors. After statistical analysis engine 2920 calculates the probability distribution of the test dataset it may retrieve from monitor database 2930 the calculated and stored probability distribution of the current training dataset. It may then compare the two probability distributions of the two different datasets in order to verify if the difference in calculated distributions exceeds a predetermined difference threshold. If the difference in distributions does not exceed the difference threshold, that indicates the test dataset, and therefore the incoming data, has not experienced enough data drift to cause the encoding/decoding system performance to degrade significantly, which indicates that no updates are necessary to the existing codebooks. However, if the difference threshold has been surpassed, then the data drift is significant enough to cause the encoding/decoding system performance to degrade to the point where the existing models and accompanying codebooks need to be updated. According to an embodiment, an alert may be generated by statistical analysis engine 2920 if the difference threshold is surpassed or if otherwise unexpected behavior arises.

In the event that an update is required, the test dataset stored in the cache 2970 and its associated calculated probability distribution may be sent to monitor database 2930 for long term storage. This test dataset may be used as a new training dataset to retrain the encoding and decoding algorithms 2940 used to create new sourceblocks based upon the changed probability distribution. The new sourceblocks may be sent out to a library manager 2915 where the sourceblocks can be assigned new codewords. Each new sourceblock and its associated codeword may then be added to a new codebook and stored in a storage device. The new and updated codebook may then be sent back 2925 to codebook training module 2900 and received by a codebook update engine 2950. Codebook update engine 2950 may temporarily store the received updated codebook in the cache 2970 until other network devices and machines are ready, at which point codebook update engine 2950 will publish the updated codebooks 2945 to the necessary network devices.

A network device manager 2960 may also be present which may request and receive network device data 2935 from a plurality of network connected devices and machines. When the disclosed encoding system and codebook training system 2800 are deployed in a production environment, upstream process changes may lead to data drift, or other unexpected behavior. For example, a sensor being replaced that changes the units of measurement from inches to centimeters, data quality issues such as a broken sensor always reading 0, and covariate shift which occurs when there is a change in the distribution of input variables from the training set. These sorts of behavior and issues may be determined from the received device data 2935 in order to identify potential causes of system error that is not related to data drift and therefore does not require an updated codebook. This can save network resources from being unnecessarily used on training new algorithms as well as alert system users to malfunctions and unexpected behavior devices connected to their networks. Network device manager 2960 may also utilize device data 2935 to determine available network resources and device downtime or periods of time when device usage is at its lowest. Codebook update engine 2950 may request network and device availability data from network device manager 2960 in order to determine the most optimal time to transmit updated codebooks (i.e., trained libraries) to encoder and decoder devices and machines.

Figure 30:
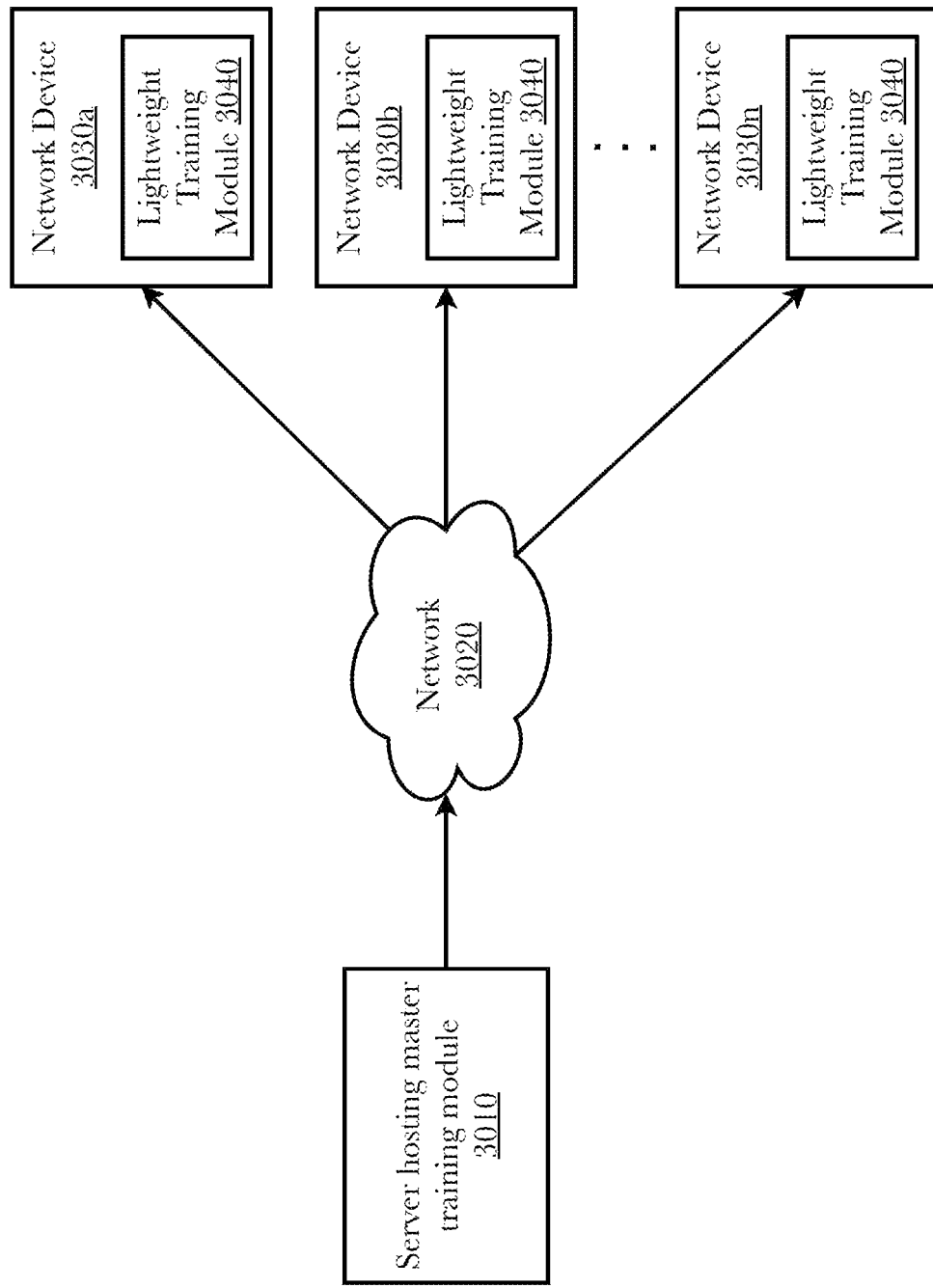
FIG. 30 is a block diagram of another embodiment of the codebook training system using a distributed architecture and a modified training module.

FIG. 30 is a block diagram of another embodiment of the codebook training system using a distributed architecture and a modified training module. According to an embodiment, there may be a server which maintains a master supervisory process over remote training devices hosting a master training module 3010 which communicates via a network 3020 to a plurality of connected network devices 3030*a-n*. The server may be located at the remote training end such as, but not limited to, cloud-based resources, a user-owned data center, etc. The master training module located on the server operates similarly to the codebook training module disclosed in FIG. 29 above, however, the server 3010 utilizes the master training module via the network device manager 2960 to farm out training resources to network devices 3030*a-n*. The server 3010 may allocate resources in a variety of ways, for example, round-robin, priority-based, or other manner, depending on the user needs, costs, and number of devices running the encoding/decoding system. Server 3010 may identify elastic resources which can be employed if available to scale up training when the load becomes too burdensome. On the network devices 3030*a-n* may be present a lightweight version of the training module 3040 that trades a little suboptimality in the codebook for training on limited machinery and/or makes training happen in low-priority threads to take advantage of idle time. In this way the training of new encoding/decoding algorithms may take place in a distributed manner which allows data gathering or generating devices to process and train on data gathered locally, which may improve system latency and optimize available network resources.

Figure 32:
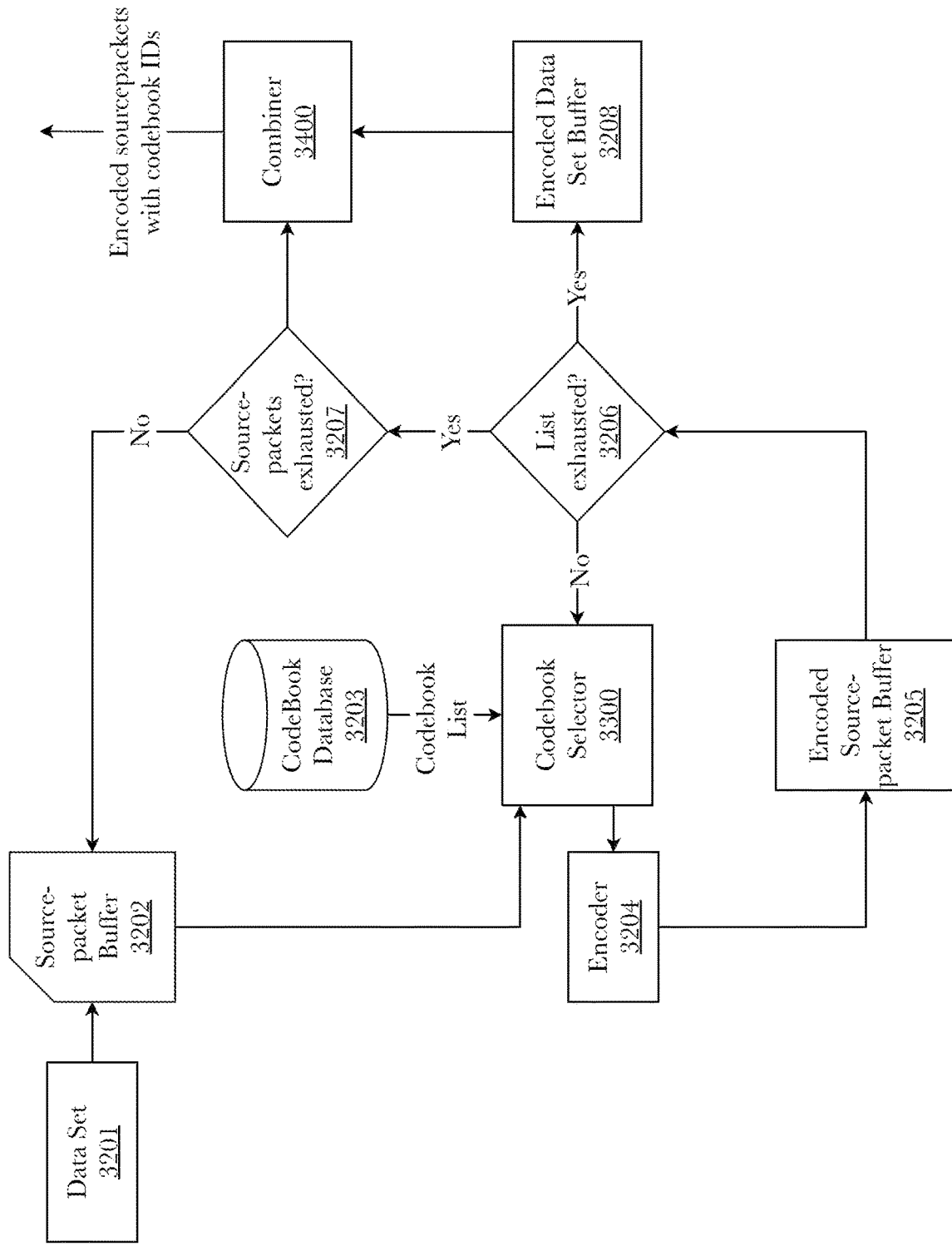
FIG. 32 is an exemplary system architecture for an encoding system with multiple codebooks.

FIG. 32 is an exemplary system architecture for an encoding system with multiple codebooks. A data set to be encoded 3201 is sent to a sourcepacket buffer 3202. The sourcepacket buffer is an array which stores the data which is to be encoded and may contain a plurality of sourcepackets. Each sourcepacket is routed to a codebook selector 3300, which retrieves a list of codebooks from a codebook database 3203. The sourcepacket is encoded using the first codebook on the list via an encoder 3204, and the output is stored in an encoded sourcepacket buffer 3205. The process is repeated with the same sourcepacket using each subsequent codebook on the list until the list of codebooks is exhausted 3206, at which point the most compact encoded version of the sourcepacket is selected from the encoded sourcepacket buffer 3205 and sent to an encoded data set buffer 3208 along with the ID of the codebook used to produce it. The sourcepacket buffer 3202 is determined to be exhausted 3207, a notification is sent to a combiner 3400, which retrieves all of the encoded sourcepackets and codebook IDs from the encoded data set buffer 3208, and combines them into a single file for output.

According to an embodiment, the list of codebooks used in encoding the data set may be consolidated to a single codebook which is provided to the combiner 3400 for output along with the encoded sourcepackets and codebook IDs. In this case, the single codebook will contain the data from, and codebook IDs of, each of the codebooks used to encode the data set. This may provide a reduction in data transfer time, although it is not required since each sourcepacket (or sourceblock) will contain a reference to a specific codebook ID which references a codebook that can be pulled from a database or be sent alongside the encoded data to a receiving device for the decoding process.

In some embodiments, each sourcepacket of a data set 3201 arriving at the encoder 3204 is encoded using a different sourceblock length. Changing the sourceblock length changes the encoding output of a given codebook. Two sourcepackets encoded with the same codebook but using different sourceblock lengths would produce different encoded outputs. Therefore, changing the sourceblock length of some or all sourcepackets in a data set 3201 provides additional security. Even if the codebook was known, the sourceblock length would have to be known or derived for each sourceblock in order to decode the data set 3201. Changing the sourceblock length may be used in conjunction with the use of multiple codebooks.

Figure 33:
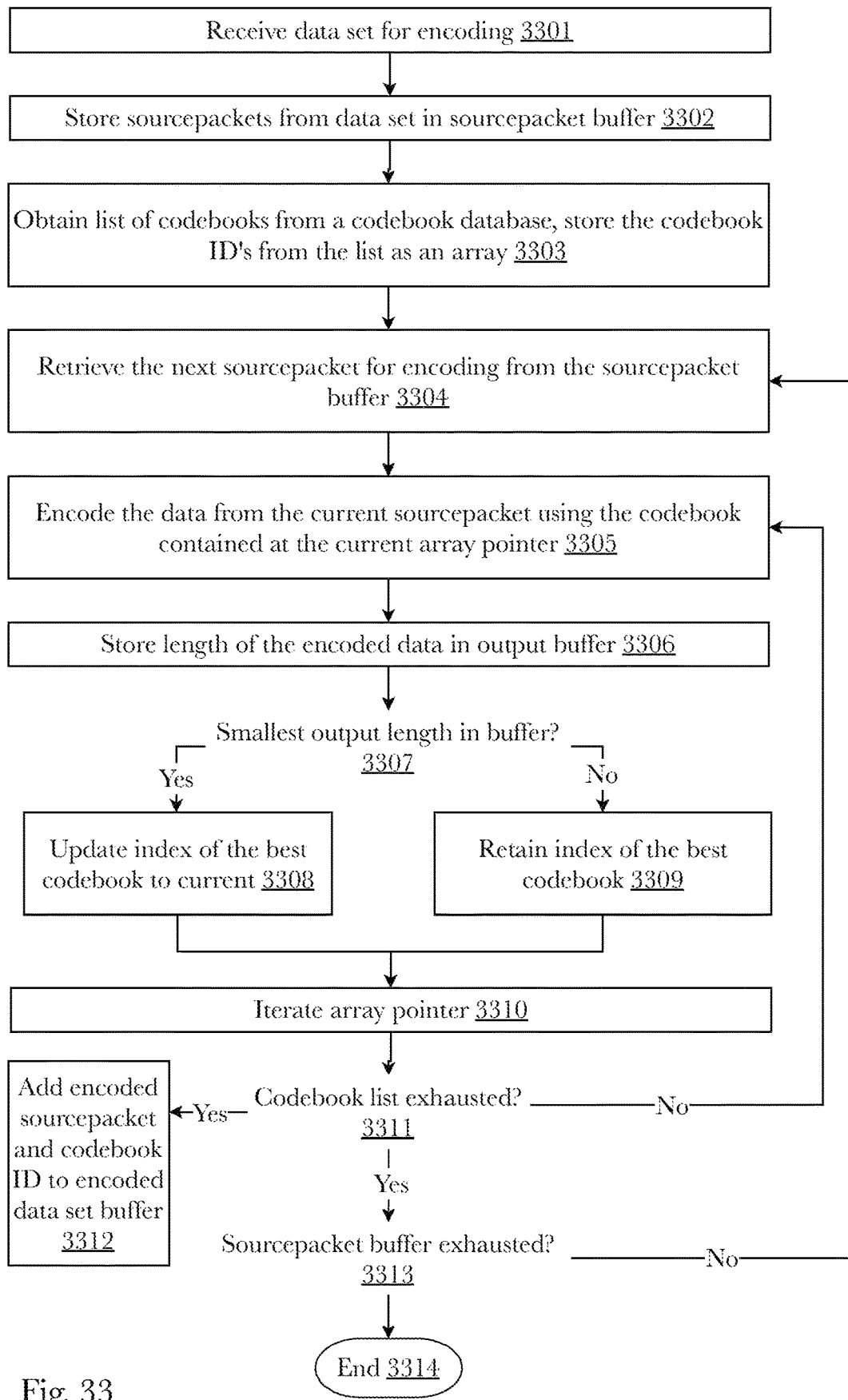
FIG. 33 is a flow diagram describing an exemplary algorithm for encoding of data using multiple codebooks.

FIG. 33 is a flow diagram describing an exemplary algorithm for encoding of data using multiple codebooks. A data set is received for encoding 3301, the data set comprising a plurality of sourcepackets. The sourcepackets are stored in a sourcepacket buffer 3302. A list of codebooks to be used for multiple codebook encoding is retrieved from a codebook database (which may contain more codebooks than are contained in the list) and the codebook IDs for each codebook on the list are stored as an array 3303. The next sourcepacket in the sourcepacket buffer is retrieved from the sourcepacket buffer for encoding 3304. The sourcepacket is encoded using the codebook in the array indicated by a current array pointer 3305. The encoded sourcepacket and length of the encoded sourcepacket is stored in an encoded sourcepacket buffer 3306. If the length of the most recently stored sourcepacket is the shortest in the buffer 3307, an index in the buffer is updated to indicate that the codebook indicated by the current array pointer is the most efficient codebook in the buffer for that sourcepacket. If the length of the most recently stored sourcepacket is not the shortest in the buffer 3307, the index in the buffer is not updated 3308 because a previous codebook used to encode that sourcepacket was more efficient 3309. The current array pointer is iterated to select the next codebook in the list 3310. If the list of codebooks has not been exhausted 3311, the process is repeated for the next codebook in the list, starting at step 3305. If the list of codebooks has been exhausted 3311, the encoded sourcepacket in the encoded sourcepacket buffer (the most compact version) and the codebook ID for the codebook that encoded it are added to an encoded data set buffer 3312 for later combination with other encoded sourcepackets from the same data set. At that point, the sourcepacket buffer is checked to see if any sourcepackets remain to be encoded 3313. If the sourcepacket buffer is not exhausted, the next sourcepacket is retrieved 3304 and the process is repeated starting at step 3304. If the sourcepacket buffer is exhausted 3313, the encoding process ends 3314. In some embodiments, rather than storing the encoded sourcepacket itself in the encoded sourcepacket buffer, a universal unique identification (UUID) is assigned to each encoded sourcepacket, and the UUID is stored in the encoded sourcepacket buffer instead of the entire encoded sourcepacket.

Figure 34:
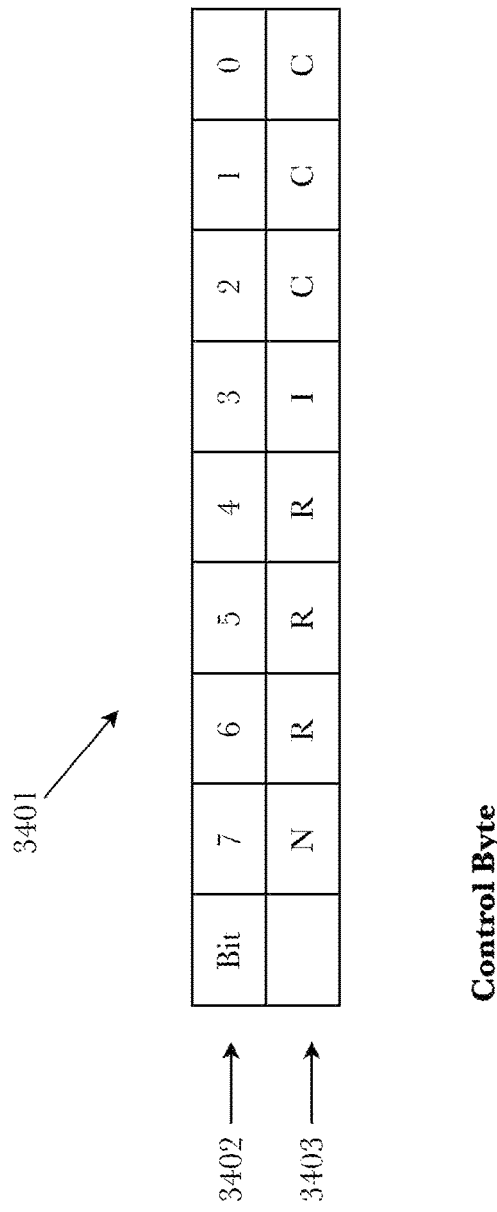
FIG. 34 is a flow diagram describing an exemplary codebook sorting algorithm for determining a plurality of codebooks to be shuffled between during the encoding process.

FIG. 34 is a diagram showing an exemplary control byte used to combine sourcepackets encoded with multiple codebooks. In this embodiment, a control byte 3401 (i.e., a series of 8 bits) is inserted at the before (or after, depending on the configuration) the encoded sourcepacket with which it is associated, and provides information about the codebook that was used to encode the sourcepacket. In this way, sourcepackets of a data set encoded using multiple codebooks can be combined into a data structure comprising the encoded sourcepackets, each with a control byte that tells the system how the sourcepacket can be decoded. The data structure may be of numerous forms, but in an embodiment, the data structure comprises a continuous series of control bytes followed by the sourcepacket associated with the control byte. In some embodiments, the data structure will comprise a continuous series of control bytes followed by the UUID of the sourcepacket associated with the control byte (and not the encoded sourcepacket, itself). In some embodiments, the data structure may further comprise a UUID inserted to identify the codebook used to encode the sourcepacket, rather than identifying the codebook in the control byte. Note that, while a very short control code (one byte) is used in this example, the control code may be of any length, and may be considerably longer than one byte in cases where the sourceblocks size is large or in cases where a large number of codebooks have been used to encode the sourcepacket or data set.

In this embodiment, for each bit location 3402 of the control byte 3401, a data bit or combinations of data bits 3403 provide information necessary for decoding of the sourcepacket associated with the control byte. Reading in reverse order of bit locations, the first bit N (location 7) indicates whether the entire control byte is used or not. If a single codebook is used to encode all sourcepackets in the data set, N is set to 0, and bits 3 to 0 of the control byte 3401 are ignored. However, where multiple codebooks are used, N is set to 1 and all 8 bits of the control byte 3401 are used. The next three bits RRR (locations 6 to 4) are a residual count of the number of bits that were not used in the last byte of the sourcepacket. Unused bits in the last byte of a sourcepacket can occur depending on the sourceblock size used to encode the sourcepacket. The next bit I (location 3) is used to identify the codebook used to encode the sourcepacket. If bit I is 0, the next three bits CCC (locations 2 to 0) provide the codebook ID used to encode the sourcepacket. The codebook ID may take the form of a codebook cache index, where the codebooks are stored in an enumerated cache. If bit I is 1, then the codebook is identified using a four-byte UUID that follows the control byte.

Figure 35:
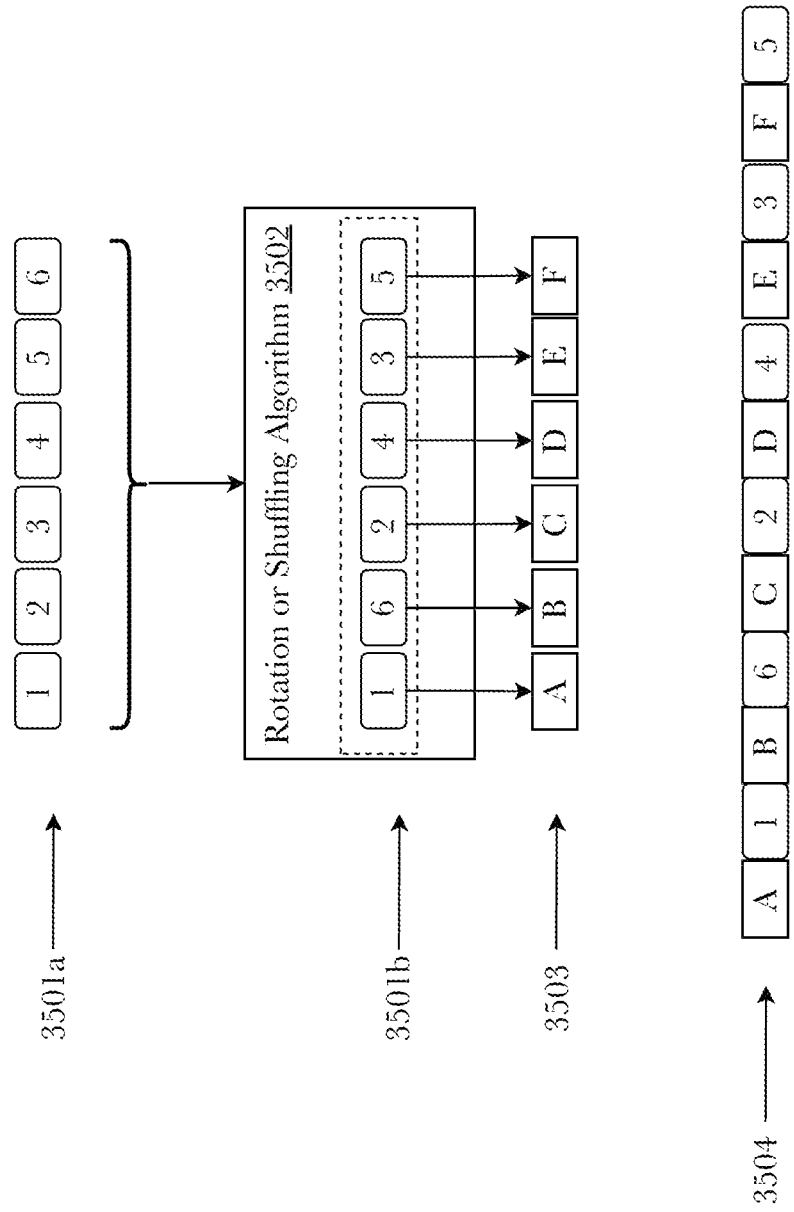
FIG. 35 is a diagram showing an exemplary codebook shuffling method.

FIG. 35 is a diagram showing an exemplary codebook shuffling method. In this embodiment, rather than selecting codebooks for encoding based on their compaction efficiency, codebooks are selected either based on a rotating list or based on a shuffling algorithm. The methodology of this embodiment provides additional security to compacted data, as the data cannot be decoded without knowing the precise sequence of codebooks used to encode any given sourcepacket or data set.

Here, a list of six codebooks is selected for shuffling, each identified by a number from 1 to 6 3501a. The list of codebooks is sent to a rotation or shuffling algorithm 3502, and reorganized according to the algorithm 3501b. The first six of a series of sourcepackets, each identified by a letter from A to E, 3503 is each encoded by one of the algorithms, in this case A is encoded by codebook 1, B is encoded by codebook 6, C is encoded by codebook 2, D is encoded by codebook 4, E is encoded by codebook 13 A is encoded by codebook 5. The encoded sourcepackets 3503 and their associated codebook identifiers 3501b are combined into a data structure 3504 in which each encoded sourcepacket is followed by the identifier of the codebook used to encode that particular sourcepacket.

According to an embodiment, the codebook rotation or shuffling algorithm 3502 may produce a random or pseudorandom selection of codebooks based on a function. Some non-limiting functions that may be used for shuffling include:
1. given a function f(n) which returns a codebook according to an input parameter n in the range 1 to N are, and given t the number of the current sourcepacket or sourceblock: f(t*M modulo p), where M is an arbitrary multiplying factor (1<=M<=p−1) which acts as a key, and p is a large prime number less than or equal to N;
2. f(A^t modulo p), where A is a base relatively prime to p−1 which acts as a key, and p is a large prime number less than or equal to N;
3. f(floor(t*x) modulo N), and x is an irrational number chosen randomly to act as a key;
4. f(t XOR K) where the XOR is performed bit-wise on the binary representations of t and a key K with same number of bits in its representation of N. The function f(n) may return the nth codebook simply by referencing the nth element in a list of codebooks, or it could return the nth codebook given by a formula chosen by a user.

In one embodiment, prior to transmission, the endpoints (users or devices) of a transmission agree in advance about the rotation list or shuffling function to be used, along with any necessary input parameters such as a list order, function code, cryptographic key, or other indicator, depending on the requirements of the type of list or function being used. Once the rotation list or shuffling function is agreed, the endpoints can encode and decode transmissions from one another using the encodings set forth in the current codebook in the rotation or shuffle plus any necessary input parameters.

In some embodiments, the shuffling function may be restricted to permutations within a set of codewords of a given length.

Note that the rotation or shuffling algorithm is not limited to cycling through codebooks in a defined order. In some embodiments, the order may change in each round of encoding. In some embodiments, there may be no restrictions on repetition of the use of codebooks.

In some embodiments, codebooks may be chosen based on some combination of compaction performance and rotation or shuffling. For example, codebook shuffling may be repeatedly applied to each sourcepacket until a codebook is found that meets a minimum level of compaction for that sourcepacket. Thus, codebooks are chosen randomly or pseudo-randomly for each sourcepacket, but only those that produce encodings of the sourcepacket better than a threshold will be used.

Figure 36:
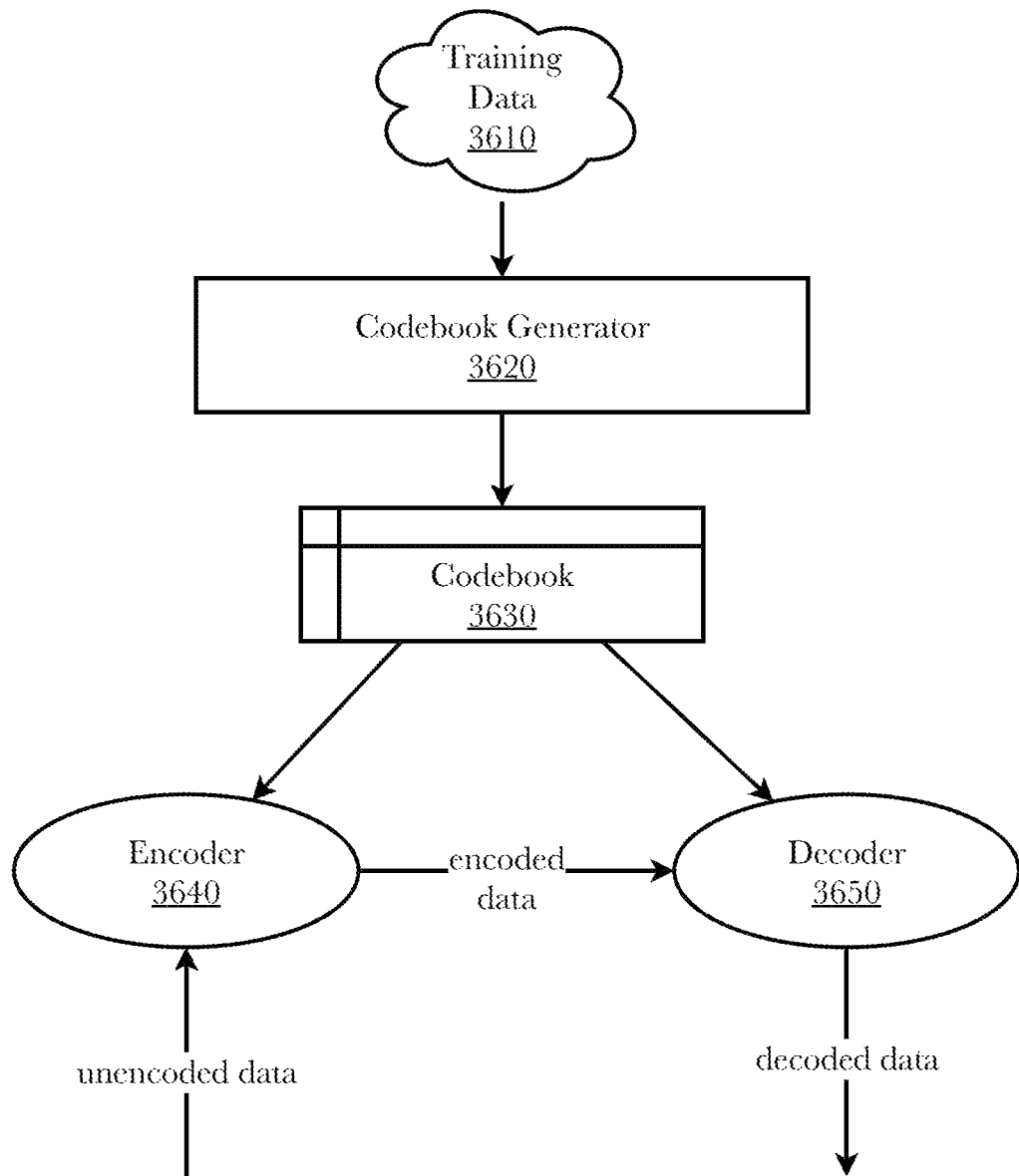
FIG. 36 shows an exemplary encoding/decoding configuration as previously described in an embodiment.

FIG. 36 shows an encoding/decoding configuration as previously described in an embodiment. In certain previously-described embodiments, training data 3610 is fed to a codebook generator 3620, which generates a codebook based on the training data. The codebook 3630 is sent to both an encoder 3640 and a decoder 3650 which may be on the same computer or on different computers, depending on the configuration. The encoder 3640 receives unencoded data, encodes it into codewords using the codebook 3630, and sends encoded data in the form of codewords to the decoder 3650. The decoder 3650 receives the encoded data in the form of codewords, decodes it using the same codebook 3630 (which may be a different copy of the codebook in some configurations), and outputs decoded data which is identical to the unencoded data received by the encoder 3640.

Figure 37:
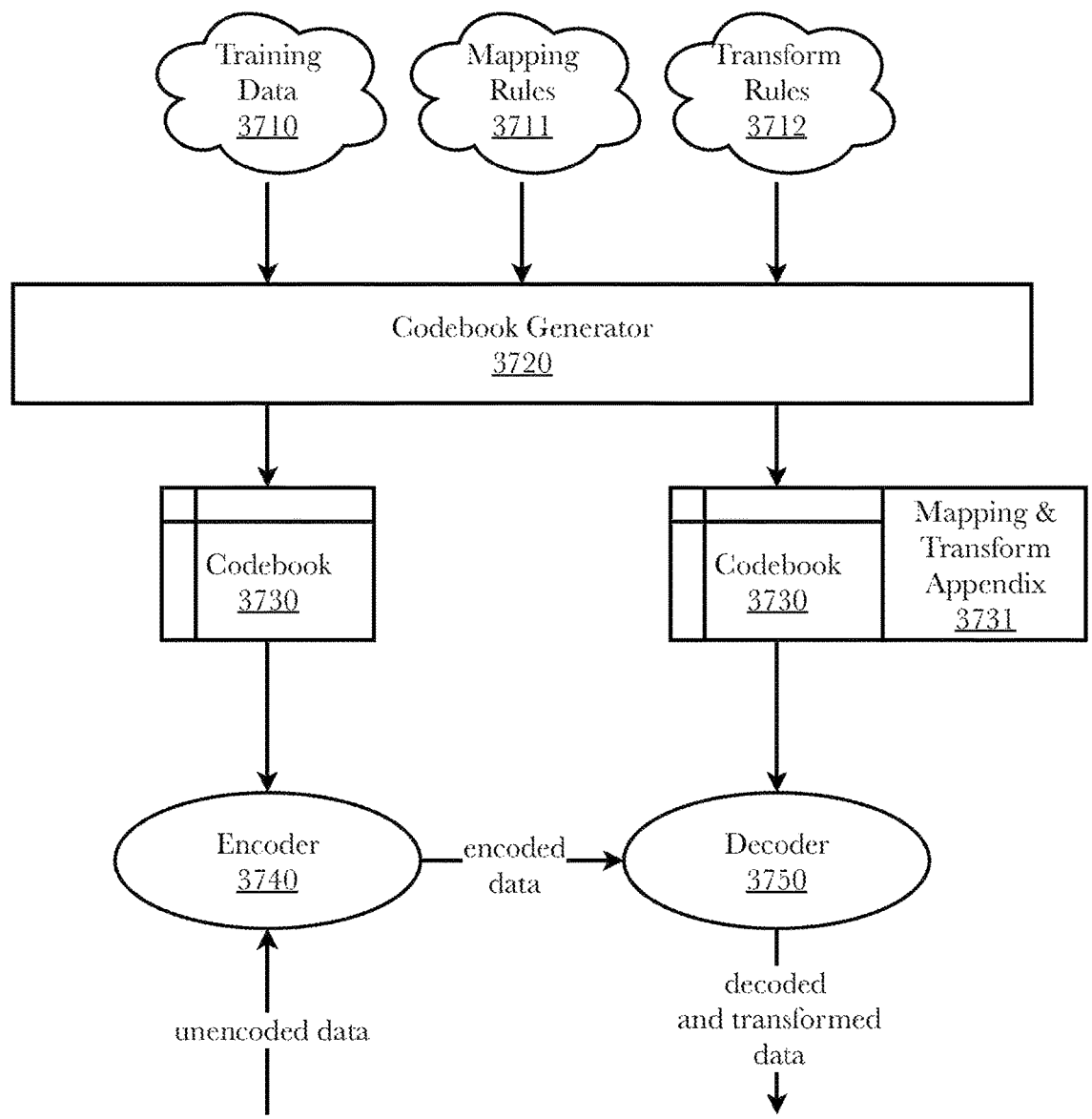
FIG. 37 shows an exemplary encoding/decoding configuration with extended functionality suitable to derive a different data set at the decoder from the data arriving at the encoder.

FIG. 37 shows an encoding/decoding configuration with extended functionality suitable to derive a different data set at the decoder from the data arriving at the encoder. In this configuration, mapping rules 3711 and data transformation rules 3712 are combined with the training data 3710 fed into the codebook generator. The codebook generator 3720 creates a codebook 3730 from the training data. The codebook 3730 is sent to the encoder 3740 which receives unencoded data, encodes it into codewords using the codebook 3730, and sends encoded data in the form of codewords to the decoder 3750. In this configuration, however, the codebook generator 3720 also creates a mapping and transformation appendix 3731 which it appends to the copy of the codebook 3730 sent to the decoder. The appendix 3731 may be a separate file or document, or may be integrated into the codebook 3730, such as in the form of bit extensions appended to each sourceblock in the codebook 3730 or an additional dimensional array to the codebook 3730 which provides instructions as to mapping and transformations.

The decoder 3750 receives the encoded data in the form of codewords, decodes it using the same codebook 3730 (which may be a different copy of the codebook in some configurations), but instead of outputting decoded data which is identical to the unencoded data received by the encoder 3740, the decoder maps and/or transforms the decoded data according to the mapping and transformation appendix, converting the decoded data into a transformed data output. As a simple example of the operation of this configuration, the unencoded data received by the encoder 3740 might be a list of geographical location names, and the decoded and transformed data output by the decoder based on the mapping and transformation appendix 3731 might be a list of GPS coordinates for those geographical location names.

In some embodiments, artificial intelligence or machine learning algorithms might be used to develop or generate the mapping and transformation rules. For example, the training data might be processed through a machine learning algorithm trained (on a different set of training data) to identify certain characteristics within the training data such as unusual numbers of repetitions of certain bit patterns, unusual amounts of gaps in the data (e.g., large numbers of zeros), or even unusual amounts of randomness, each of which might indicate a problem with the data such as missing or corrupted data, possible malware, possible encryption, etc. As the training data is processed, the mapping and transform appendix 3731 is generated by the machine learning algorithm based on the identified characteristics. In this example, the output of the decoder might be indications of the locations of possible malware in the decoded data or portions of the decoded data that are encrypted. In some embodiments, direct encryption (e.g., SSL) might be used to further protect the encoded data during transmission.

Figure 38:
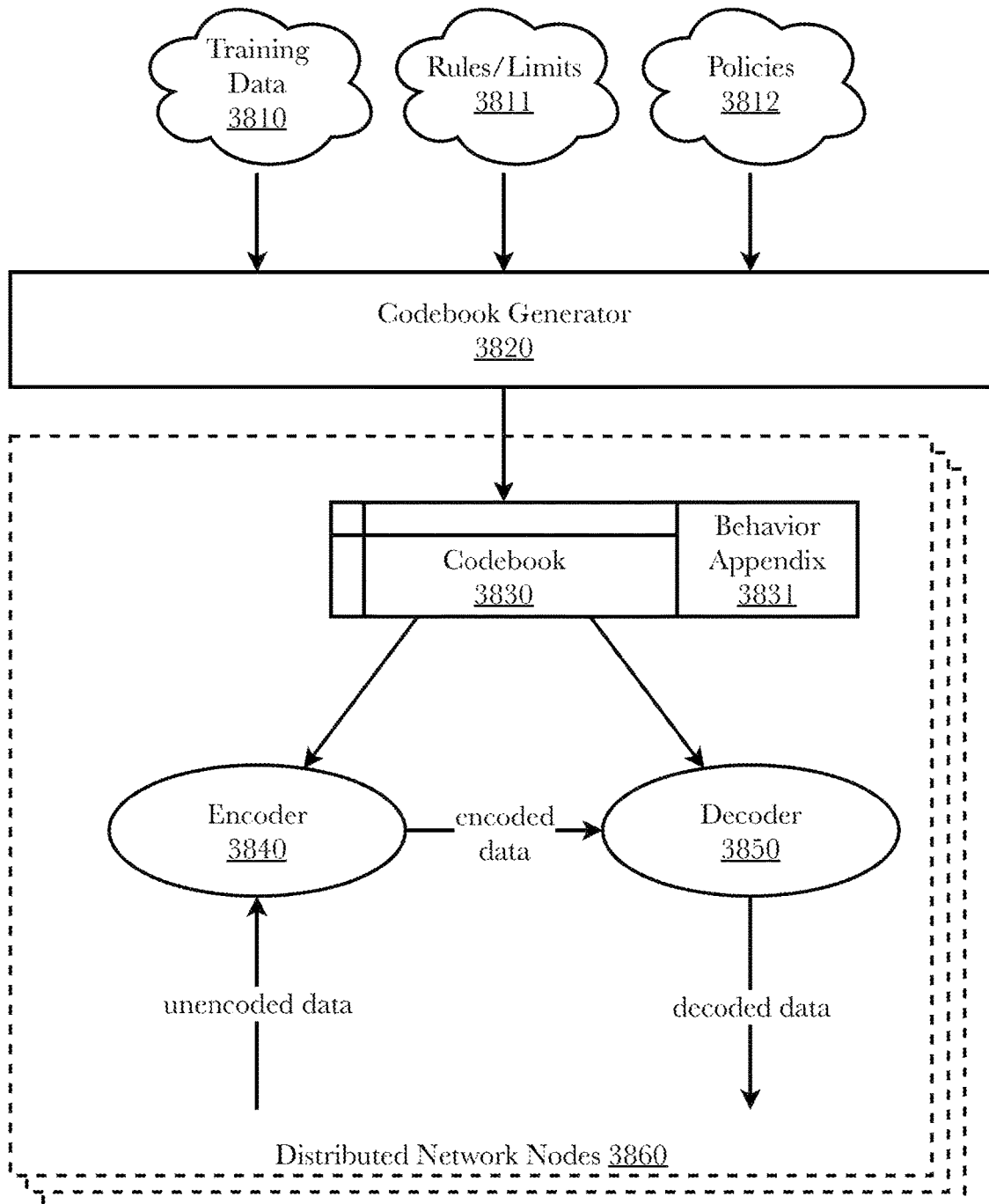
FIG. 38 shows an exemplary encoding/decoding configuration with extended functionality suitable for using in a distributed computing environment.

FIG. 38 shows an encoding/decoding configuration with extended functionality suitable for using in a distributed computing environment comprising a plurality of distributed network nodes 3860. In this configuration, network rules and limits 3811 and network policies 3812 are combined with the training data 3810 fed into the codebook generator. The codebook generator 3820 creates a codebook 3830 from the training data. The codebook generator 3820 also creates a behavior appendix 3831 which it appends to the copies of the codebook 3830 sent to both the encoder 3840 and decoder 3850. The appendix 3831 may be a separate file or document, or may be integrated into the codebook 3830, such as in the form of bit extensions appended to each sourceblock in the codebook 3830 which provide instructions as to mapping and transformations. In some embodiments, the behavior appendix 3831 may be sent only to the encoder 3840 or decoder 3850, depending on network configuration and other parameters.

The encoder 3840 receives unencoded data, implements any behaviors required by the behavior appendix 3831 such as limit checking, network policies, data prioritization, permissions, etc., as encodes it into codewords using the codebook 3830. For example, as data is encoded, the encoder may check the behavior appendix for each sourceblock within the data to determine whether that sourceblock (or a combination of sourceblocks) violates any network rules. As a couple of non-limiting examples, certain sourceblocks may be identified, for example, as fingerprints for malware or viruses, and may be blocked from further encoding or transmission, or certain sourceblocks or combinations of sourceblocks may be restricted to encoding on some nodes of the network, but not others. The decoder works in a similar manner. The decoder 3850 receives encoded data, implements any behaviors required by the behavior appendix 3831 such as limit checking, network policies, data prioritization, permissions, etc., as decodes it into decoded data using the codebook 3830 resulting in data identical to the unencoded data received by the encoder 3840. For example, as data is decoded, the decoder may check the behavior appendix for each sourceblock within the data to determine whether that sourceblock (or a combination of sourceblocks) violates any network rules. As a couple of non-limiting examples, certain sourceblocks may be identified, for example, as fingerprints for malware or viruses, and may be blocked from further decoding or transmission, or certain sourceblocks or combinations of sourceblocks may be restricted to decoding on some nodes of the network, but not others.

In some embodiments, artificial intelligence or machine learning algorithms might be used to develop or generate the behavioral appendix 3831. For example, the training data might be processed through a machine learning algorithm trained (on a different set of training data) to identify certain characteristics within the training data such as unusual numbers of repetitions of certain bit patterns, unusual amounts of gaps in the data (e.g., large numbers of zeros), or even unusual amounts of randomness, each of which might indicate a problem with the data such as missing or corrupted data, possible malware, possible encryption, etc. As the training data is processed, the mapping and transform appendix 3831 is generated by the machine learning algorithm based on the identified characteristics. As a couple of non-limiting examples, the machine learning algorithm might generate a behavior appendix 3831 in which certain sourceblocks are identified, for example, as fingerprints for malware or viruses, and are blocked from further decoding or transmission, or in which certain sourceblocks or combinations of sourceblocks are restricted to decoding on some nodes of the network, but not others.

Figure 39:
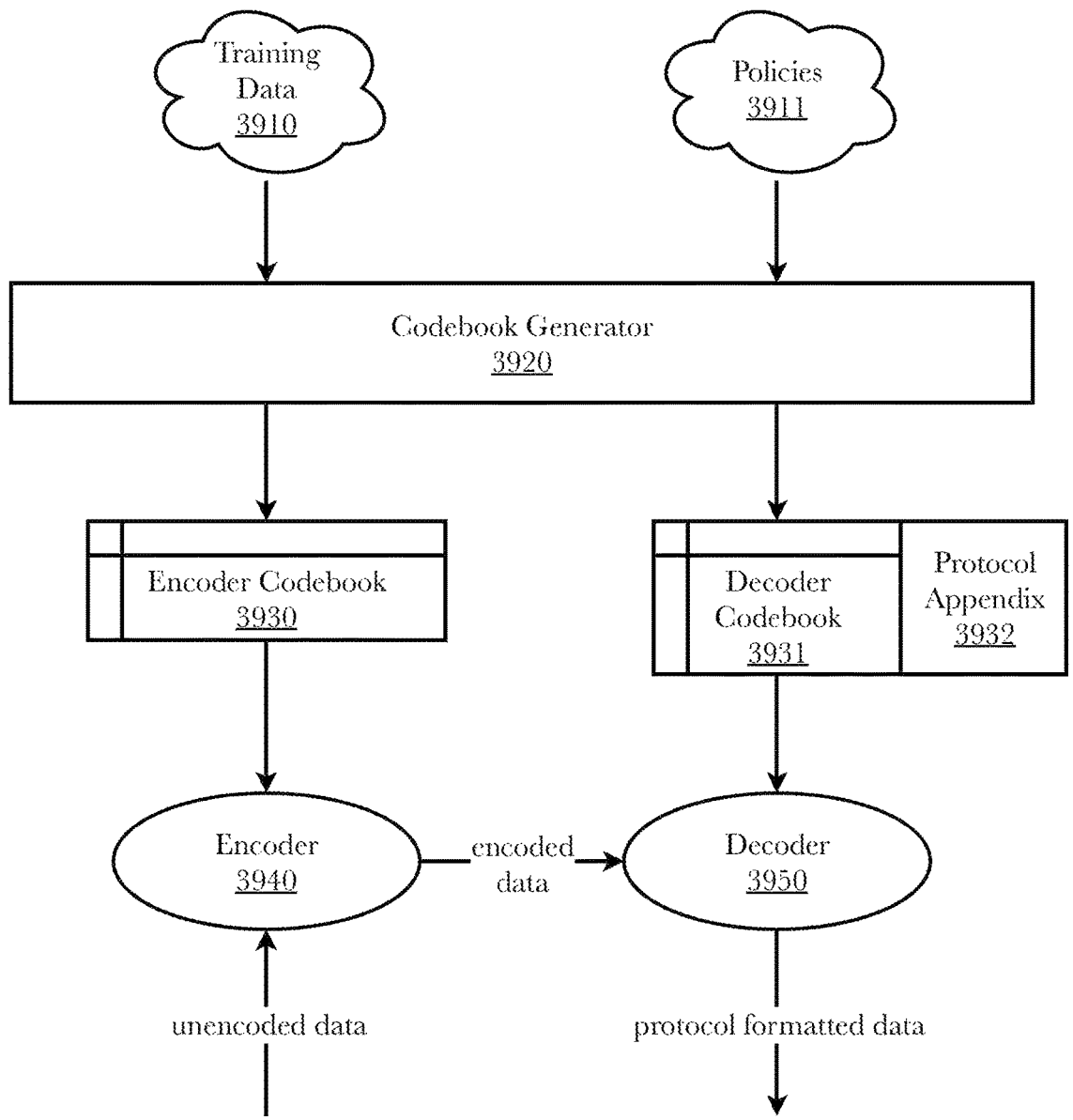
FIG. 39 shows an exemplary encoding/decoding configuration with extended functionality suitable for generating protocol formatted data at the decoder derived from data arriving at the encoder.

FIG. 39 shows an encoding/decoding configuration with extended functionality suitable for generating protocol formatted data at the decoder derived from data arriving at the encoder. In this configuration, protocol formatting policies 3911 are combined with the training data 3910 fed into the codebook generator. The codebook generator 3920 creates a codebook 3930 from the training data. The codebook 3930 is sent to the encoder 3940 which receives unencoded data, encodes it into codewords using the codebook 3930, and sends encoded data in the form of codewords to the decoder 3950. In this configuration, however, the codebook generator 3920 also creates a protocol appendix 3931 which it appends to the copy of the codebook 3930 sent to the decoder. The appendix 3931 may be a separate file or document, or may be integrated into the codebook 3930, such as in the form of bit extensions appended to each sourceblock in the codebook 3930 or an additional dimensional array to the codebook 3930 which provides instructions as to protocol formatting.

The decoder 3950 receives the encoded data in the form of codewords, decodes it using the same codebook 3930 (which may be a different copy of the codebook in some configurations), and but instead of outputting decoded data which is identical to the unencoded data received by the encoder 3940, the decoder converts the decoded data according to the protocol appendix, converting the decoded data into a protocol formatted data output. As a simple example of the operation of this configuration, the unencoded data received by the encoder 3940 might be a data to be transferred over a TCP/IP connection, and the decoded and transformed data output by the decoder based on the protocol appendix 3931 might be the data formatted according to the TCP/IP protocol.

In some embodiments, artificial intelligence or machine learning algorithms might be used to develop or generate the protocol policies. For example, the training data might be processed through a machine learning algorithm trained (on a different set of training data) to identify certain characteristics within the training data such as types of files or portions of data that are typically sent to a particular port on a particular node of a network, etc. As the training data is processed, the protocol appendix 3931 is generated by the machine learning algorithm based on the identified characteristics. In this example, the output of the decoder might be the unencoded data formatted according to the TCP/IP protocol in which the TCP/IP destination is changed based on the contents of the data or portions of the data (e.g., portions of data of one type are sent to one port on a node and portions of data of a different type are sent to a different port on the same node). In some embodiments, direct encryption (e.g., SSL) might be used to further protect the encoded data during transmission.

Figure 40:
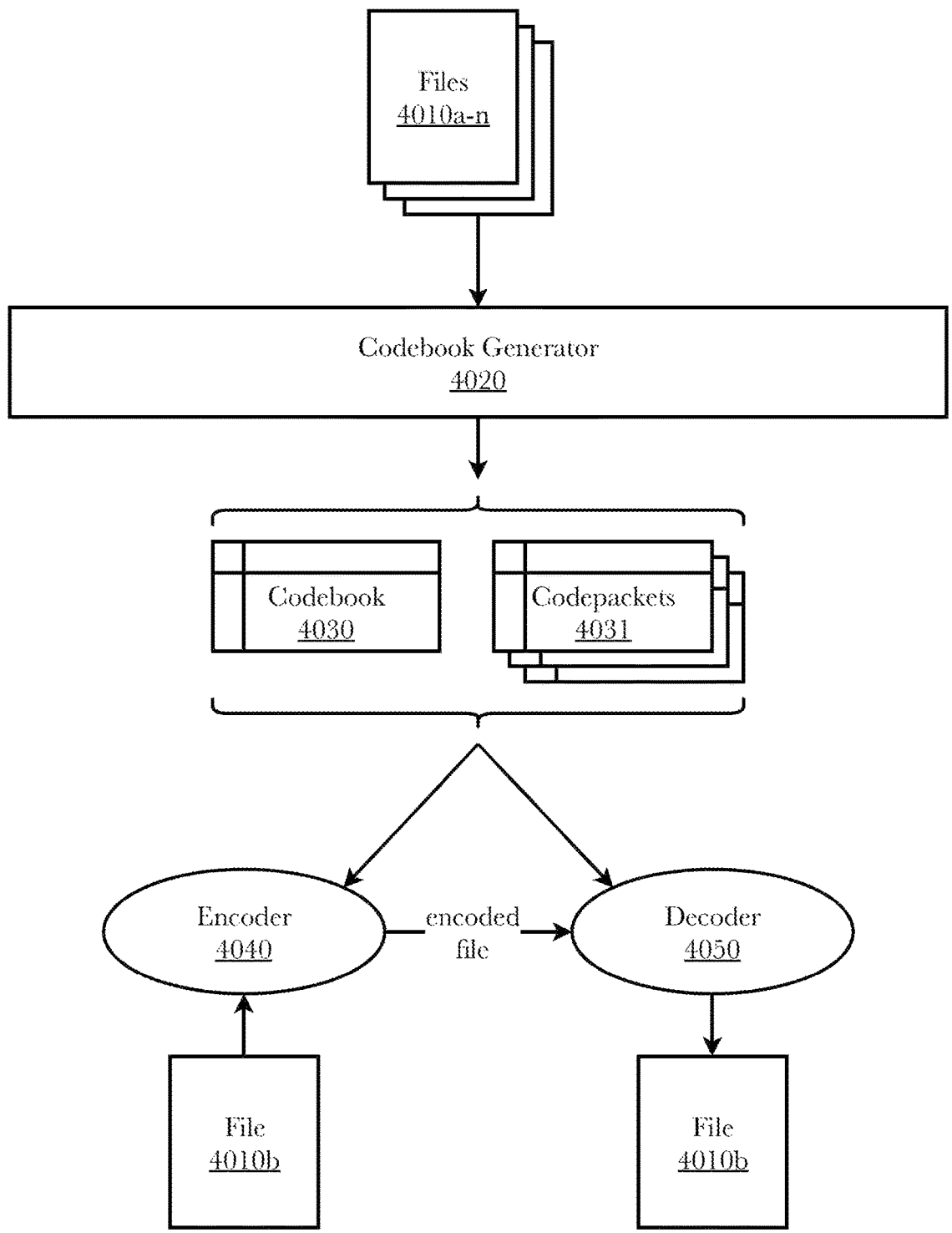
FIG. 40 shows an exemplary encoding/decoding configuration with extended functionality suitable for file-based encoding/decoding.

FIG. 40 shows an exemplary encoding/decoding configuration with extended functionality suitable for file-based encoding/decoding. In this configuration, training data in the form of a set of files 4010 is fed to a codebook generator 4020, which generates a codebook based on the files 4010. The codebook may comprise a single codebook 4030 generated from all of the files, or a set of smaller codebooks called codepackets 4031, each codepacket 4031 being generated from one of the files, or a combination of both. The codebook 4030 and/or codepackets 4031 are sent to both an encoder 4040 and a decoder 4050 which may be on the same computer or on different computers, depending on the configuration. The encoder 4040 receives a file, encodes it into codewords using the codebook 4030 or one of the codepackets 4031, and sends encoded file in the form of codewords to the decoder 4050. The decoder 4050 receives the encoded file in the form of codewords, decodes it using the same codebook 4030 (which may be a different copy of the codebook in some configurations), and outputs a decoded file which is identical to the unencoded data received by the encoder 4040. Any codebook miss (a codeword that can't be found either in the codebook 4030 or the relevant codepacket 4031) that occurs during decoding indicates that the file 4011 has been changed between encoding and decoding, thus providing the file-based encoding/decoding with inherent protection against changes.

Figure 41:
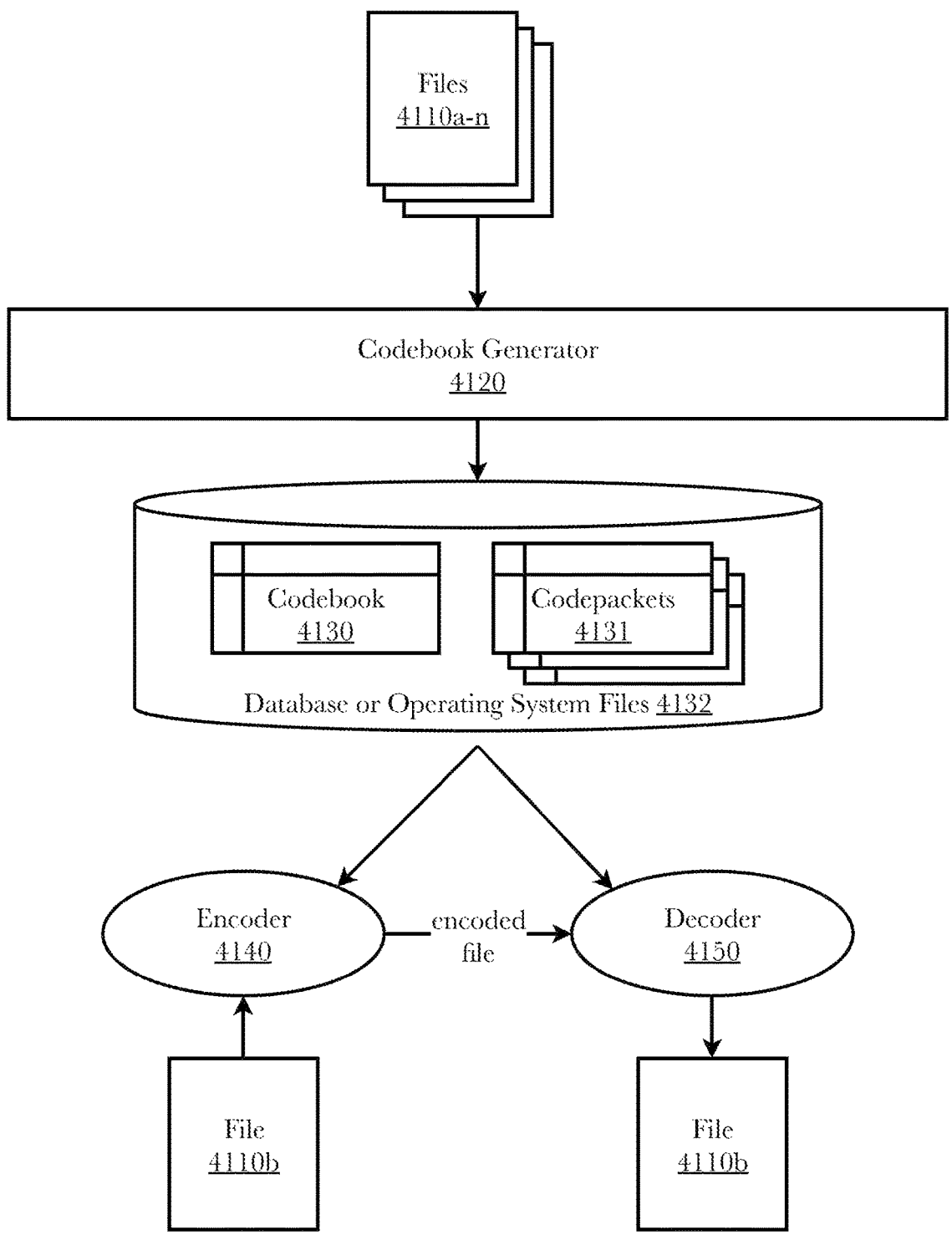
FIG. 41 shows an exemplary encoding/decoding configuration with extended functionality suitable for file-based encoding/decoding or operating system files.

FIG. 41 shows an exemplary encoding/decoding configuration with extended functionality suitable for file-based encoding/decoding or operating system files. File-based encoding/decoding of operating system files is a variant of the file-based encoding/decoding configuration described above. In file-based encoding/decoding of operating systems, one or more operating system files 4010a-n are used to create a codebook 4030 or a set of smaller files called codepackets 4031, each codepacket 4031 being created from a particular operating system file. Encoding and decoding of those same operating system files 4110a-n would be performed using the codebook 4130 or codepackets 4131 created from the operating system files 4110a-n. Consequently, encoding and decoding would be expected to produce no encoding misses (i.e., all possible sourceblocks of an operating system file to be encoded would be as sourceblocks in the codebook 4130 or the codepacket 4131 corresponding to the operating system file). A miss during encoding would indicate that the operating system file is either not one of those used to generate the codebook 4130 or has been changed. A miss during decoding (assuming that the operating system file encoded without a miss will be flagged as an indication the operating system file has been changed between encoding and decoding. Access to operating system files would be required to pass through the encoding/decoding process, thus protecting operating system files from tampering.

In this configuration, training data in the form of a set of operating system files 4110 is fed to a codebook generator 4120, which generates a codebook based on the operating system files 4110. The codebook may comprise a single codebook 4130 generated from all of the operating system files, or a set of smaller codebooks called codepackets 4131, each codepacket 4131 being generated from one of the operating system files, or a combination of both. The codebook 4130 and/or codepackets 4131 are sent to both an encoder 4141 and a decoder 4150 which may be on the same computer or on different computers, depending on the configuration. The encoder 4141 receives an operating system file 4110b from the set of operating system files 4110a-n used to generate the codebook 4130, encodes it into codewords using the codebook 4130 or one of the codepackets 4131, and sends encoded operating system file 4110b in the form of codewords to the decoder 4150. The decoder 4150 receives the encoded operating system file 4110b in the form of codewords, decodes it using the same codebook 4130 (which may be a different copy of the codebook in some configurations), and outputs a decoded operating system file 4110b which is identical to the unencoded operating system file 4110b received by the encoder 4141. Any codebook miss (a codeword that can't be found either in the codebook 4130 or the relevant codepacket 4131) that occurs during decoding indicates that the operating system file 4110b has been changed between encoding and decoding, thus providing the operating system file-based encoding/decoding with inherent protection against changes.

Figure 42:
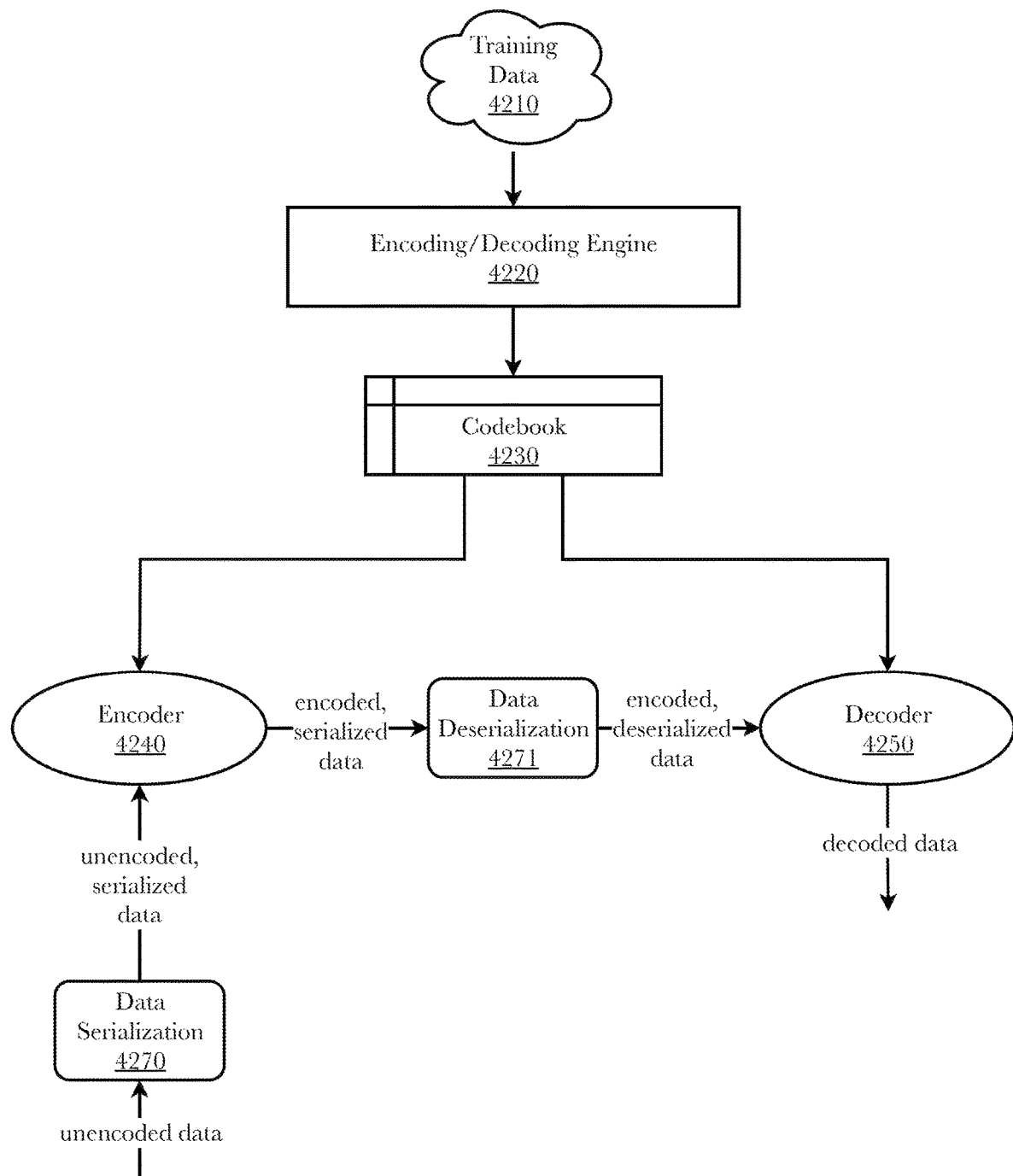
FIG. 42 shows an exemplary encoding/decoding configuration with data serialization and deserialization.

FIG. 42 shows an exemplary encoding/decoding configuration with data serialization and deserialization. In this embodiment, training data 4210 is fed to a codebook generator 4220, which generates a codebook based on the training data. The codebook 4230 is sent to both an encoder 4240 and a decoder 4250 which may be on the same computer or on different computers, depending on the configuration. Unencoded data is sent to a data serializer 4270, which serializes the data according to a serialization protocol (e.g., BeBop, Google Protocol Buffers, MessagePack) to create a wrapper or connector for the unencoded data. The encoder 4240 receives unencoded, serialized data, encodes it into codewords using the codebook 4230, and sends the encoded, serialized data to a destination, at which destination the data is received by a data deserializer 4271 which deserializes the data using the same serialization protocol as was used to serialize the data, and the encoded, deserialized data is then to a decoder 4250, which receives the encoded, unserialized data in the form of codewords, decodes it using the same codebook 4230 (which may be a different copy of the codebook in some configurations), and outputs decoded data which is identical to the unencoded data received by the encoder 4240.

The combination of data compaction with data serialization can be used to maximize compaction and data transfer with extremely low latency and no loss. For example, a wrapper or connector may be constructed using certain serialization protocols (e.g., BeBop, Google Protocol Buffers, MessagePack). The idea is to use known, deterministic file structure (schemes, grammars, etc.) to reduce data size first via token abbreviation and serialization, and then to use the data compaction methods described herein to take advantage of stochastic/statistical structure by training it on the output of serialization. The encoding process can be summarized as: serialization-encode→compact-encode, and the decoding process would be the reverse: compact-decode-→serialization-decode. The deterministic file structure could be automatically discovered or encoded by the user manually as a scheme/grammar. Another benefit of serialization in addition to those listed above is deeper obfuscation of data, further hardening the cryptographic benefits of encoding using codebooks.

Description of Method Aspects

Since the library consists of re-usable building sourceblocks, and the actual data is represented by reference codes to the library, the total storage space of a single set of data would be much smaller than conventional methods, wherein the data is stored in its entirety. The more data sets that are stored, the larger the library becomes, and the more data can be stored in reference code form.

As an analogy, imagine each data set as a collection of printed books that are only occasionally accessed. The amount of physical shelf space required to store many collections would be quite large, and is analogous to conventional methods of storing every single bit of data in every data set. Consider, however, storing all common elements within and across books in a single library, and storing the books as references codes to those common elements in that library. As a single book is added to the library, it will contain many repetitions of words and phrases. Instead of storing the whole words and phrases, they are added to a library, and given a reference code, and stored as reference codes. At this scale, some space savings may be achieved, but the reference codes will be on the order of the same size as the words themselves. As more books are added to the library, larger phrases, quotations, and other words patterns will become common among the books. The larger the word patterns, the smaller the reference codes will be in relation to them as not all possible word patterns will be used. As entire collections of books are added to the library, sentences, paragraphs, pages, or even whole books will become repetitive. There may be many duplicates of books within a collection and across multiple collections, many references and quotations from one book to another, and much common phraseology within books on particular subjects. If each unique page of a book is stored only once in a common library and given a reference code, then a book of 1,000 pages or more could be stored on a few printed pages as a string of codes referencing the proper full-sized pages in the common library. The physical space taken up by the books would be dramatically reduced. The more collections that are added, the greater the likelihood that phrases, paragraphs, pages, or entire books will already be in the library, and the more information in each collection of books can be stored in reference form. Accessing entire collections of books is then limited not by physical shelf space, but by the ability to reprint and recycle the books as needed for use.

The projected increase in storage capacity using the method herein described is primarily dependent on two factors: 1) the ratio of the number of bits in a block to the number of bits in the reference code, and 2) the amount of repetition in data being stored by the system.

With respect to the first factor, the number of bits used in the reference codes to the sourceblocks must be smaller than the number of bits in the sourceblocks themselves in order for any additional data storage capacity to be obtained. As a simple example, 16-bit sourceblocks would require 216, or 65536, unique reference codes to represent all possible patterns of bits. If all possible 65536 blocks patterns are utilized, then the reference code itself would also need to contain sixteen bits in order to refer to all possible 65,536 blocks patterns. In such case, there would be no storage savings. However, if only 16 of those block patterns are utilized, the reference code can be reduced to 4 bits in size, representing an effective compression of 4 times (16 bits/4 bits=4) versus conventional storage. Using a typical block size of 512 bytes, or 4,096 bits, the number of possible block patterns is 24,096, which for all practical purposes is unlimited. A typical hard drive contains one terabyte (TB) of physical storage capacity, which represents 1,953,125,000, or roughly 231, 512 byte blocks. Assuming that 1 TB of unique 512-byte sourceblocks were contained in the library, and that the reference code would thus need to be 31 bits long, the effective compression ratio for stored data would be on the order of 132 times (4,096/31≈132) that of conventional storage.

With respect to the second factor, in most cases it could be assumed that there would be sufficient repetition within a data set such that, when the data set is broken down into sourceblocks, its size within the library would be smaller than the original data. However, it is conceivable that the initial copy of a data set could require somewhat more storage space than the data stored in a conventional manner, if all or nearly all sourceblocks in that set were unique. For example, assuming that the reference codes are $1/10^{th}$ the size of a full-sized copy, the first copy stored as sourceblocks in the library would need to be 1.1 megabytes (MB), (1 MB for the complete set of full-sized sourceblocks in the library and 0.1 MB for the reference codes). However, since the sourceblocks stored in the library are universal, the more duplicate copies of something you save, the greater efficiency versus conventional storage methods. Conventionally, storing 10 copies of the same data requires 10 times the storage space of a single copy. For example, ten copies of a 1 MB file would take up 10 MB of storage space. However, using the method described herein, only a single full-sized copy is stored, and subsequent copies are stored as reference codes. Each additional copy takes up only a fraction of the space of the full-sized copy. For example, again assuming that the reference codes are $1/10^{th}$ the size of the full-size copy, ten copies of a 1 MB file would take up only 2 MB of space (1 MB for the full-sized copy, and 0.1 MB each for ten sets of reference codes). The larger the library, the more likely that part or all of incoming data will duplicate sourceblocks already existing in the library.

The size of the library could be reduced in a manner similar to storage of data. Where sourceblocks differ from each other only by a certain number of bits, instead of storing a new sourceblock that is very similar to one already existing in the library, the new sourceblock could be represented as a reference code to the existing sourceblock, plus information about which bits in the new block differ from the existing block. For example, in the case where 512 byte sourceblocks are being used, if the system receives a new sourceblock that differs by only one bit from a sourceblock already existing in the library, instead of storing a new 512 byte sourceblock, the new sourceblock could be stored as a reference code to the existing sourceblock, plus a reference to the bit that differs. Storing the new sourceblock as a reference code plus changes would require only a few bytes of physical storage space versus the 512 bytes that a full sourceblock would require. The algorithm could be optimized to store new sourceblocks in this reference code plus changes form unless the changes portion is large enough that it is more efficient to store a new, full sourceblock.

It will be understood by one skilled in the art that transfer and synchronization of data would be increased to the same extent as for storage. By transferring or synchronizing reference codes instead of full-sized data, the bandwidth requirements for both types of operations are dramatically reduced.

In addition, the method described herein is inherently a form of encryption. When the data is converted from its full form to reference codes, none of the original data is contained in the reference codes. Without access to the library of sourceblocks, it would be impossible to re-construct any portion of the data from the reference codes. This inherent property of the method described herein could obviate the need for traditional encryption algorithms, thereby offsetting most or all of the computational cost of conversion of data back and forth to reference codes. In theory, the method described herein should not utilize any additional computing power beyond traditional storage using encryption algorithms. Alternatively, the method described herein could be in addition to other encryption algorithms to increase data security even further.

In other embodiments, additional security features could be added, such as: creating a proprietary library of sourceblocks for proprietary networks, physical separation of the reference codes from the library of sourceblocks, storage of the library of sourceblocks on a removable device to enable easy physical separation of the library and reference codes from any network, and incorporation of proprietary sequences of how sourceblocks are read and the data reassembled.

Figure 7:
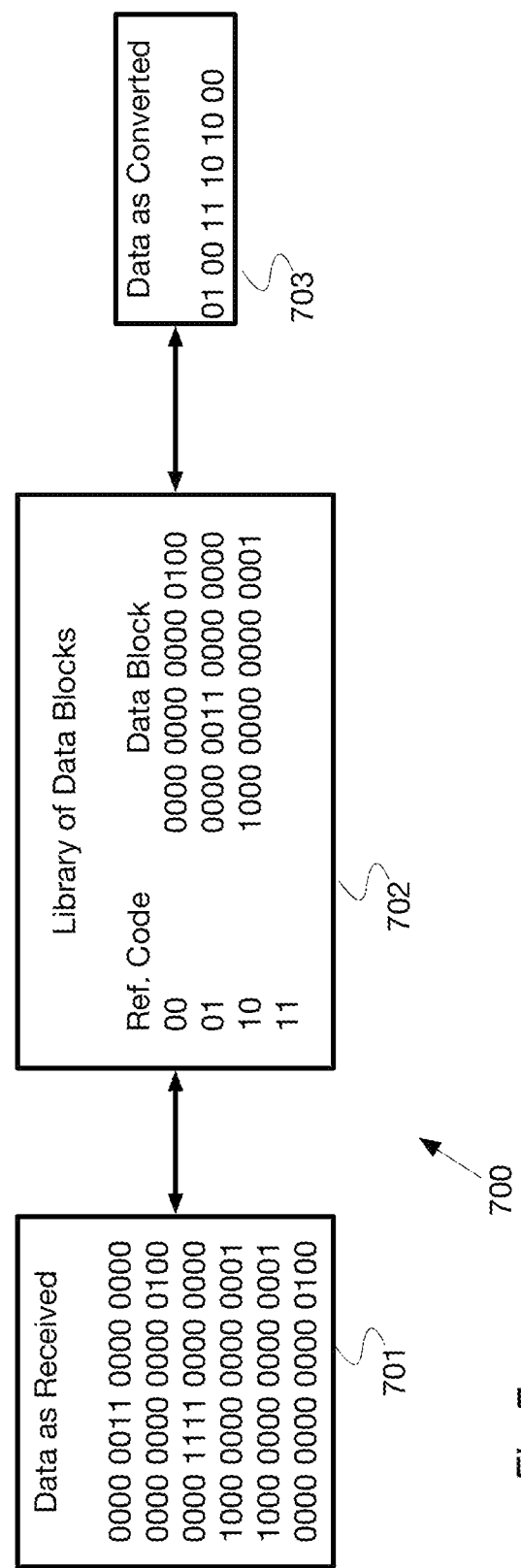
FIG. 7 is a diagram showing an example of how data might be converted into reference codes using an aspect of an embodiment.

FIG. 7 is a diagram showing an example of how data might be converted into reference codes using an aspect of an embodiment 700. As data is received 701, it is read by the processor in sourceblocks of a size dynamically determined by the previously disclosed sourceblock size optimizer 410. In this example, each sourceblock is 16 bits in length, and the library 702 initially contains three sourceblocks with reference codes 00, 01, and 10. The entry for reference code 11 is initially empty. As each 16 bit sourceblock is received, it is compared with the library. If that sourceblock is already contained in the library, it is assigned the corresponding reference code. So, for example, as the first line of data (0000 0011 0000 0000) is received, it is assigned the reference code (01) associated with that sourceblock in the library. If that sourceblock is not already contained in the library, as is the case with the third line of data (0000 1111 0000 0000) received in the example, that sourceblock is added to the library and assigned a reference code, in this case 11. The data is thus converted 703 to a series of reference codes to sourceblocks in the library. The data is stored as a collection of codewords, each of which contains the reference code to a sourceblock and information about the location of the sourceblocks in the data set. Reconstructing the data is performed by reversing the process. Each stored reference code in a data collection is compared with the reference codes in the library, the corresponding sourceblock is read from the library, and the data is reconstructed into its original form.

Figure 8:
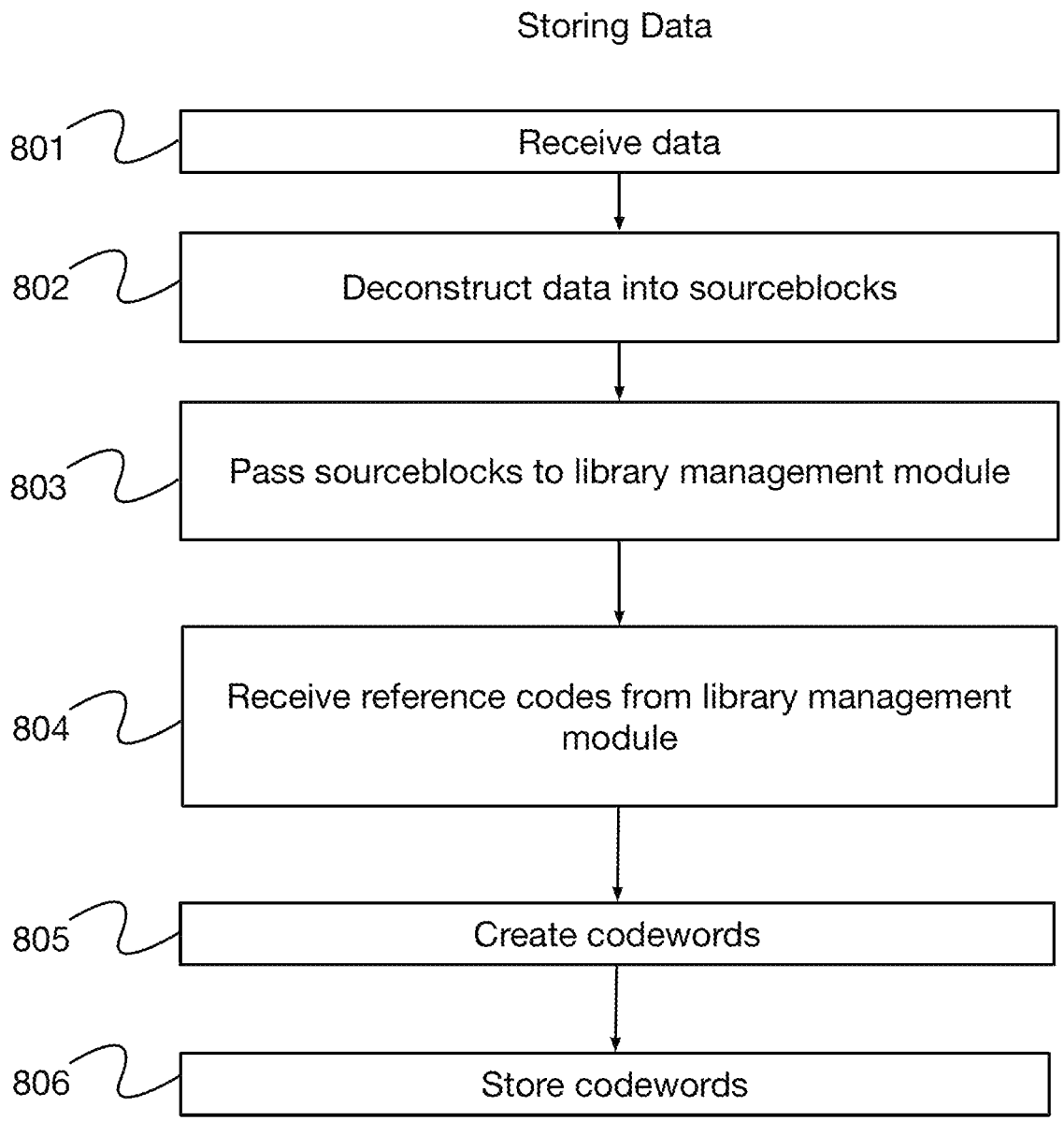
FIG. 8 is a method diagram showing the steps involved in using an embodiment to store data.

FIG. 8 is a method diagram showing the steps involved in using an embodiment 800 to store data. As data is received 801, it would be deconstructed into sourceblocks 802, and passed 803 to the library management module for processing. Reference codes would be received back 804 from the library management module, and could be combined with location information to create codewords 805, which would then be stored 806 as representations of the original data.

Figure 9:
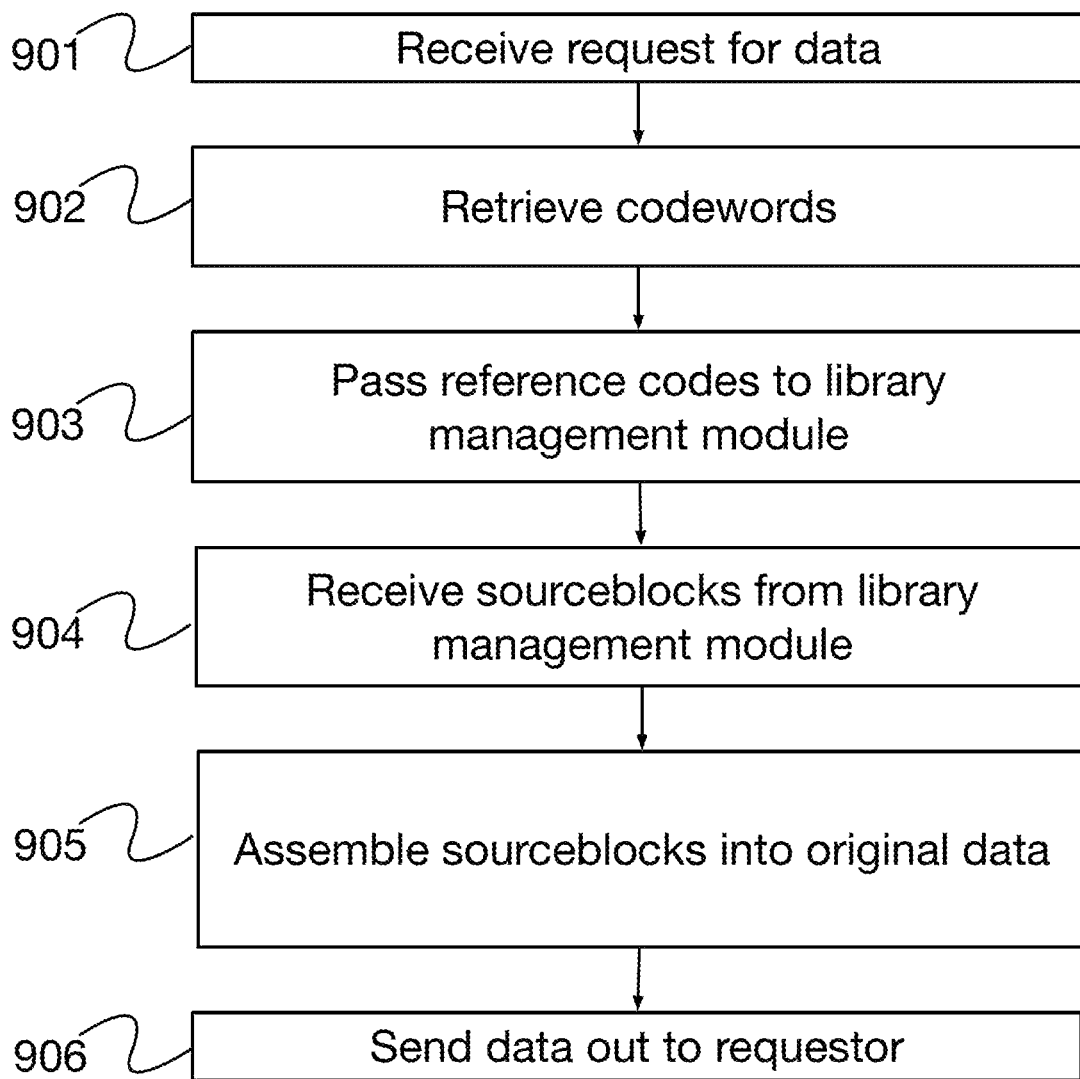
FIG. 9 is a method diagram showing the steps involved in using an embodiment to retrieve data.

FIG. 9 is a method diagram showing the steps involved in using an embodiment 900 to retrieve data. When a request for data is received 901, the associated codewords would be retrieved 902 from the library. The codewords would be passed 903 to the library management module, and the associated sourceblocks would be received back 904. Upon receipt, the sourceblocks would be assembled 905 into the original data using the location data contained in the codewords, and the reconstructed data would be sent out 906 to the requestor.

Figure 10:
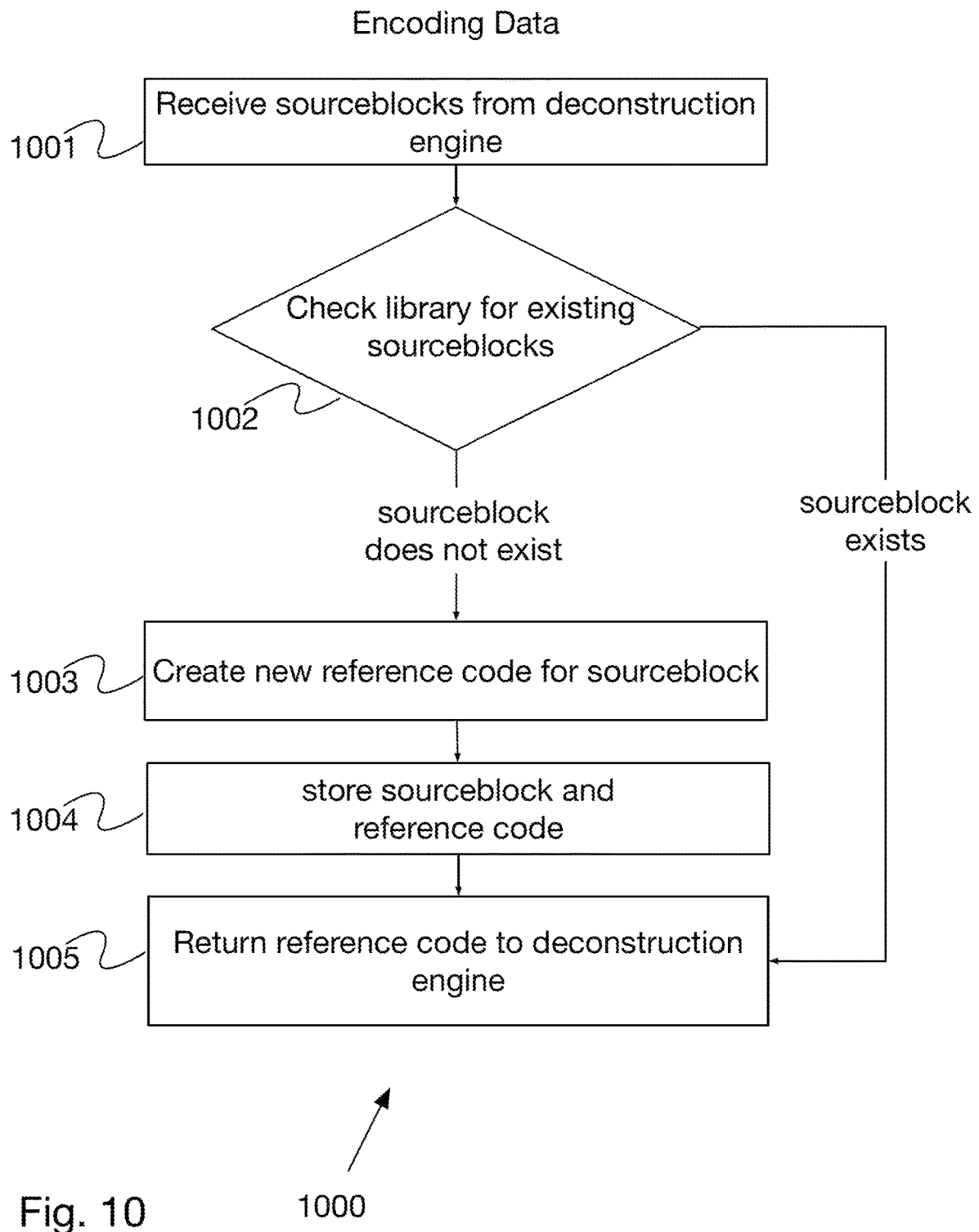
FIG. 10 is a method diagram showing the steps involved in using an embodiment to encode data.

FIG. 10 is a method diagram showing the steps involved in using an embodiment 1000 to encode data. As sourceblocks are received 1001 from the deconstruction engine, they would be compared 1002 with the sourceblocks already contained in the library. If that sourceblock already exists in the library, the associated reference code would be returned 1005 to the deconstruction engine. If the sourceblock does not already exist in the library, a new reference code would be created 1003 for the sourceblock. The new reference code and its associated sourceblock would be stored 1004 in the library, and the reference code would be returned to the deconstruction engine.

Figure 11:
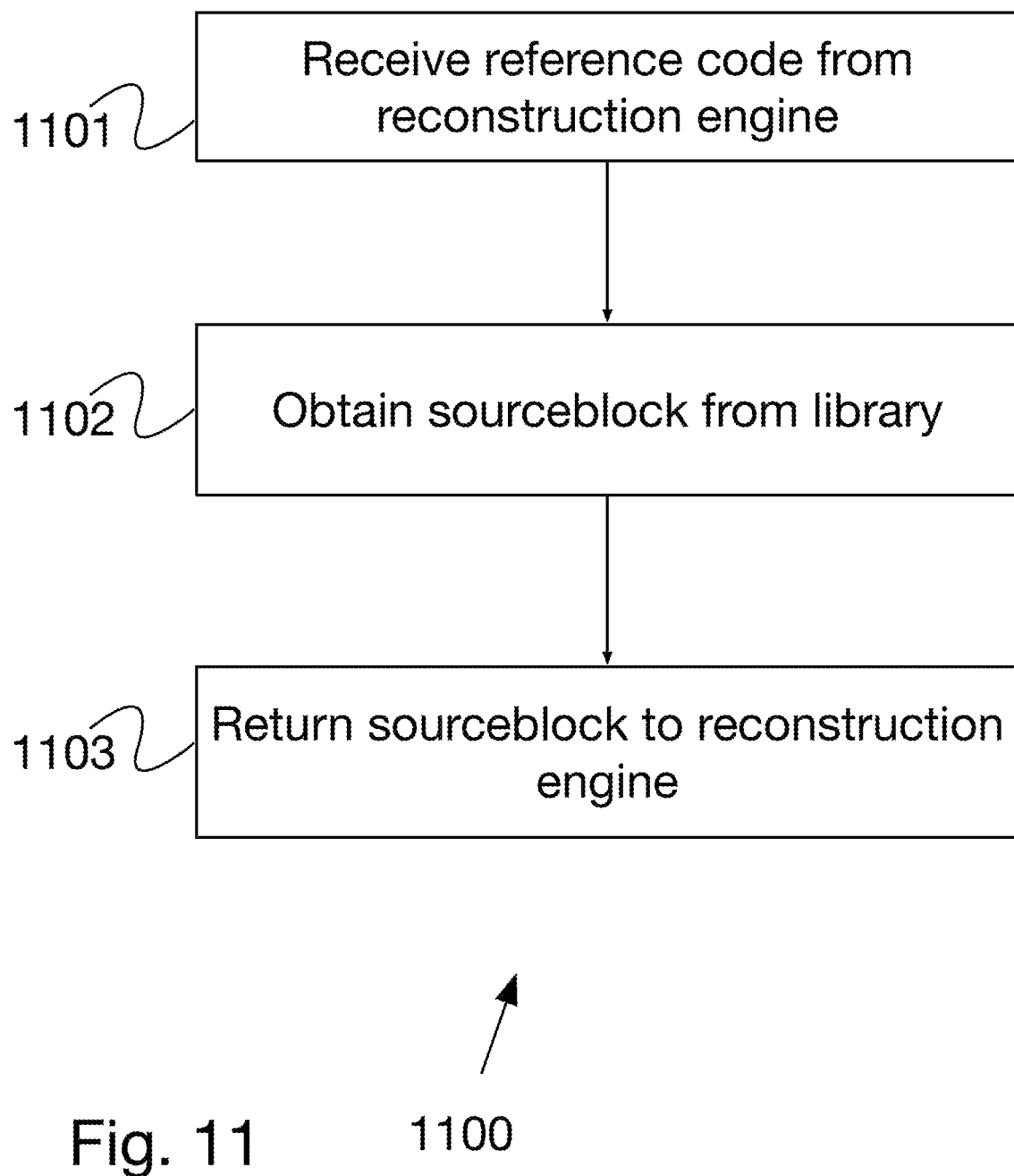
FIG. 11 is a method diagram showing the steps involved in using an embodiment to decode data.

FIG. 11 is a method diagram showing the steps involved in using an embodiment 1100 to decode data. As reference codes are received 1101 from the reconstruction engine, the associated sourceblocks are retrieved 1102 from the library, and returned 1103 to the reconstruction engine.

Figure 16:
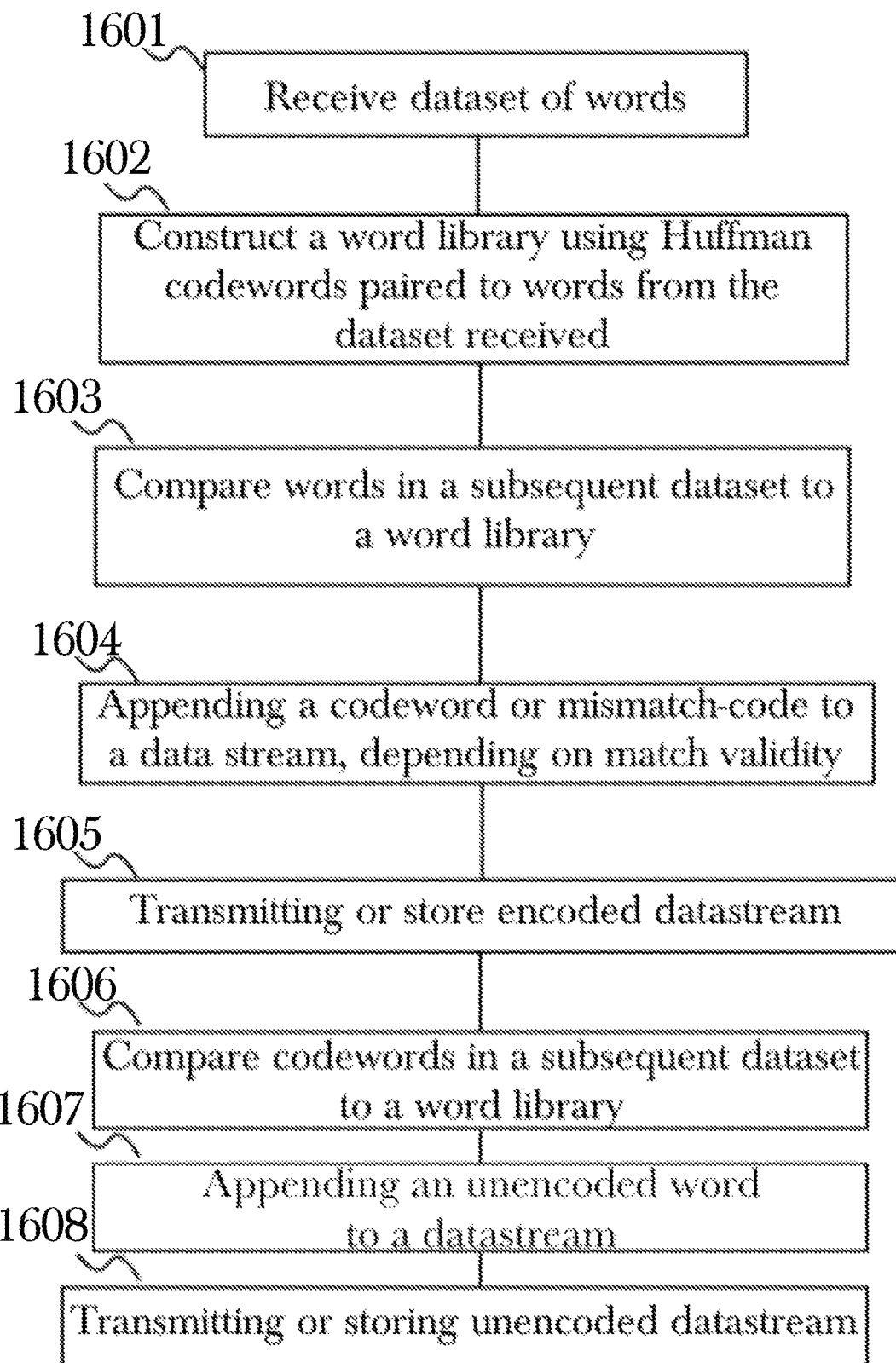
FIG. 16 is a method diagram illustrating key system functionality utilizing an encoder and decoder pair.

FIG. 16 is a method diagram illustrating key system functionality utilizing an encoder and decoder pair, according to a preferred embodiment. In a first step 1601, at least one incoming data set may be received at a customized library generator 1300 that then 1602 processes data to produce a customized word library 1201 comprising key-value pairs of data words (each comprising a string of bits) and their corresponding calculated binary Huffman codewords. A subsequent dataset may be received, and compared to the word library 1603 to determine the proper codewords to use in order to encode the dataset. Words in the dataset are checked against the word library and appropriate encodings are appended to a data stream 1604. If a word is mismatched within the word library and the dataset, meaning that it is present in the dataset but not the word library, then a mismatched code is appended, followed by the unencoded original word. If a word has a match within the word library, then the appropriate codeword in the word library is appended to the data stream. Such a data stream may then be stored or transmitted 1605 to a destination as desired. For the purposes of decoding, an already-encoded data stream may be received and compared 1606, and un-encoded words may be appended to a new data stream 1607 depending on word matches found between the encoded data stream and the word library that is present. A matching codeword that is found in a word library is replaced with the matching word and appended to a data stream, and a mismatch code found in a data stream is deleted and the following unencoded word is re-appended to a new data stream, the inverse of the process of encoding described earlier. Such a data stream may then be stored or transmitted 1608 as desired.

Figure 17:
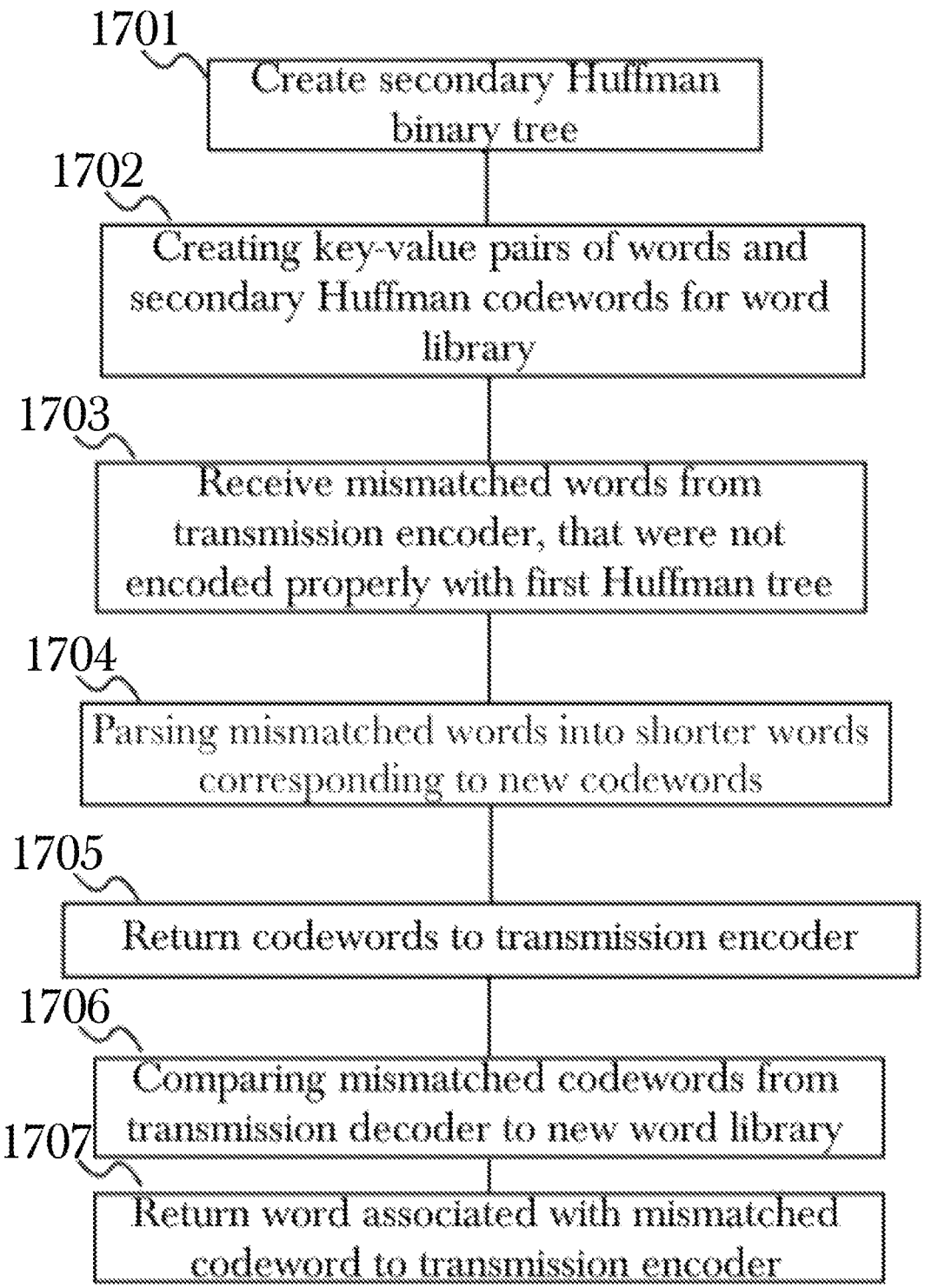
FIG. 17 is a method diagram illustrating possible use of a hybrid encoder/decoder to improve the compression ratio.

FIG. 17 is a method diagram illustrating possible use of a hybrid encoder/decoder to improve the compression ratio, according to a preferred aspect. A second Huffman binary tree may be created 1701, having a shorter maximum length of codewords than a first Huffman binary tree 1602, allowing a word library to be filled with every combination of codeword possible in this shorter Huffman binary tree 1702. A word library may be filled with these Huffman codewords and words from a dataset 1702, such that a hybrid encoder/decoder 1304, 1503 may receive any mismatched words from a dataset for which encoding has been attempted with a first Huffman binary tree 1703, 1604 and parse previously mismatched words into new partial codewords (that is, codewords that are each a substring of an original mismatched codeword) using the second Huffman binary tree 1704. In this way, an incomplete word library may be supplemented by a second word library. New codewords attained in this way may then be returned to a transmission encoder 1705, 1500. In the event that an encoded dataset is received for decoding, and there is a mismatch code indicating that additional coding is needed, a mismatch code may be removed and the unencoded word used to generate a new codeword as before 1706, so that a transmission encoder 1500 may have the word and newly generated codeword added to its word library 1707, to prevent further mismatching and errors in encoding and decoding.

It will be recognized by a person skilled in the art that the methods described herein can be applied to data in any form. For example, the method described herein could be used to store genetic data, which has four data units: C, G, A, and T. Those four data units can be represented as 2 bit sequences: 00, 01, 10, and 11, which can be processed and stored using the method described herein.

It will be recognized by a person skilled in the art that certain embodiments of the methods described herein may have uses other than data storage. For example, because the data is stored in reference code form, it cannot be reconstructed without the availability of the library of sourceblocks. This is effectively a form of encryption, which could be used for cyber security purposes. As another example, an embodiment of the method described herein could be used to store backup copies of data, provide for redundancy in the event of server failure, or provide additional security against cyberattacks by distributing multiple partial copies of the library among computers are various locations, ensuring that at least two copies of each sourceblock exist in different locations within the network.

Figure 18:
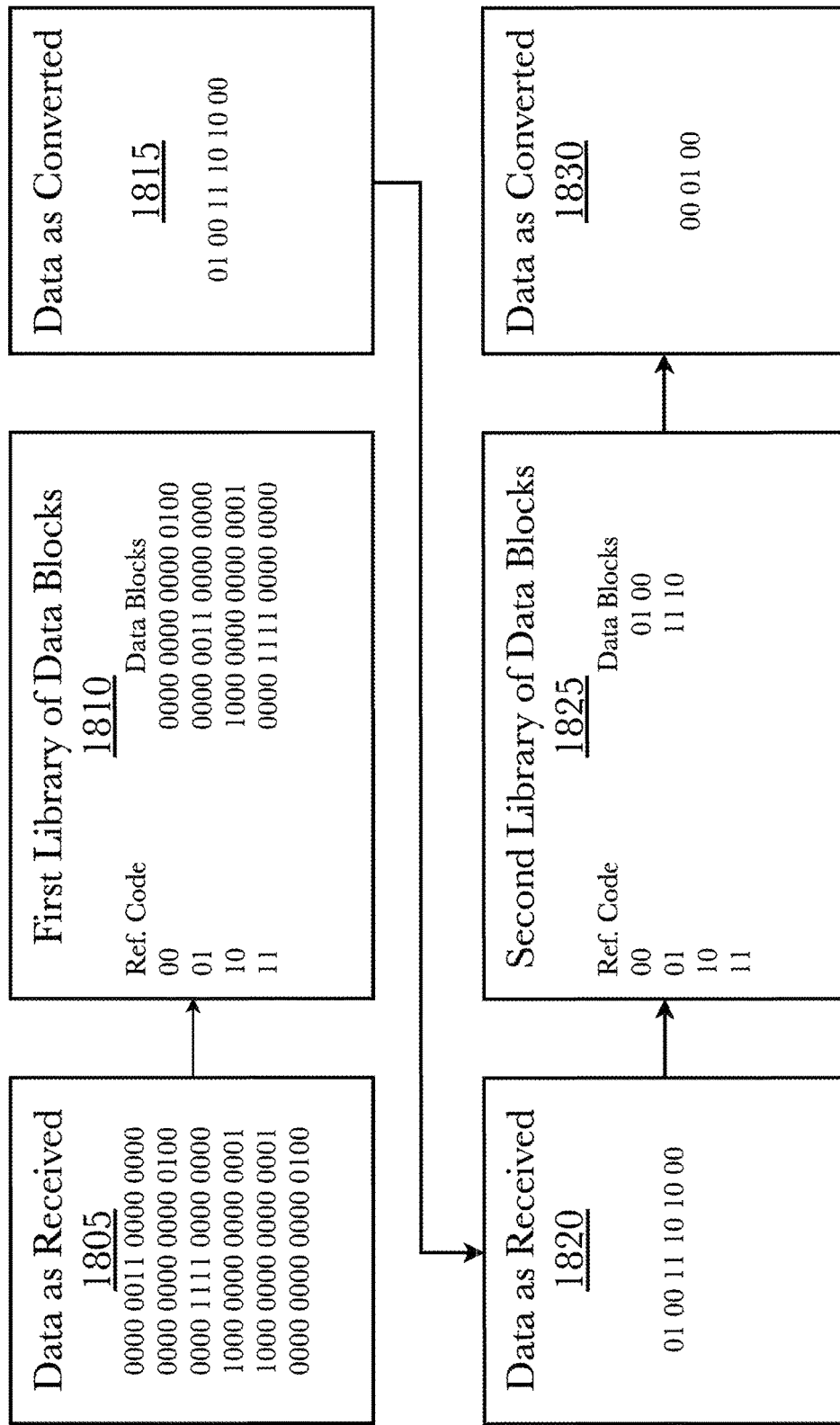
FIG. 18 is a flow diagram illustrating the use of a data encoding system used to recursively encode data to further reduce data size.

FIG. 18 is a flow diagram illustrating the use of a data encoding system used to recursively encode data to further reduce data size. Data may be input 1805 into a data deconstruction engine 102 to be deconstructed into code references, using a library of code references based on the input 1810. Such example data is shown in a converted, encoded format 1815, highly compressed, reducing the example data from 96 bits of data, to 12 bits of data, before sending this newly encoded data through the process again 1820, to be encoded by a second library 1825, reducing it even further. The newly converted data 1830 is shown as only 6 bits in this example, thus a size of 6.25% of the original data packet. With recursive encoding, then, it is possible and implemented in the system to achieve increasing compression ratios, using multi-layered encoding, through recursively encoding data. Both initial encoding libraries 1810 and subsequent libraries 1825 may be achieved through machine learning techniques to find optimal encoding patterns to reduce size, with the libraries being distributed to recipients prior to transfer of the actual encoded data, such that only the compressed data 1830 must be transferred or stored, allowing for smaller data footprints and bandwidth requirements. This process can be reversed to reconstruct the data. While this example shows only two levels of encoding, recursive encoding may be repeated any number of times. The number of levels of recursive encoding will depend on many factors, a non-exhaustive list of which includes the type of data being encoded, the size of the original data, the intended usage of the data, the number of instances of data being stored, and available storage space for codebooks and libraries. Additionally, recursive encoding can be applied not only to data to be stored or transmitted, but also to the codebooks and/or libraries, themselves. For example, many installations of different libraries could take up a substantial amount of storage space. Recursively encoding those different libraries to a single, universal library would dramatically reduce the amount of storage space required, and each different library could be reconstructed as necessary to reconstruct incoming streams of data.

Figure 20:
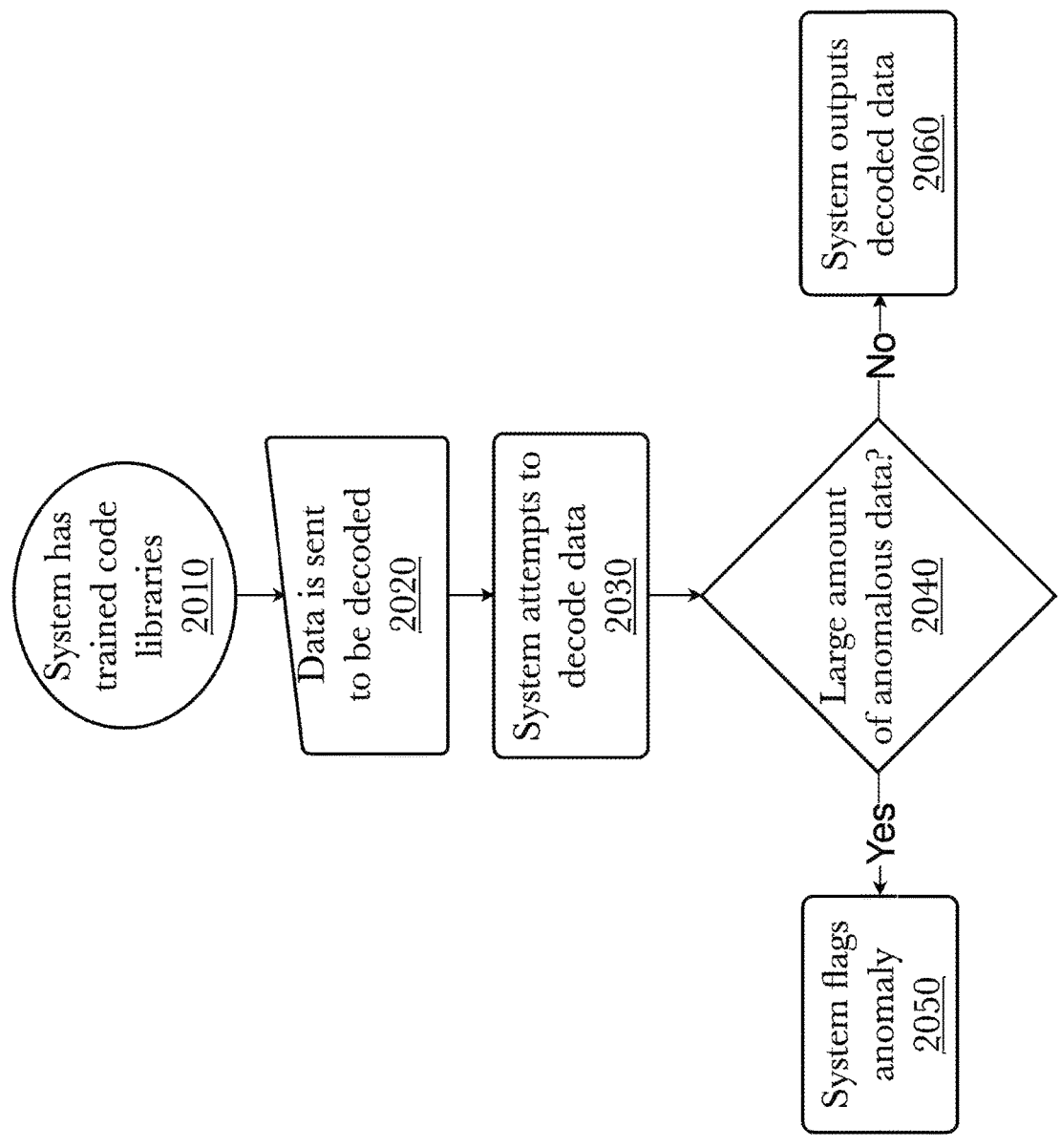
FIG. 20 is a flow diagram of an exemplary method used to detect anomalies in received encoded data and producing a warning.

FIG. 20 is a flow diagram of an exemplary method used to detect anomalies in received encoded data and producing a warning. A system may have trained encoding libraries 2010, before data is received from some source such as a network connected device or a locally connected device including USB connected devices, to be decoded 2020. Decoding in this context refers to the process of using the encoding libraries to take the received data and attempt to use encoded references to decode the data into its original source 2030, potentially more than once if recursive encoding was used, but not necessarily more than once. An anomaly detector 1910 may be configured to detect a large amount of un-encoded data 2040 in the midst of encoded data, by locating data or references that do not appear in the encoding libraries, indicating at least an anomaly, and potentially data tampering or faulty encoding libraries. A flag or warning is set by the system 2050, allowing a user to be warned at least of the presence of the anomaly and the characteristics of the anomaly. However, if a large amount of invalid references or unencoded data are not present in the encoded data that is attempting to be decoded, the data may be decoded and output as normal 2060, indicating no anomaly has been detected.

Figure 21:
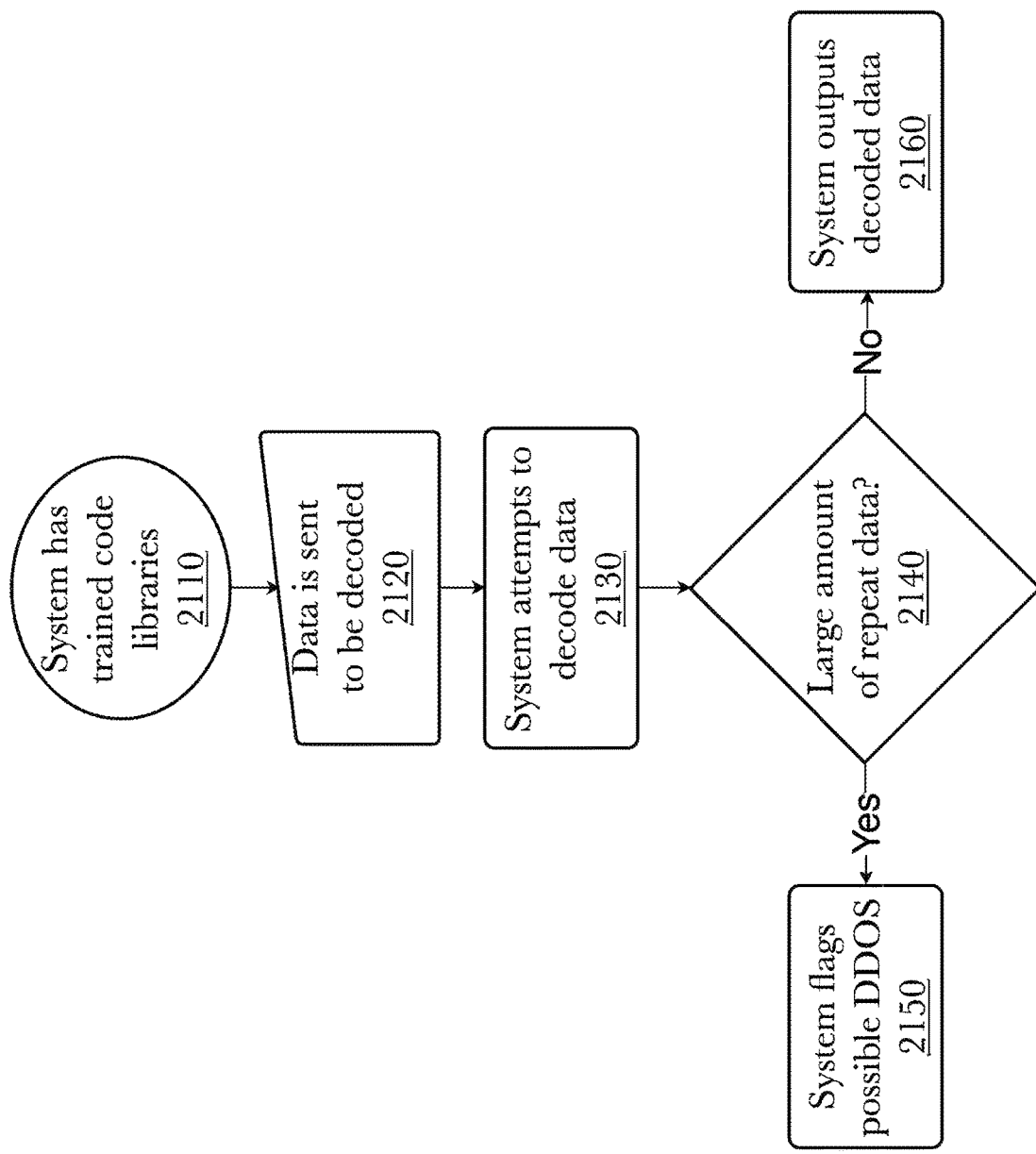
FIG. 21 is a flow diagram of a data encoding system used for Distributed Denial of Service (DDoS) attack denial.

FIG. 21 is a flow diagram of a method used for Distributed Denial of Service (DDoS) attack denial. A system may have trained encoding libraries 2110, before data is received from some source such as a network connected device or a locally connected device including USB connected devices, to be decoded 2120. Decoding in this context refers to the process of using the encoding libraries to take the received data and attempt to use encoded references to decode the data into its original source 2130, potentially more than once if recursive encoding was used, but not necessarily more than once. A DDoS detector 1920 may be configured to detect a large amount of repeating data 2140 in the encoded data, by locating data or references that repeat many times over (the number of which can be configured by a user or administrator as need be), indicating a possible DDoS attack. A flag or warning is set by the system 2150, allowing a user to be warned at least of the presence of a possible DDoS attack, including characteristics about the data and source that initiated the flag, allowing a user to then block incoming data from that source. However, if a large amount of repeat data in a short span of time is not detected, the data may be decoded and output as normal 2160, indicating no DDoS attack has been detected.

Figure 23:
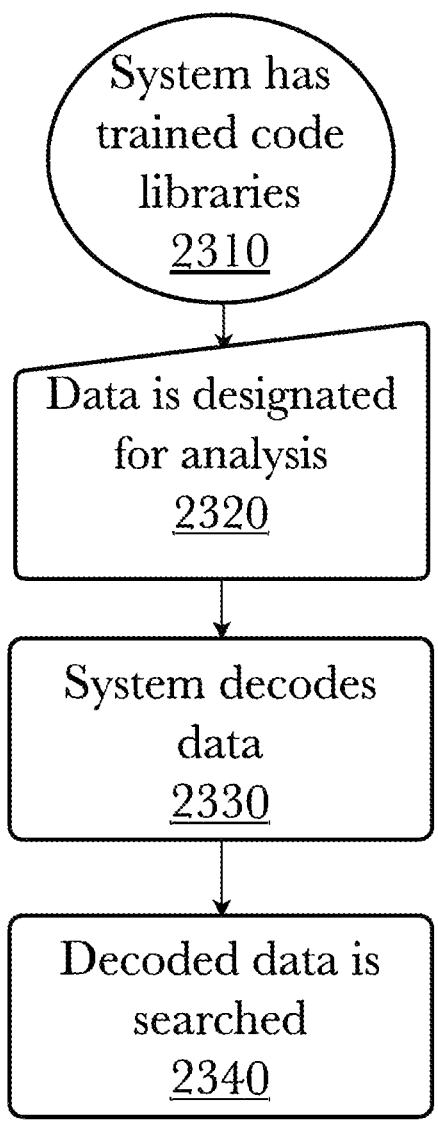
FIG. 23 is a flow diagram of an exemplary method used to enable high-speed data mining of repetitive data.

FIG. 23 is a flow diagram of an exemplary method used to enable high-speed data mining of repetitive data. A system may have trained encoding libraries 2310, before data is received from some source such as a network connected device or a locally connected device including USB connected devices, to be analyzed 2320 and decoded 2330. When determining data for analysis, users may select specific data to designate for decoding 2330, before running any data mining or analytics functions or software on the decoded data 2340. Rather than having traditional decryption and decompression operate over distributed drives, data can be regenerated immediately using the encoding libraries disclosed herein, as it is being searched. Using methods described in FIG. 9 and FIG. 11, data can be stored, retrieved, and decoded swiftly for searching, even across multiple devices, because the encoding library may be on each device. For example, if a group of servers host codewords relevant for data mining purposes, a single computer can request these codewords, and the codewords can be sent to the recipient swiftly over the bandwidth of their connection, allowing the recipient to locally decode the data for immediate evaluation and searching, rather than running slow, traditional decompression algorithms on data stored across multiple devices or transfer larger sums of data across limited bandwidth.

Figure 25:
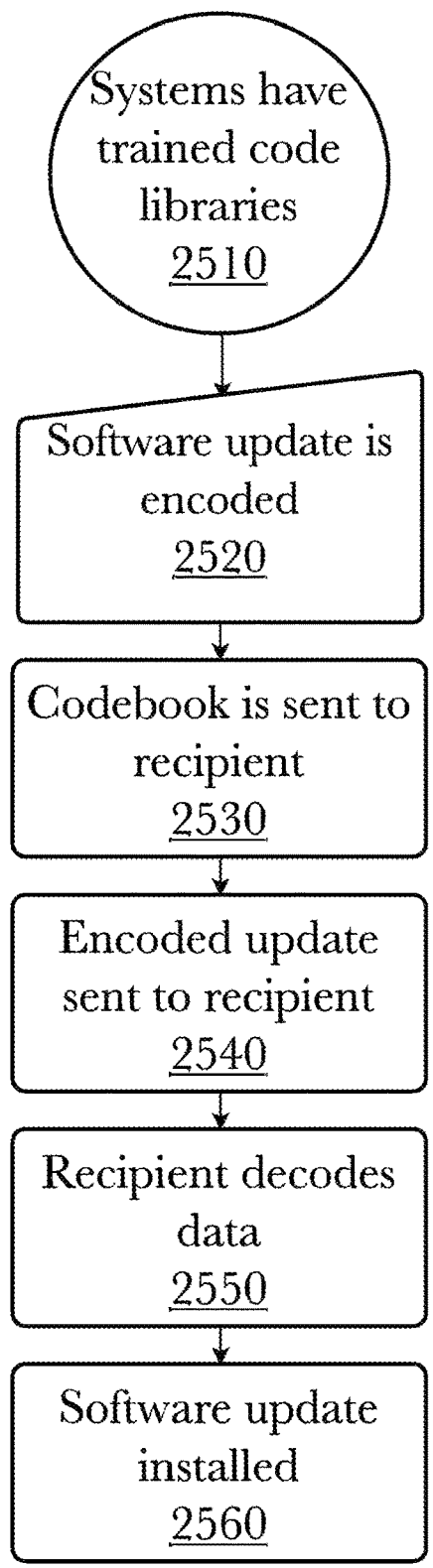
FIG. 25 is a flow diagram of an exemplary method used to encode and transfer software and firmware updates to a device for installation, for the purposes of reduced bandwidth consumption.

FIG. 25 is a flow diagram of an exemplary method used to encode and transfer software and firmware updates to a device for installation, for the purposes of reduced bandwidth consumption. A first system may have trained code libraries or "codebooks" present 2510, allowing for a software update of some manner to be encoded 2520. Such a software update may be a firmware update, operating system update, security patch, application patch or upgrade, or any other type of software update, patch, modification, or upgrade, affecting any computer system. A codebook for the patch must be distributed to a recipient 2530, which may be done beforehand and either over a network or through a local or physical connection, but must be accomplished at some point in the process before the update may be installed on the recipient device 2560. An update may then be distributed to a recipient device 2540, allowing a recipient with a codebook distributed to them 2530 to decode the update 2550 before installation 2560. In this way, an encoded and thus heavily compressed update may be sent to a recipient far quicker and with less bandwidth usage than traditional lossless compression methods for data, or when sending data in uncompressed formats. This especially may benefit large distributions of software and software updates, as with enterprises updating large numbers of devices at once.

Figure 27:
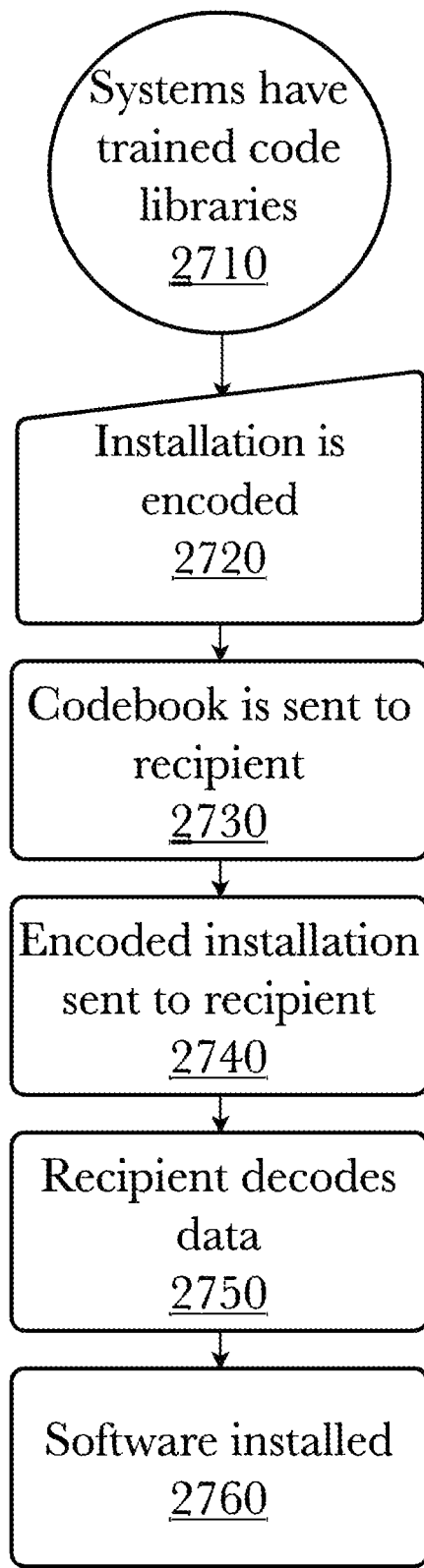
FIG. 27 is a flow diagram of an exemplary method used to encode new software and operating system installations for reduced bandwidth required for transference.

FIG. 27 is a flow diagram of an exemplary method used to encode new software and operating system installations for reduced bandwidth required for transference. A first system may have trained code libraries or "codebooks" present 2710, allowing for a software installation of some manner to be encoded 2720. Such a software installation may be a software update, operating system, security system, application, or any other type of software installation, execution, or acquisition, affecting a computer system. An encoding library or "codebook" for the installation must be distributed to a recipient 2730, which may be done beforehand and either over a network or through a local or physical connection, but must be accomplished at some point in the process before the installation can begin on the recipient device 2760. An installation may then be distributed to a recipient device 2740, allowing a recipient with a codebook distributed to them 2730 to decode the installation 2750 before executing the installation 2760. In this way, an encoded and thus heavily compressed software installation may be sent to a recipient far quicker and with less bandwidth usage than traditional lossless compression methods for data, or when sending data in uncompressed formats. This especially may benefit large distributions of software and software updates, as with enterprises updating large numbers of devices at once.

Figure 31:
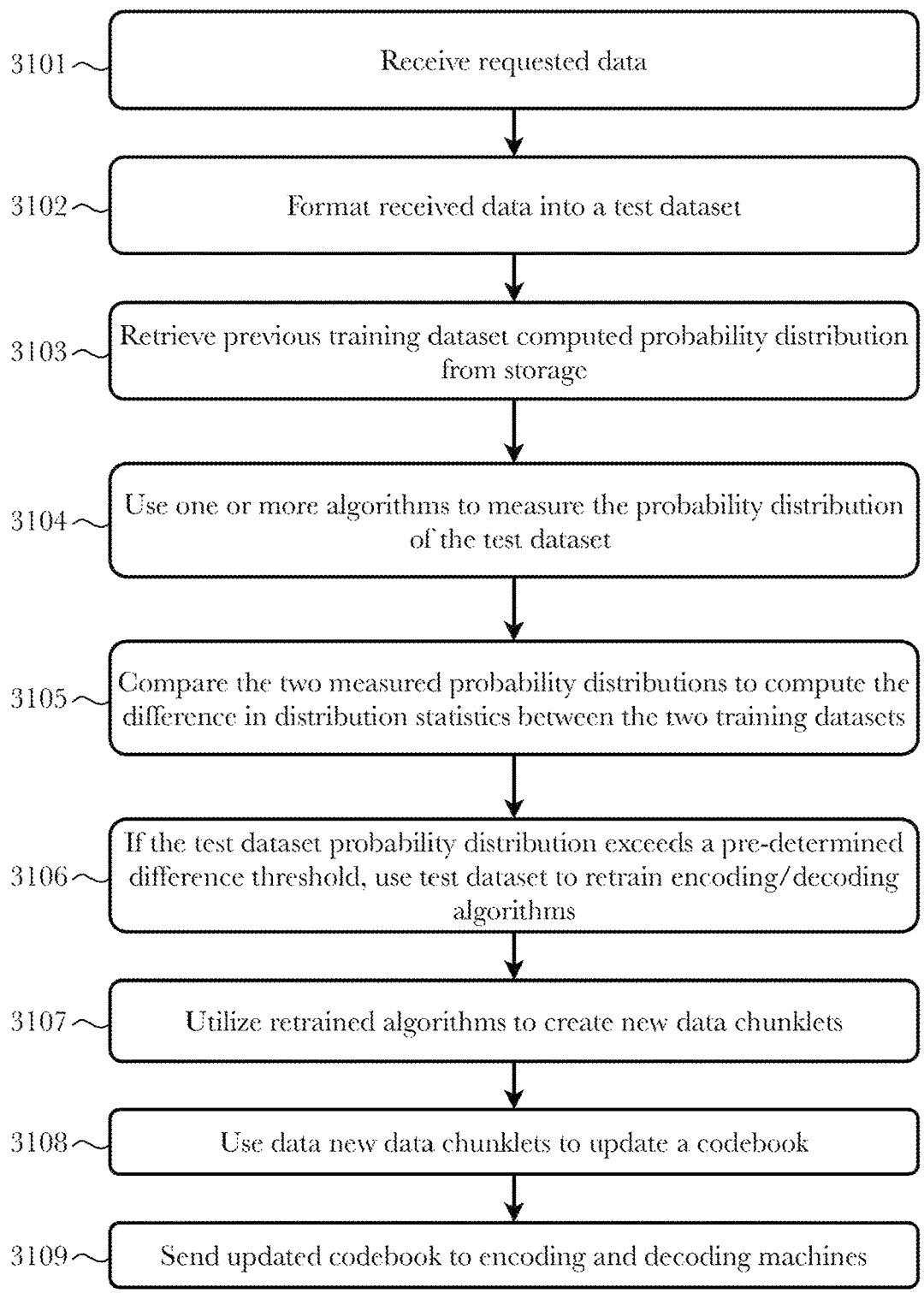
FIG. 31 is a method diagram illustrating the steps involved in using an embodiment of the codebook training system to update a codebook.

FIG. 31 is a method diagram illustrating the steps 3100 involved in using an embodiment of the codebook training system to update a codebook. The process begins when requested data is received 3101 by a codebook training module. The requested data may comprise a plurality of sourceblocks. Next, the received data may be stored in a cache and formatted into a test dataset 3102. The next step is to retrieve the previously computed probability distribution associated with the previous (most recent) training dataset from a storage device 3103. Using one or more algorithms, measure and record the probability distribution of the test dataset 3104. The step after that is to compare the measured probability distributions of the test dataset and the previous training dataset to compute the difference in distribution statistics between the two datasets 3105. If the test dataset probability distribution exceeds a pre-determined difference threshold, then the test dataset will be used to retrain the encoding/decoding algorithms 3106 to reflect the new distribution of the incoming data to the encoder/decoder system. The retrained algorithms may then be used to create new data sourceblocks 3107 that better capture the nature of the data being received. These newly created data sourceblocks may then be used to create new codewords and update a codebook 3108 with each new data sourceblock and its associated new codeword. Last, the updated codebooks may be sent to encoding and decoding machines 3109 in order to ensure the encoding/decoding system function properly.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 43:
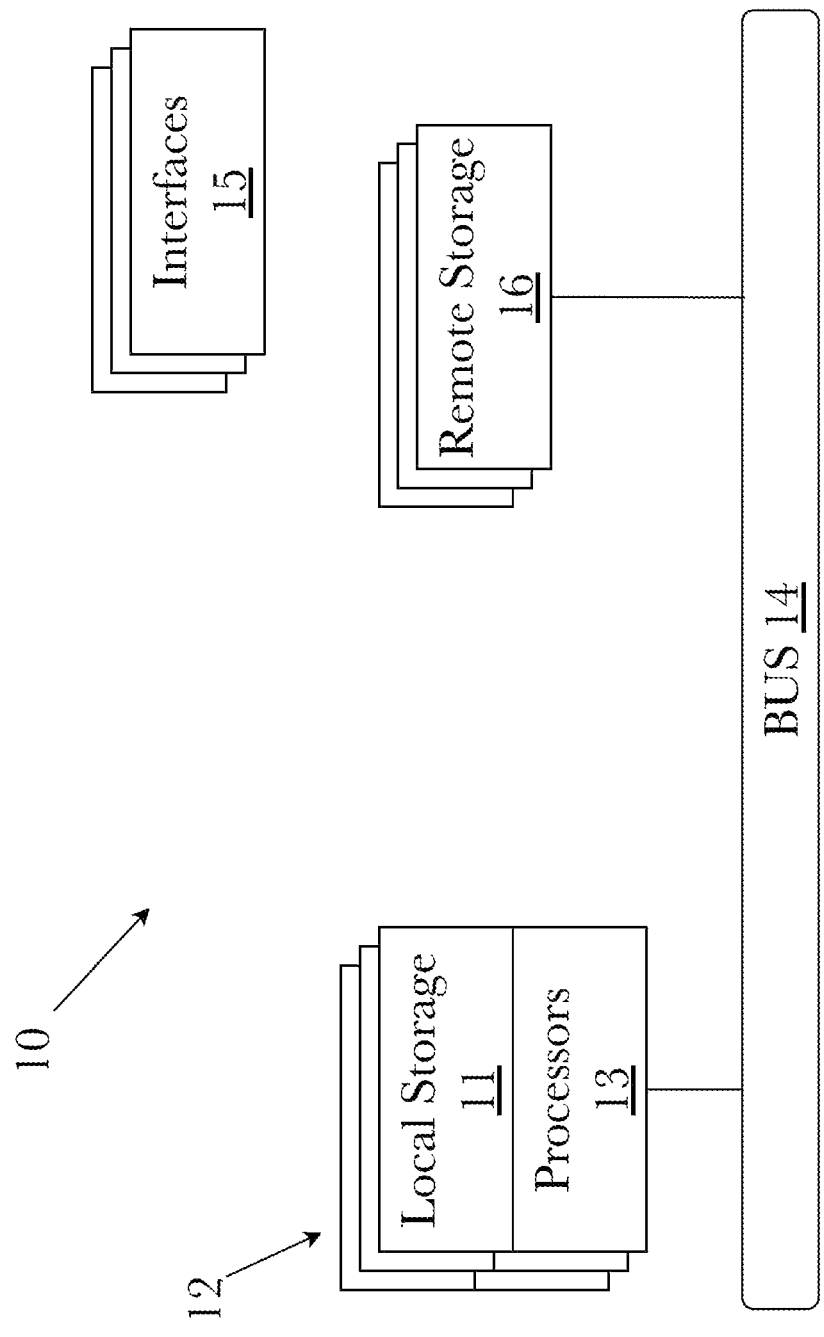
FIG. 43 is a block diagram illustrating an exemplary hardware architecture of a computing device.

Referring now to FIG. 43, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™ THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 43 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 44:
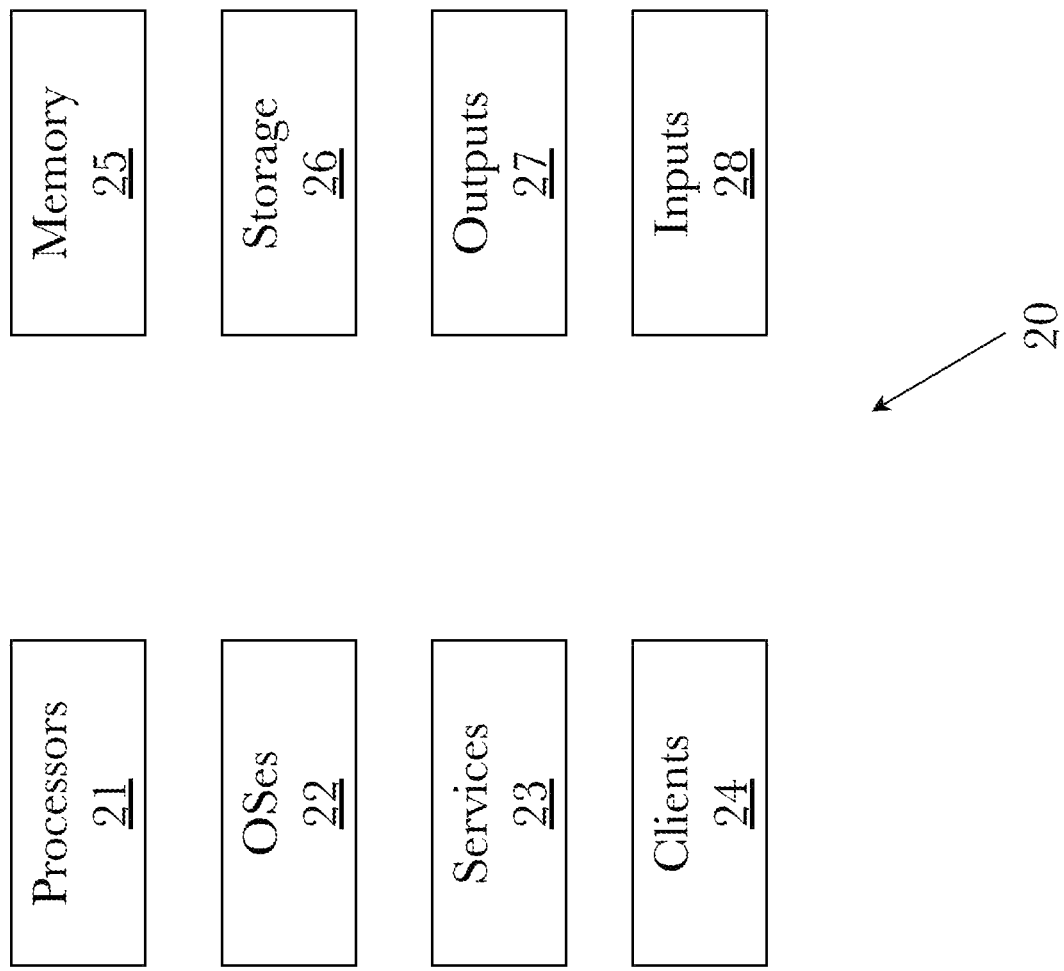
FIG. 44 is a block diagram illustrating an exemplary logical architecture for a client device.

In some aspects, systems may be implemented on a standalone computing system. Referring now to FIG. 44, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 43).

Examples of storage devices 26 include flash memory, magnetic hard drive, CD-ROM, and/or the like.

Figure 45:
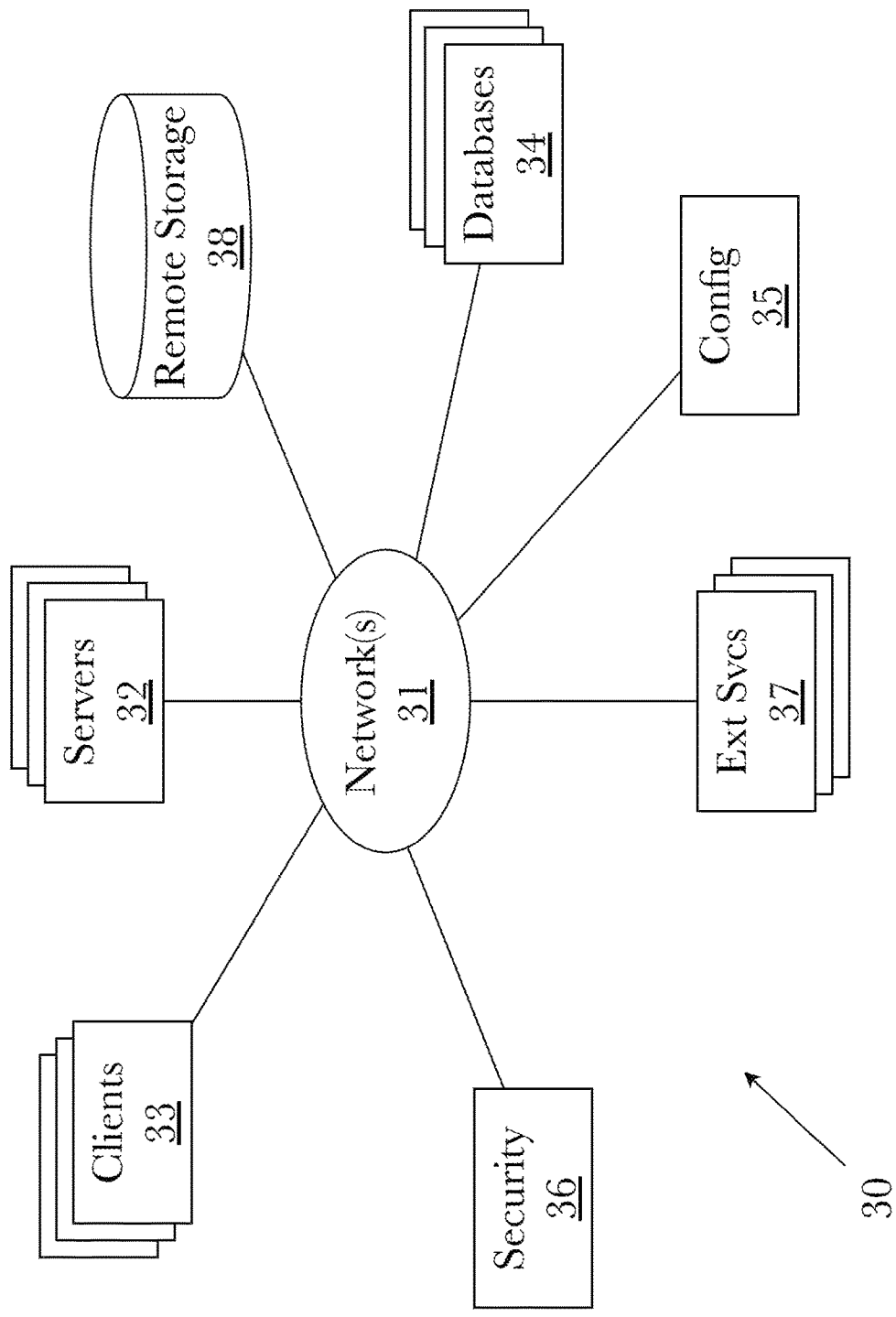
FIG. 45 is a block diagram showing an exemplary architectural arrangement of clients, servers, and external services.

In some aspects, systems may be implemented on a distributed computing network, such as one having any number of clients and/or servers. Referring now to FIG. 45, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 44. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 46:
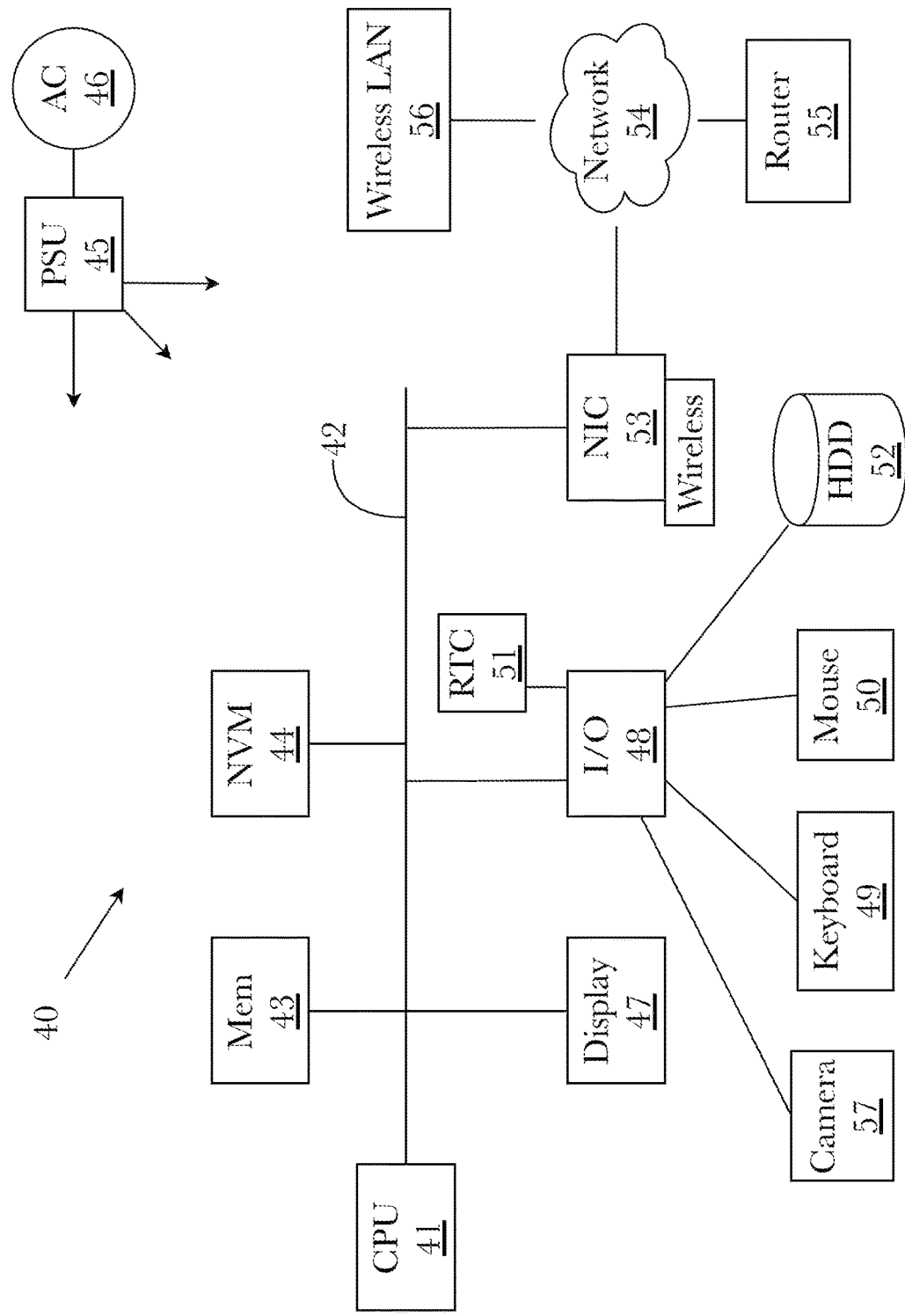
FIG. 46 is another block diagram illustrating an exemplary hardware architecture of a computing device.

FIG. 46 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for genomic data compression with encryption, comprising:
   a computing device comprising a processor and a memory;

a stream analyzer comprising a first plurality of programming instructions stored in the memory which, when operating on the processor, causes the computing device to:
  receive an input data stream comprising genomic data;
  analyze the frequency distribution of a plurality of data blocks within the input data stream to determine whether the input data stream meets a configured threshold for data conditioning;
  if the input data stream meets or exceeds the configured threshold, send the input data stream to a stream conditioner; and
the stream conditioner comprising a second plurality of programming instructions stored in the memory which, when operating on the processor, causes the computing device to:
  receive the input data stream from the stream analyzer;
  produce a conditioned data stream and an error stream by, for each of a plurality of data blocks within the data stream:
    analyzing the data block within the data stream to compare the data block's real frequency within the data stream against an ideal frequency;
    if the difference between the data block's real frequency and ideal frequency exceeds a configured conditioning threshold, applying a conditioning rule to the data block;
    applying a logical XOR operation to the data block;
    appending the output of the logical XOR operation to the error stream;
  send the conditioned data stream and the error stream as output.

2. The system of claim 1, wherein the stream analyzer is further configured to:
  analyze the frequency distribution of the plurality of data blocks within the input data stream to determine the most frequent bytes or strings of bytes that occur at the beginning of each of the plurality of data blocks;
  designate the most-frequent bytes or strings of bytes as prefixes;
  compile a prefix table based on the results of the frequency distribution, the prefix table comprising the designated prefixes and the block lengths;
  send the prefix table to a data transformer.

3. The system of claim 2, further comprising the data transformer comprising a third plurality of programming instructions stored in the memory which, when operating on the processor, causes the computing device to:
  receive the prefix table;
  transform each of the plurality of prefixes within the prefix table by applying a Burrow's-Wheeler transform (BWT) and generating as output a plurality BWT-prefixes; and
  send the plurality of BWT-prefixes as output.

4. The system of claim 2, wherein each of the plurality of data blocks are k-mers of the genomic data and the prefixes are one or more base pairs that occur at the beginning of each k-mer.

5. A method for genomic data compression with encryption, comprising the steps of:
  receiving an input data stream comprising genomic data;
  analyzing the frequency distribution of a plurality of data blocks within the input data stream to determine whether the input data stream meets a configured threshold for data conditioning;
  if the input data stream meets or exceeds the configured threshold, sending the input data stream to a stream conditioner;
  receiving the input data stream from the stream analyzer;
  producing a conditioned data stream and an error stream by, for each of a plurality of data blocks within the data stream:
  analyzing the data block within the data stream to compare the data block's real frequency within the data stream against an ideal frequency;
  if the difference between the data block's real frequency and ideal frequency exceeds a configured conditioning threshold, applying a conditioning rule to the data block;
  applying a logical XOR operation to the data block;
  appending the output of the logical XOR operation to the error stream; and
  sending the conditioned data stream and the error stream as output.

6. The method of claim 5, further comprising the steps of:
  analyzing the frequency distribution of the plurality of data blocks within the input data stream to determine the most frequent bytes or strings of bytes that occur at the beginning of each of the plurality of data blocks;
  designating the most-frequent bytes or strings of bytes as prefixes;
  compiling a prefix table based on the results of the frequency distribution, the prefix table comprising the designated prefixes and the block lengths; and
  sending the prefix table to a data transformer.

7. The method of claim 6, further comprising the steps of:
  receiving the prefix table using the data transformer;
  transforming each of the plurality of prefixes within the prefix table by applying a Burrow's-Wheeler transform (BWT) and generating as output a plurality BWT-prefixes using the data transformer; and
  sending the plurality of BWT-prefixes as output using the data transformer.

8. The method of claim 6, wherein each of the plurality of data blocks are k-mers of the genomic data and the prefixes are one or more base pairs that occur at the beginning of each k-mer.

* * * * *